US012575835B2

(12) United States Patent
Li

(10) Patent No.: US 12,575,835 B2
(45) Date of Patent: Mar. 17, 2026

(54) CLIP APPLYING MECHANISM AND CLIP APPLYING APPARATUS THEREOF

(71) Applicant: INTOCARE MEDICAL TECHNOLOGY (SUZHOU) CO., LTD., Jiangsu (CN)

(72) Inventor: Daping Li, Jiangsu (CN)

(73) Assignee: INTOCARE MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 359 days.

(21) Appl. No.: 18/321,040

(22) Filed: May 22, 2023

(65) Prior Publication Data

US 2024/0122606 A1 Apr. 18, 2024

(30) Foreign Application Priority Data

Oct. 18, 2022 (CN) .......................... 202211269429.1

(51) Int. Cl.
*A61B 17/128* (2006.01)
*A61B 17/10* (2006.01)
*A61B 17/12* (2006.01)

(52) U.S. Cl.
CPC ........ *A61B 17/1285* (2013.01); *A61B 17/105* (2013.01); *A61B 2017/12004* (2013.01)

(58) Field of Classification Search
CPC .... A61B 2090/034; A61B 2017/12004; A61B 2017/0046; A61B 2017/00367; A61B 17/1285; A61B 17/105; A61B 17/128
See application file for complete search history.

(56) References Cited

U.S. PATENT DOCUMENTS

| | | | |
|---|---|---|---|
| 5,171,247 A | 12/1992 | Hughett et al. | |
| 11,213,298 B2 | 1/2022 | Sorrentino et al. | |

(Continued)

FOREIGN PATENT DOCUMENTS

| | | |
|---|---|---|
| CN | 112704538 A | 4/2021 |
| CN | 114191026 A | 3/2022 |

(Continued)

OTHER PUBLICATIONS

EP Search Report dated Mar. 11, 2024 in European application No. 233173616.6-1122.

(Continued)

*Primary Examiner* — Brooke Labranche
(74) *Attorney, Agent, or Firm* — McClure, Qualey & Rodack, LLP

(57) ABSTRACT

A clip applying mechanism and a clip applying apparatus thereof are provided. The clip applying mechanism includes a tube body, a main shaft, a clip-cartridge assembly, a clip-pushing assembly and a firing assembly; and further includes: a main-shaft connecting member, connected with the main shaft; a firing connecting member, connected with the firing assembly; an engagement mechanism, arranged between the main-shaft connecting member and the firing connecting member. The engagement mechanism, the firing connecting member, the main-shaft connecting member and the firing assembly are configured such that: in a case where the clip is fired, the main-shaft connecting member drives the firing connecting member to move in a direction facing away from the head end of the tube body through the engagement mechanism, and the firing connecting member drives the firing assembly to move in a same direction, so that the end effector is partially opened.

18 Claims, 28 Drawing Sheets

(56) References Cited

U.S. PATENT DOCUMENTS

| 2003/0014060 A1 | 1/2003 | Wilson, Jr. et al. |
| 2017/0128071 A1 | 5/2017 | Holsten et al. |
| 2019/0053808 A1 | 2/2019 | Baril et al. |
| 2019/0099183 A1 | 4/2019 | Leimbach et al. |

FOREIGN PATENT DOCUMENTS

| EP | 3210546 A1 | 8/2017 |
| JP | 2017192711 A | 10/2017 |
| JP | 2019503223 A | 2/2019 |
| JP | 2021501021 A | 1/2021 |

OTHER PUBLICATIONS

EP Search Report dated Mar. 11, 2024 in European application No. 233175157.9-1122.
EP Search Report dated Jan. 29, 2024 in European application No. 23183058.9-1122.
EP Search Report dated Mar. 14, 2024 in European application No. 23183067.0-1122.
KR Office Action dated Apr. 22, 2025 in application No. 10-2023-0085238 (English machine translation, pp. 5-9).

CLIP APPLYING MECHANISM AND CLIP APPLYING APPARATUS THEREOF

TECHNICAL FIELD

The present disclosure relates to a field of medical devices, and more particularly, to a clip applying mechanism and a clip applying apparatus thereof.

BACKGROUND

In surgery, a surgical instrument is needed to close a blood vessel to avoid blood loss from incision at a surgical site. Usually, the clip applying apparatus includes a long rod-shaped clip applying mechanism and a handle assembly. The clip applying mechanism may penetrate into a human body via an auxiliary tool, for example, a puncture device. Through operating the handle assembly, the clip applying mechanism may be controlled to convey a ligating clip (briefly referred to as a clip) to an end effector located at the front end of the clip applying mechanism, and then close the end effector to allow the clip to clamp the blood vessel.

SUMMARY

Embodiments of the present disclosure provide a clip applying mechanism and a clip applying apparatus thereof.

According to first aspect of the present disclosure, it is provided a clip applying mechanism of a clip applying apparatus, comprising: a tube body, comprising a head end and a tail end opposite to each other; a main shaft, the main shaft being arranged proximal to the tail end and at least portion of the main shaft being arranged in the tube body; a clip-cartridge assembly, the clip-cartridge assembly being configured to penetrate through the tube body and comprising: a clip cartridge arranged in the tube body and an end effector configured to penetrate out of the head end; the clip cartridge being configured to be filled with a clip; a clip-pushing assembly, at least portion of the clip-pushing assembly being arranged in the tube body, and the clip-pushing assembly being configured to be pushed by the main shaft toward the head end to convey the clip in the clip cartridge into the end effector; and a firing assembly, at least portion of the firing assembly being located in the tube body, and the firing assembly being configured to be pushed by the main shaft toward the head end to close the end effector, so that the clip in the end effector is fired; wherein the clip applying mechanism further comprises: a main-shaft connecting member, connected with the main shaft; a firing connecting member, connected with the firing assembly; an engagement mechanism, arranged between the main-shaft connecting member and the firing connecting member; wherein the engagement mechanism, the firing connecting member, the main-shaft connecting member and the firing assembly are configured such that: in a case where the clip is fired, the main-shaft connecting member drives the firing connecting member to move in a direction facing away from the head end through the engagement mechanism, and the firing connecting member drives the firing assembly to move in a same direction, so that the end effector is partially opened.

In at least some embodiments, the engagement mechanism comprises: a first engagement member, arranged on the main-shaft connecting member; a second engagement member, arranged on the firing connecting member; wherein the engagement mechanism has a release state and a lock state; in the release state, the first engagement member is located in the second engagement member and is capable of moving out of the second engagement member; and in the lock state, the first engagement member and the second engagement member are locked with each other.

In at least some embodiments, the clip applying mechanism has a firing completion state and a retreat state; in the firing completion state, the clip in the end effector is fired; in the retreat state, there is no clip in the end effector, and the main-shaft connecting member is applied with an external force to retreat; the engagement mechanism is configured such that: in a case where the clip applying mechanism is in the firing completion state or the retreat state, the engagement mechanism is in the lock state.

In at least some embodiments, the clip applying mechanism has a clip feeding completion state and a gyration state; in the clip feeding completion state, the clip has been conveyed into the end effector; the engagement mechanism is configured such that: in a case where the clip applying mechanism is in the clip feeding completion state or the gyration state, the engagement mechanism is in the release state.

In at least some embodiments, the engagement mechanism further has a separate state; in the separate state, the first engagement member and the second engagement member are separated from each other, and the first engagement member is located outside the second engagement member.

In at least some embodiments, the clip applying mechanism further has an initial state; in the initial state, neither the main shaft nor the main-shaft connecting member is applied with an external force; the engagement mechanism is configured such that: in a case where the clip applying mechanism is in the initial state, the clip applying mechanism is in the separate state.

In at least some embodiments, the first engagement member comprises a pin; the second engagement member comprises a slot, the slot comprises a release position and a lock position, the pin is configured to be capable of moving between the release position and the lock position; the slot and the pin are configured such that: in a case where the engagement mechanism is in the lock state, the pin is in the lock position; in a case where the engagement mechanism is in the release state, the pin is in the release position and is capable of moving out of the slot; in a case where the engagement mechanism is in a separate state, the pin is located outside the slot.

In at least some embodiments, the firing connecting member is a tubular member, the slot is a through slot arranged on the tubular member; a notch of the slot is open toward the direction facing away from the head end, and the release position is located at a bottom of the slot.

In at least some embodiments, the firing assembly comprises: a firing sleeve and a firing rod at least partially located in the firing sleeve; the firing rod is connected with the firing connecting member and is configured to be driven by the firing connecting member to move in the direction facing away from the head end; the firing sleeve is used as the tube body, the firing sleeve is configured to be driven by the firing rod to move in the direction facing away from the head end, so that the end effector is partially opened.

In at least some embodiments, the clip applying mechanism further comprises: an axial engagement mechanism, arranged between the firing connecting member and the firing rod, the firing connecting member and the firing rod being configured to be engaged with each other in an axial direction of the firing connecting member through the axial engagement mechanism, and the firing connecting member and the firing rod are capable of achieving relative movement in a circumferential direction of the firing connecting member.

In at least some embodiments, the axial engagement mechanism comprises: a slot, arranged on the firing rod; and a tab, arranged on the firing connecting member, the tab being configured to move in the slot along the circumferential direction of the firing connecting member.

In at least some embodiments, the slot is an annular slot extending in the circumferential direction of the firing connecting member.

In at least some embodiments, the clip applying mechanism further comprises: a housing, the firing connecting member being located in the housing; a circumferential engagement mechanism, arranged between the firing connecting member and the housing, the firing connecting member and the housing being configured to be engaged with each other in a circumferential direction of the main shaft through the circumferential engagement mechanism, and the firing connecting member and the housing being capable of achieving relative movement in an axial direction of the main shaft.

In at least some embodiments, the housing comprises: a first housing portion and a second housing portion arranged in an axial direction of the tube body, wherein the first housing portion is proximal to the head end, the second housing portion is distal to the head end and is connected with the first housing portion; the first housing portion is configured to be capable of rotating in a circumferential direction of the main shaft relative to the second housing portion; the circumferential engagement mechanism comprises: a tab arranged on the second housing portion and a slot arranged on the firing connecting member; the tab and the slot are configured to be engaged with each other.

In at least some embodiments, the circumferential engagement mechanism comprises a plurality of tabs and a plurality of slots, the plurality of tabs and the plurality of slots are configured to be in one-to-one correspondence and be engaged with each other.

In at least some embodiments, the clip applying mechanism comprises a plurality of engagement mechanisms, the plurality of engagement mechanisms are arranged between the main-shaft connecting member and the firing connecting member along the circumferential direction of the main-shaft connecting member at equal interval.

In at least some embodiments, the main-shaft connecting member is a tubular member, the plurality of engagement mechanisms comprises two engagement mechanisms, and the two engagement mechanisms are symmetrically arranged in a radial direction of the tubular member.

According to second aspect of the present disclosure, it is provided a clip applying apparatus, comprising the above-mentioned clip applying mechanism.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

5

Figure 10A:
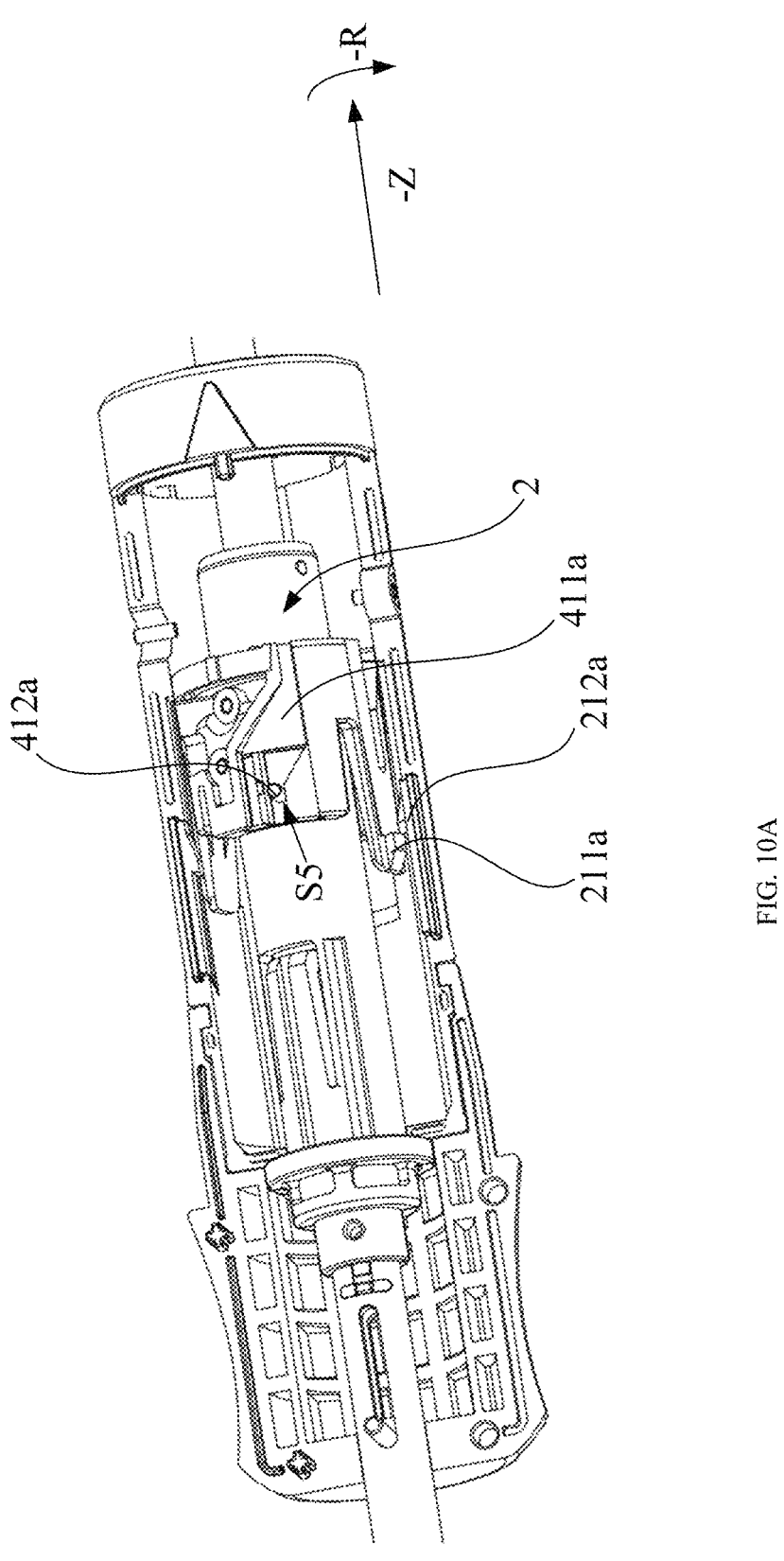
FIG. 10A is a first structural schematic diagram of the clip applying mechanism in a gyration state F according to the embodiment of the present disclosure.
Figure 10B:
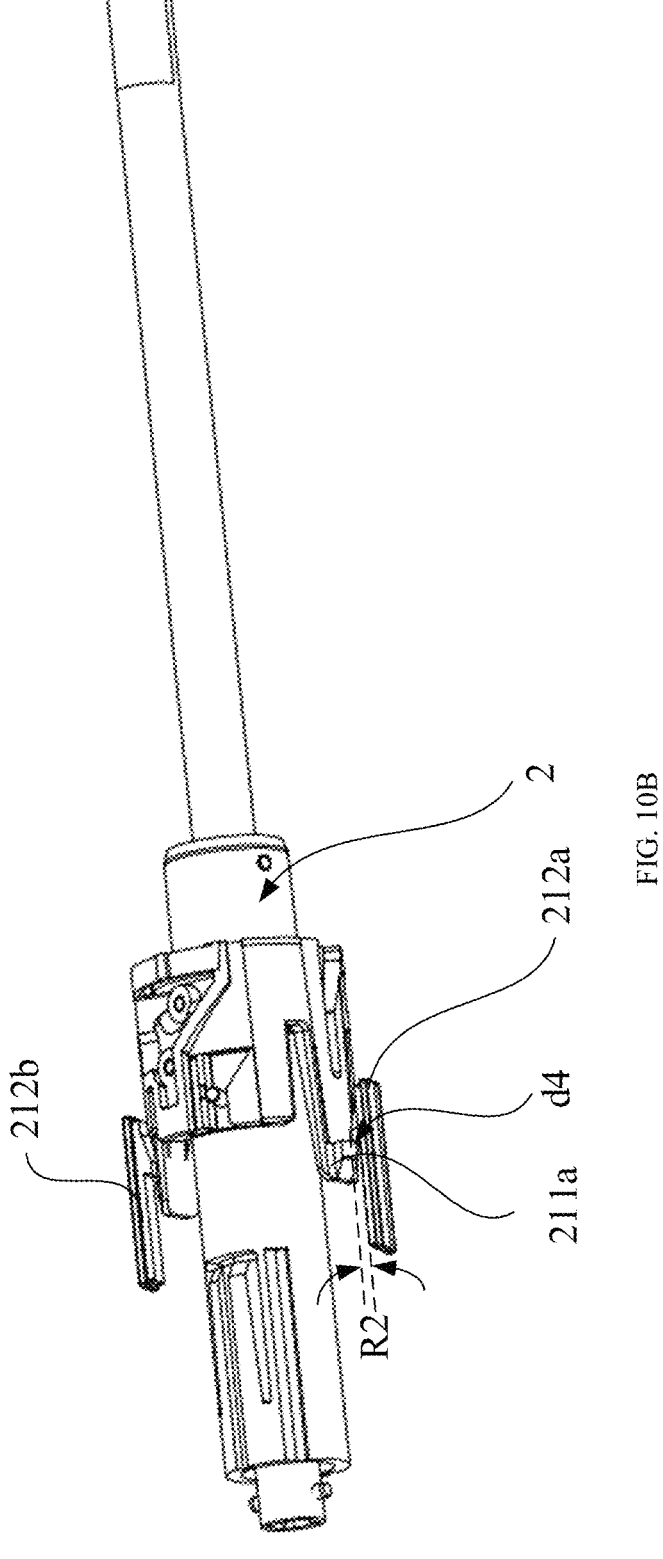

FIG. 10B is a second structural schematic diagram of the clip applying mechanism in the gyration state F according to the embodiment of the present disclosure.

Figure 10C:
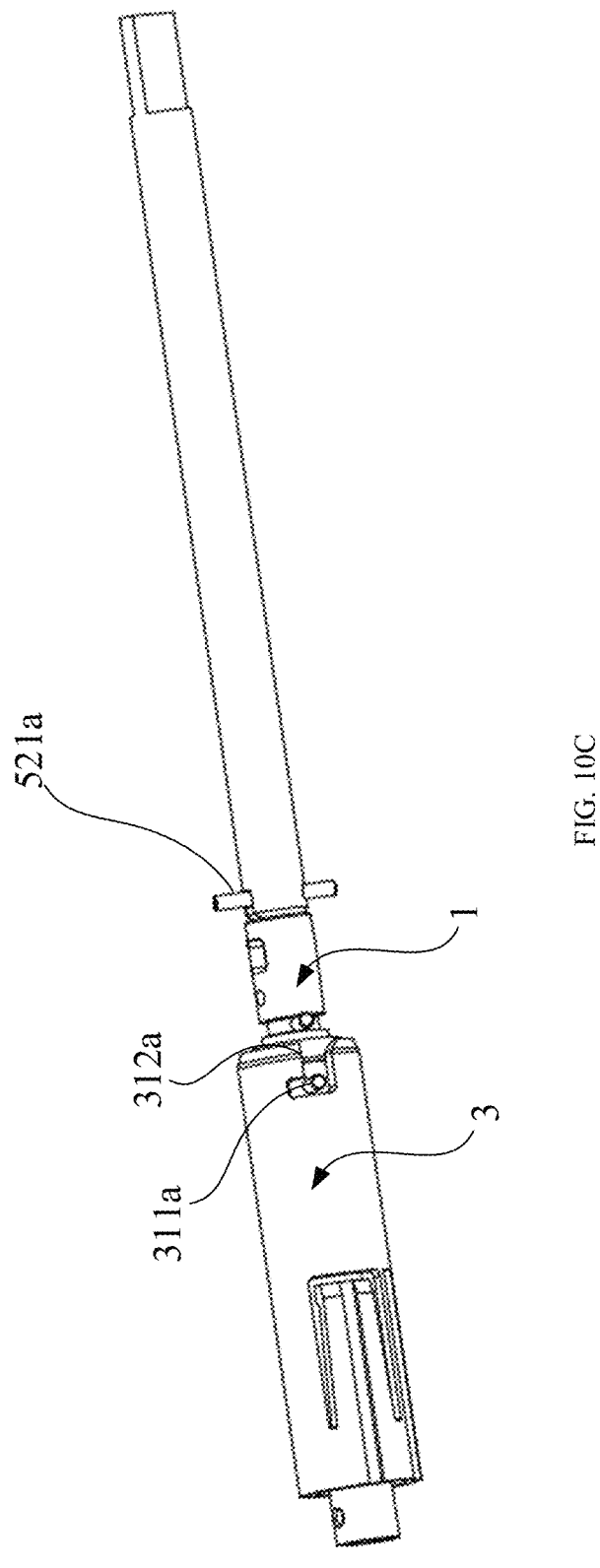

FIG. 10C is a third structural schematic diagram of the clip applying mechanism in the gyration state F according to the embodiment of the present disclosure.

Figure 10D:
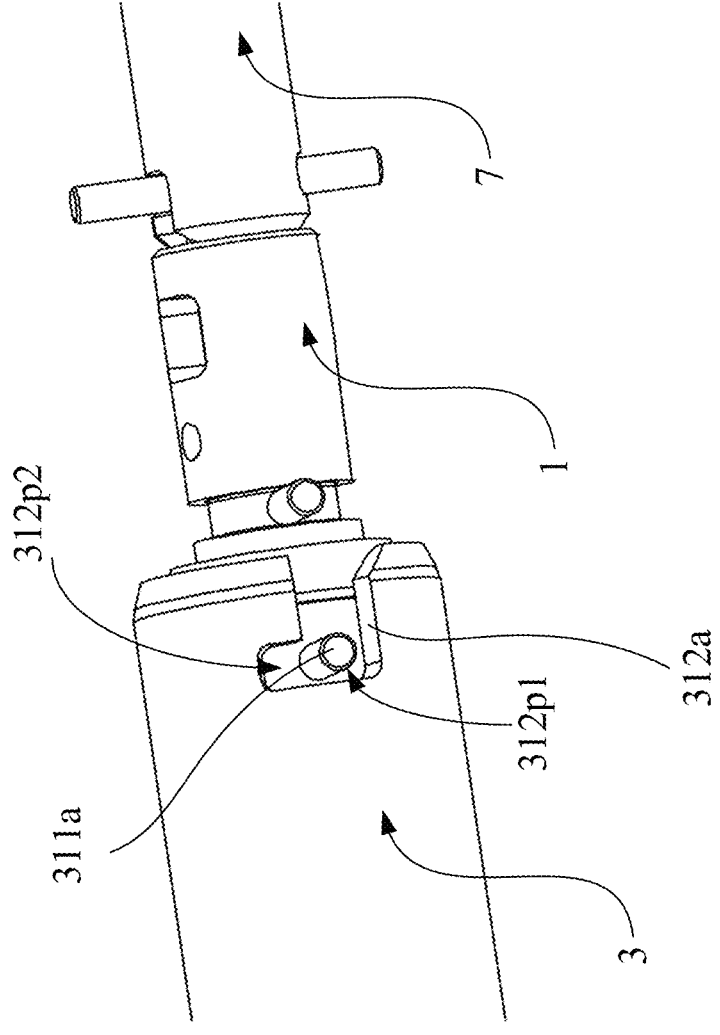

FIG. 10D is a partial enlarged structural schematic diagram of an engagement mechanism in FIG. 10C.

Figure 11:
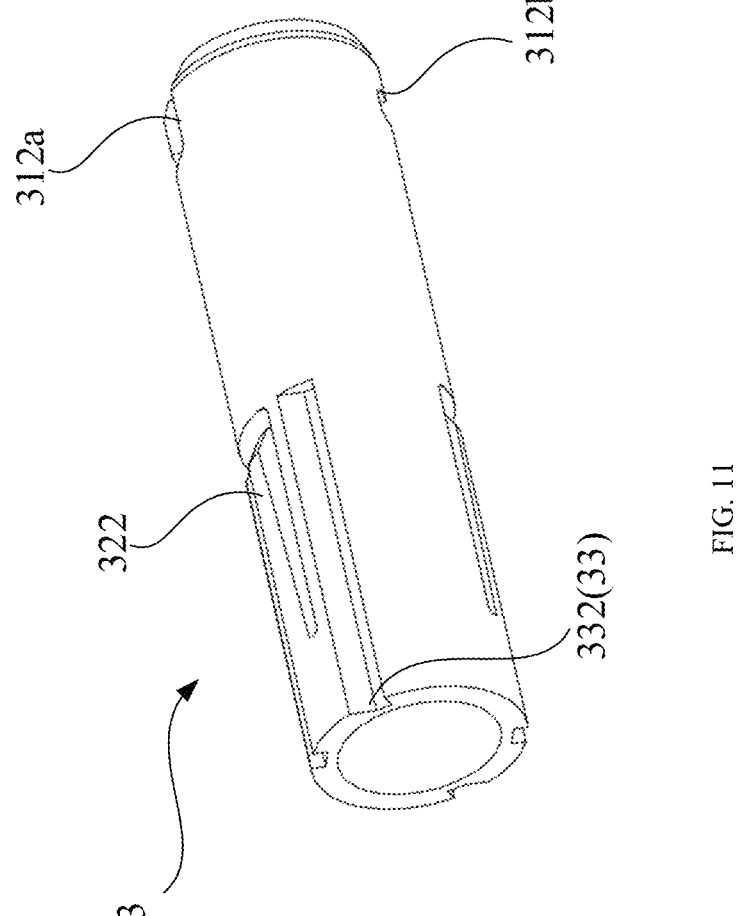

FIG. 11 is a structural schematic diagram of a firing connecting member according to the embodiment of the present disclosure.

Figure 12:
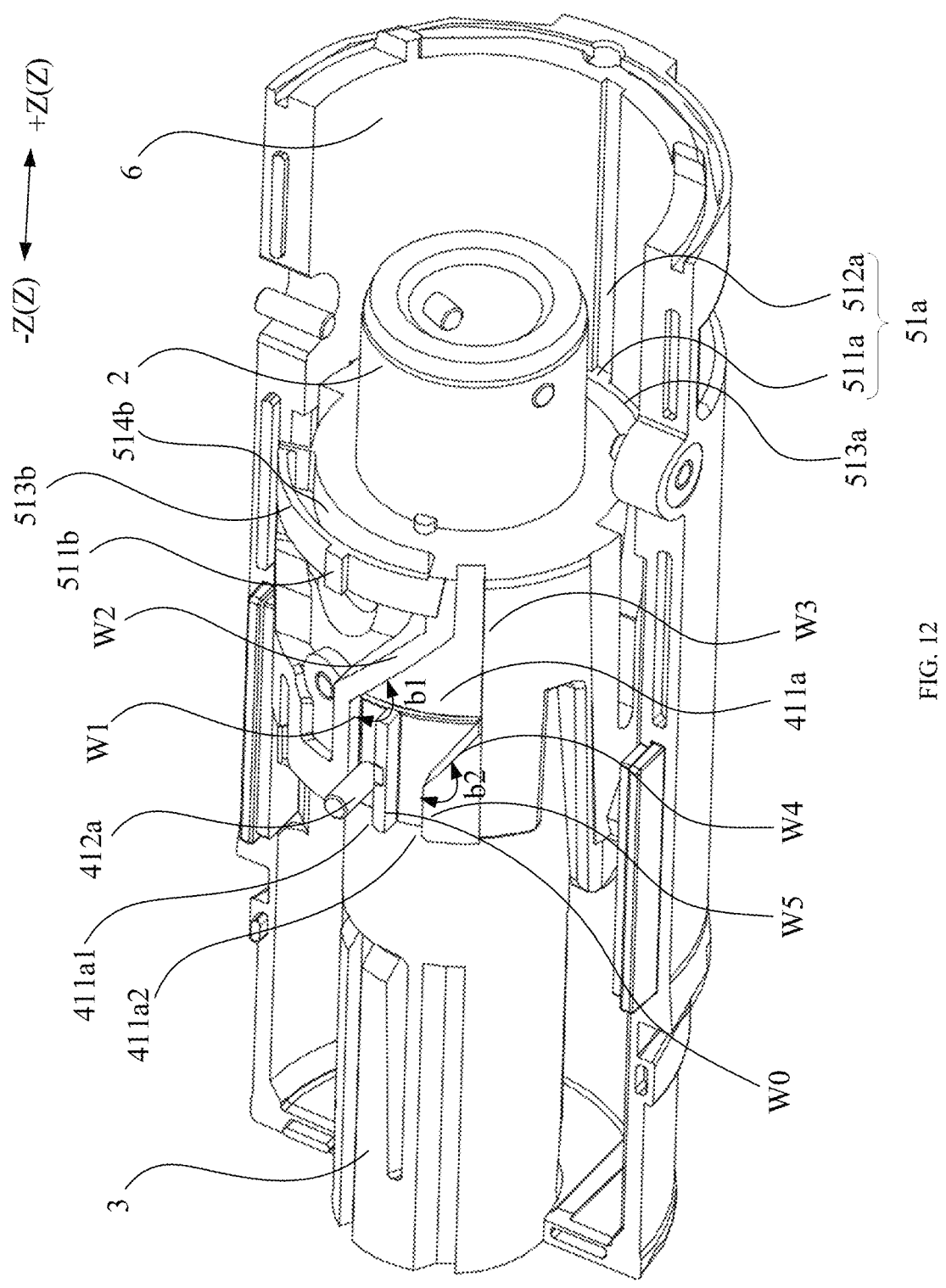

FIG. 12 is a partial structural schematic diagram of the clip applying mechanism according to the embodiment of the present disclosure.

Figure 13:
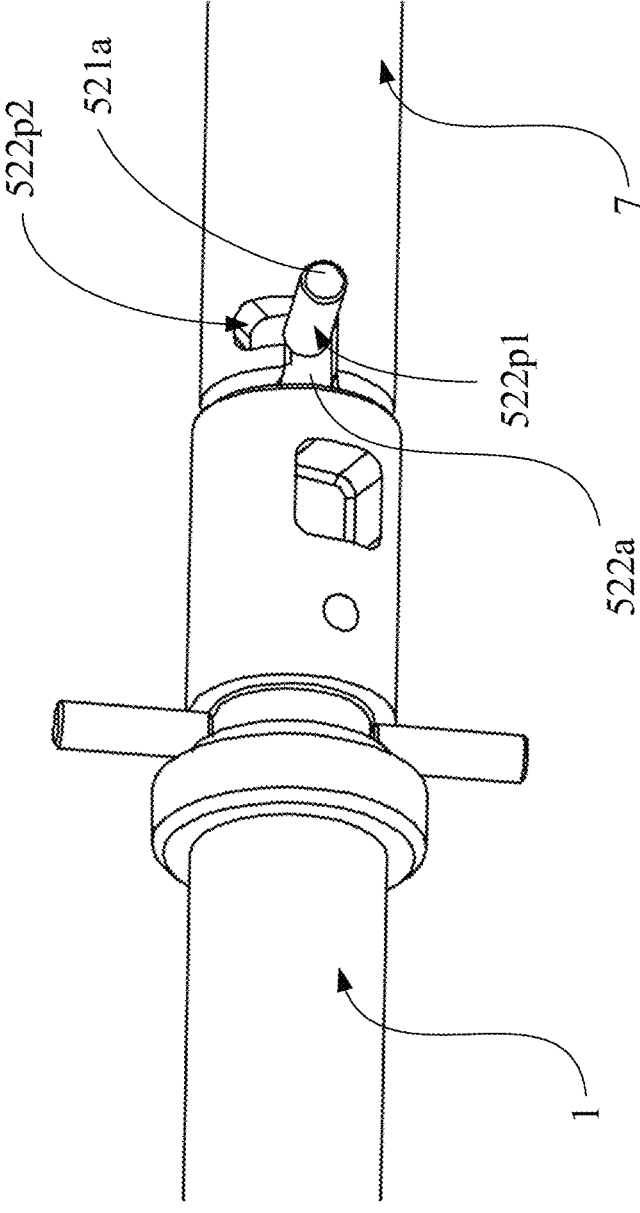

FIG. 13 is a structural schematic diagram of the engagement mechanism according to the embodiment of the present disclosure.

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present disclosure, are not intended to indicate any sequence, amount or importance, but distinguish various components. The terms "comprises," "comprising," "includes," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

Before the clip clamps a blood vessel, the clip needs to be conveyed to an end effector located at the front end of a clip applying mechanism, and then the clip is fired through operating a handle assembly. In a case where the clip has been conveyed into the end effector, if an operator finds that the clip is not suitable (e.g., a size or a shape of the clip, etc. is not suitable), it is necessary to remove the entire clip applying mechanism from the handle assembly, and then mount another clip applying mechanism with a suitable clip. During use of the clip applying apparatus, the size of the clip may need to be adjusted at any time, so the replaced clip applying mechanism may be mounted again. Because there is already a clip in the end effector of the replaced clip applying mechanism, when the clip applying mechanism is mounted to the handle assembly again, the handle assembly cannot recognize that there is already a clip in the end effector; in this situation, convey of another clip to the end effector will damage the end effector, so that the clip applying mechanism cannot be used again.

To this end, the embodiments of the present disclosure provide a clip applying mechanism of a clip applying apparatus and the clip applying apparatus including the clip applying mechanism, which at least aims to avoid damaging the end effector when replacing the clip applying mechanism.

For example, the clip applying mechanism of the clip applying apparatus provided by the embodiment of the present disclosure includes: a tube body, a main shaft, a clip-cartridge assembly, and a clip-pushing assembly. The tube body includes a head end and a tail end opposite to each other; the main shaft is arranged proximal to the tail end and at least portion of the main shaft is arranged in the tube body; the clip-cartridge assembly is configured to penetrate through the tube body and includes a clip cartridge arranged in the tube body and an end effector being configured to penetrate out of the head end; the clip cartridge is configured to be filled with a clip; at least portion of the clip-pushing assembly is arranged in the tube body; and the clip-pushing assembly is configured to be pushed by the main shaft toward the head end to convey the clip in the clip cartridge into the end effector. Further, the clip applying mechanism further includes: a main-shaft connecting member, a housing and a locking mechanism. The main-shaft connecting member is sleeved on the main shaft and connected with the main shaft; the main-shaft connecting member is configured to move in a same direction as the main shaft in an axial direction of the tube body; the housing is configured to accommodate the main shaft and the main-shaft connecting member; and the locking mechanism is arranged between the main-shaft connecting member and the housing. The locking mechanism, the main-shaft connecting member and the housing are configured such that: in a case that the clip is conveyed into the end effector, the main-shaft connecting member and the housing are locked with each other through the locking mechanism.

In the clip applying mechanism provided by the above-described embodiment of the present disclosure, by providing the main-shaft connecting member connected with the main shaft and providing the locking mechanism between the main-shaft connecting member and the housing, it is ensured that the main-shaft connecting member and the housing are locked through the locking mechanism when the clip is conveyed into the end effector. In this way, when the above-described clip applying mechanism is removed, because positions of the main-shaft connecting member and the main shaft relative to the housing are locked, the main-shaft connecting member and the main shaft cannot move in the axial direction of the tube body; and when the clip applying mechanism is used again, a next clip is prevented from being conveyed into the end effector to avoid damage to the end effector, which is favorable for long-term use of the clip applying mechanism.

Hereinafter, the present disclosure will be described through several specific embodiments. In order to keep the following description of the embodiments of the present disclosure clear and concise, detailed description of known functions and known components may be omitted. When any component according to the embodiments of the present disclosure appears in more than one diagram, the component may be represented by a same reference sign in each diagram.

Figure 1A:
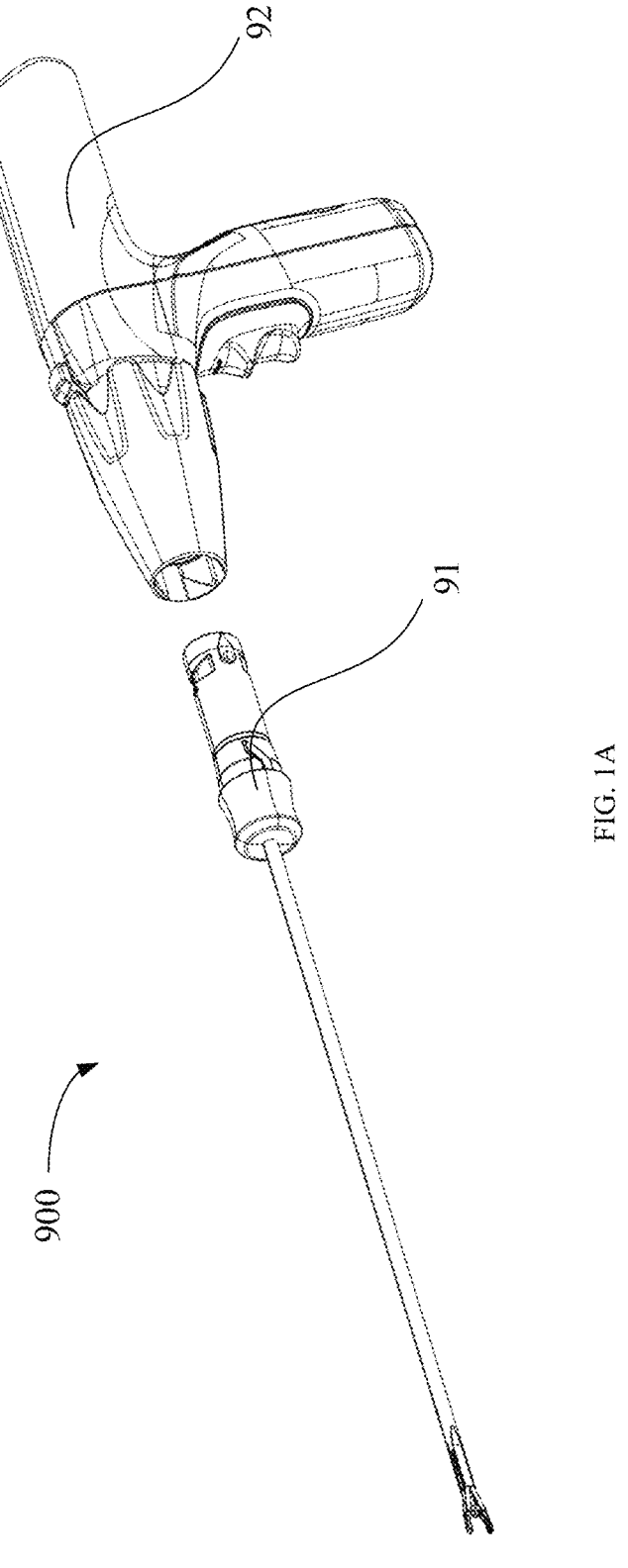
FIG. 1A and FIG. 1B are respectively schematic diagrams of two states of a clip applying apparatus according to an embodiment of the present disclosure.
Figure 1B:
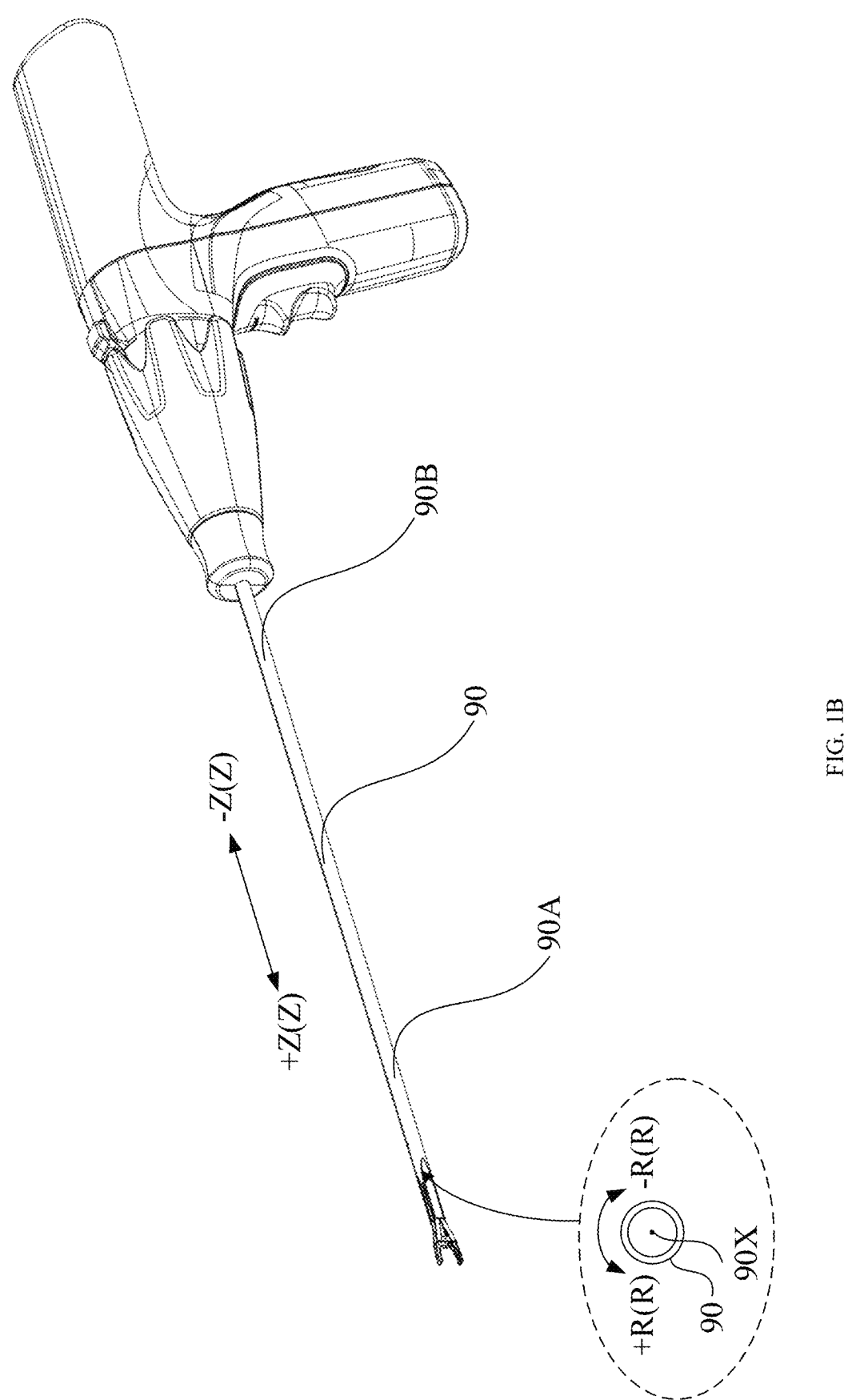
Figure 2:
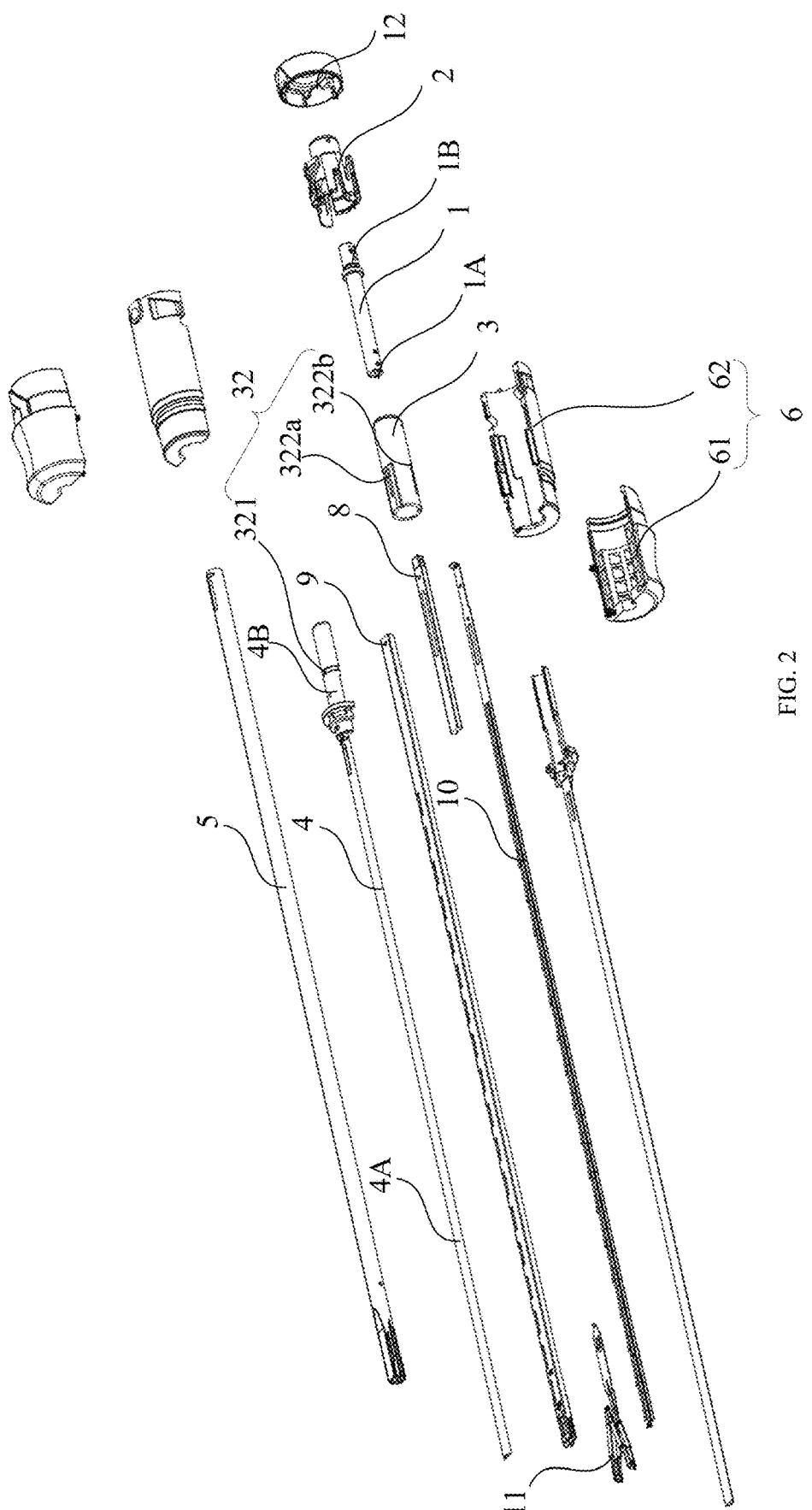
FIG. 2 is an exploded schematic diagram of a clip applying mechanism according to an embodiment of the present disclosure.
Figure 3:
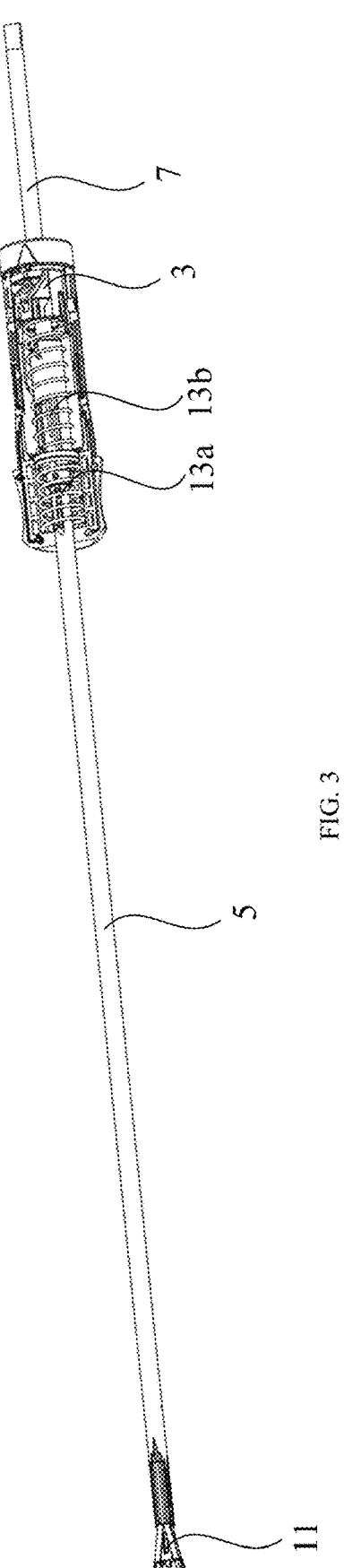
FIG. 3 is a structural schematic diagram of the clip applying mechanism in an initial state A according to the embodiment of the present disclosure.
Figure 3A:
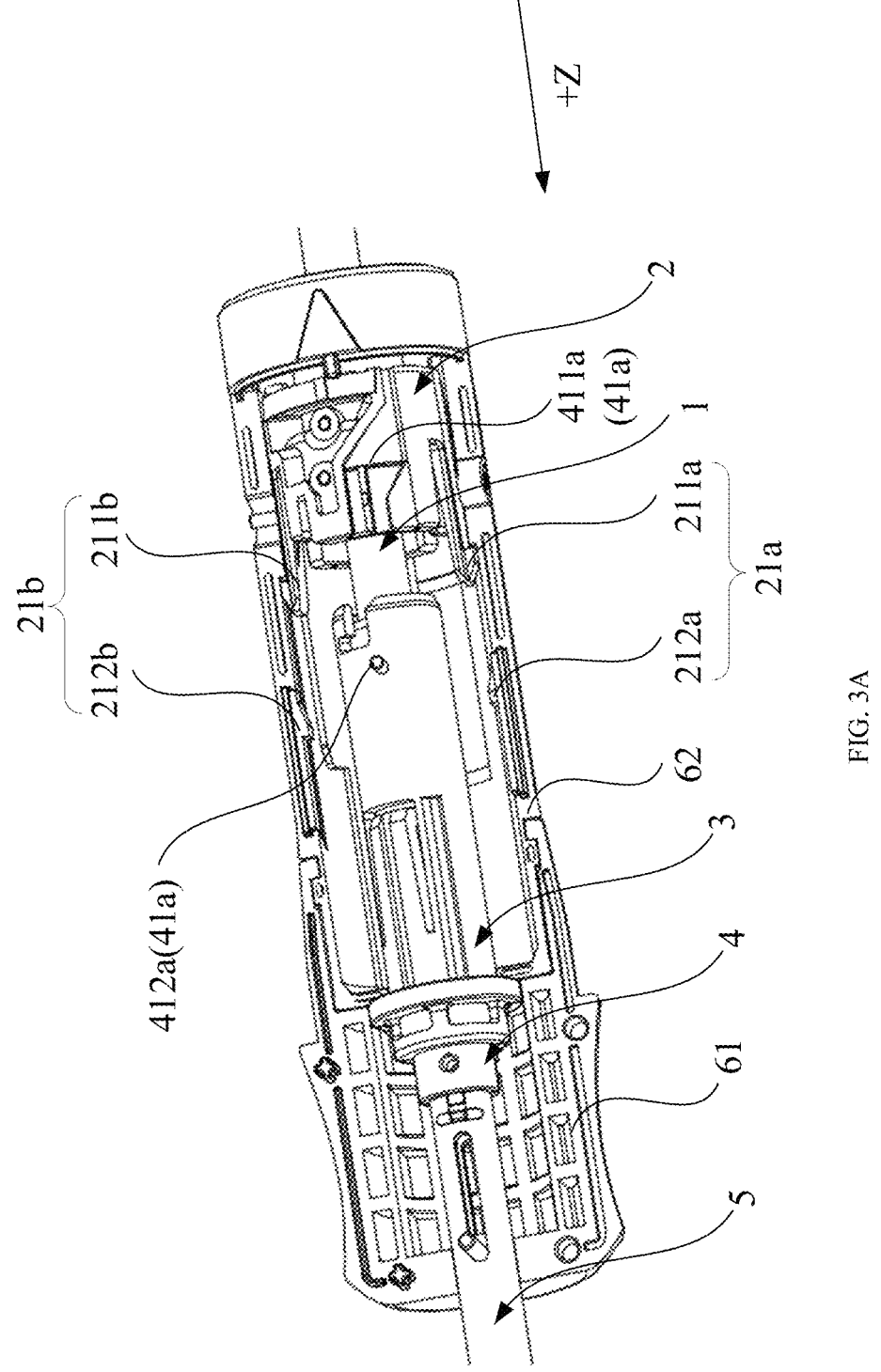
FIG. 3A is a first partial structural schematic diagram of the clip applying mechanism in the initial state A according to the embodiment of the present disclosure.
Figure 3B:
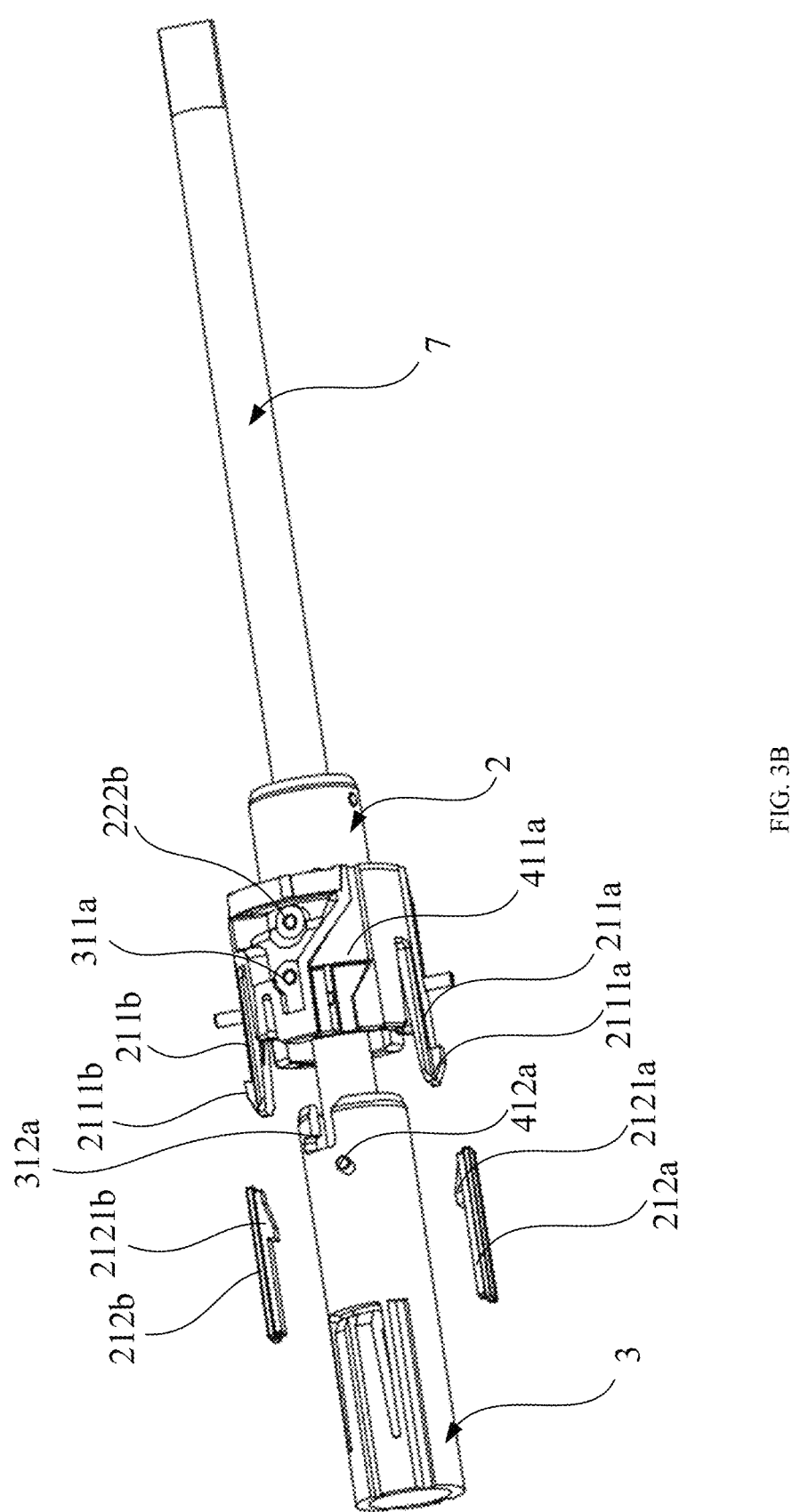
FIG. 3B is a second partial structural schematic diagram of the clip applying mechanism in the initial state A according to the embodiment of the present disclosure.
Figure 3C:
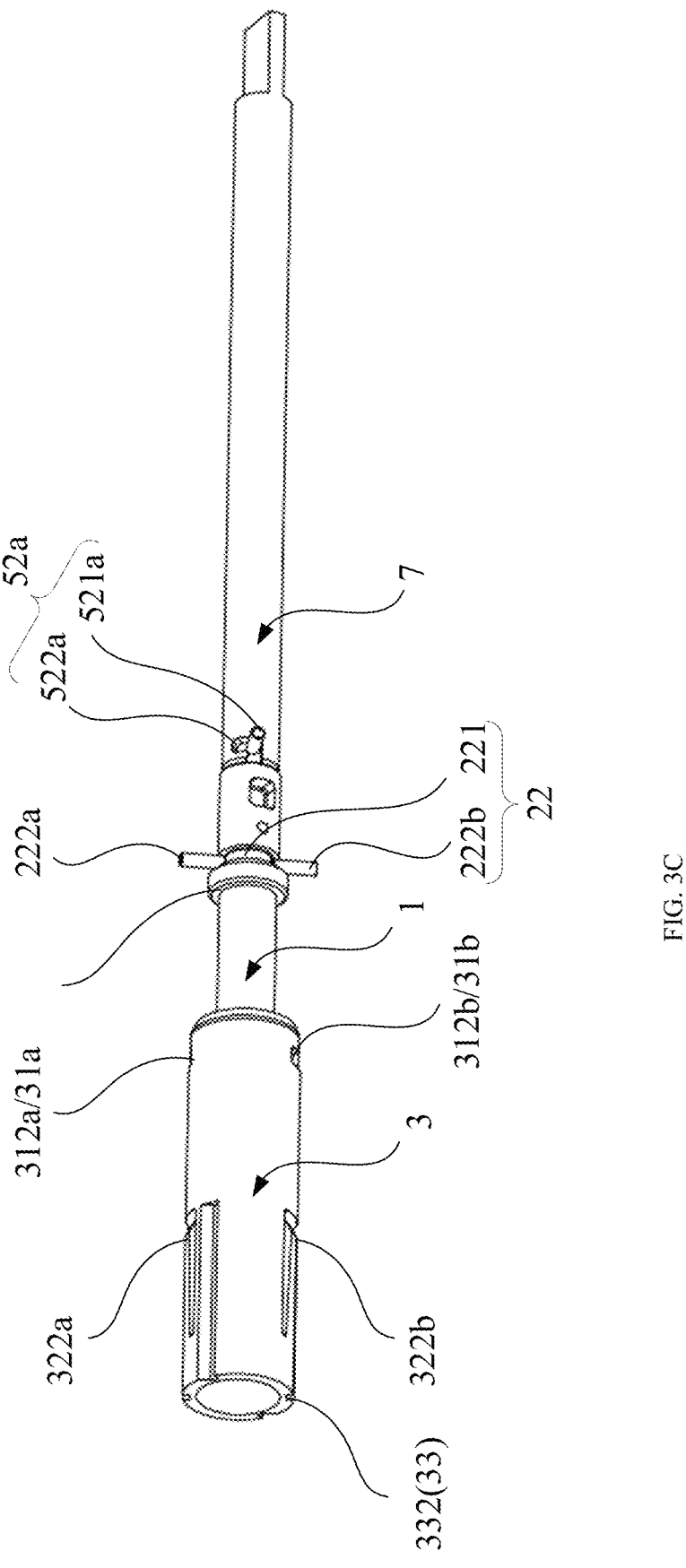
FIG. 3C is a third partial structural schematic diagram of the clip applying mechanism in the initial state A according to the embodiment of the present disclosure.

FIG. 1A and FIG. 1B are respectively schematic diagrams of two states of the clip applying apparatus according to the embodiment of the present disclosure. FIG. 2 is an exploded schematic diagram of the clip applying mechanism according to the embodiment of the present disclosure. FIG. 3 is a structural schematic diagram of the clip applying mechanism in an initial state according to the embodiment of the present disclosure. FIG. 3A is a first partial structural schematic diagram of the clip applying mechanism in the initial state according to the embodiment of the present disclosure. FIG. 3B is a second partial structural schematic diagram of the clip applying mechanism in the initial state according to the embodiment of the present disclosure. FIG. 3C is a third partial structural schematic diagram of the clip applying mechanism in the initial state according to the embodiment of the present disclosure.

As shown in FIG. 1A and FIG. 1B, a clip applying apparatus 900 provided by the embodiment of the present disclosure includes a clip applying mechanism 91 and a handle assembly 92. For example, the clip applying mechanism 91 is detachably connected with the handle assembly 92. When operating the clip applying apparatus 900, an operator may quickly remove the clip applying mechanism 91 from the handle assembly 92 or mount the clip applying mechanism 91 onto the handle assembly 92 according to actual needs.

The handle assembly 92 is configured to drive the clip applying mechanism 91 to control the clip applying mechanism to execute respective actions, including but not limited to, conveying the clip, firing the clip, resetting the firing assembly, resetting the clip-pushing assembly, and so on.

As shown in FIG. 1B, the clip applying mechanism 91 includes a tube body 90; and the tube body 90 includes a head end 90A and a tail end 90B opposite to each other. That is, in the axial direction Z of the tube body 90, the head end 90A is opposite to the tail end 90B; the head end 90A is a distal end that is distal to the handle assembly 92 or the operator, and the tail end 90B is a proximal end that is proximal to the handle assembly 92 or the operator.

According to the embodiment of the present disclosure, an extension direction of the tube body 90 is defined as the axial direction Z, as shown in FIG. 1B; the axial direction Z includes a +Z direction facing toward the head end 90A and a −Z direction facing away from the head end 90A. For example, according to the embodiment of the present disclosure, when a certain component or assembly moves in a direction facing toward the head end 90A, it may be understood that the component or assembly moves along the +Z direction; when a certain component or assembly moves away from the head end 90A, it may be understood that the component or assembly moves along the −Z direction.

According to the embodiment of the present disclosure, a circumferential direction of the tube body 90 refers to a direction in which the tube body 90 rotates around a rotation axis 90X thereof, as shown in FIG. 1B; the circumferential direction R includes a first rotation direction +R and a second rotation direction −R opposite to each other. For example, when viewing from the head end 90A to the tail end 90B, the first rotation direction +R is counterclockwise, and the second rotation direction −R is clockwise.

As shown in FIG. 2 and FIG. 3A, the clip applying mechanism 91 includes a main shaft 1, a main-shaft connecting member 2, a firing connecting member 3, a clip-cartridge assembly, a clip-pushing assembly, a firing assembly, a housing 6, a pushing rod 7, and an end cap 12. The firing assembly includes, for example, a firing rod 4 and a firing sleeve 5. The clip-cartridge assembly includes, for example, a clip cartridge 9 and a clamp 11 (the clamp 11 is also referred to as an end effector). The clip-pushing assembly includes, for example, a pushing block 8 and a clip pushing piece 10.

In at least some embodiments, the tube body 90 has a cavity; and at least portions of the main shaft 1, the clip-cartridge assembly, the clip-pushing assembly, and the firing assembly are arranged in the tube body 90.

For example, the main shaft 1 is arranged proximal to the tail end 90B of the tube body 90 and at least portion of the main shaft 1 is arranged in the tube body 90. For example, the main shaft 1 includes a first end portion 1A and a second end portion 1B opposite to each other; in the axial direction Z, the first end portion 1A is proximal to the head end 90A, and the second end portion 1B is distal to the head end 90A. During operation of the clip applying mechanism, the first end portion 1A is located in the tube body 90.

For example, the clip-cartridge assembly penetrates through the tube body 90. The clip cartridge 9 is arranged in the tube body 90 and is used for loading a plurality of clips. The clamp 11 penetrates out of the head end 90A. In one example, the plurality of clips are arranged in the clip cartridge 9 along the axial direction Z.

For example, at least portion of the clip-pushing assembly is arranged in the tube body 90; and the clip-pushing assembly is configured to be pushed by the main shaft 1 toward the head end 90A to convey the clip in the clip cartridge 9 into the clamp 11. In one example, the pushing block 8 moves in a direction facing toward the head end 90A and drive the clip pushing piece 10 to push the clips in the clip cartridge 9 into the clamp 11 one by one.

For example, at least portion of the firing assembly is located in the tube body 90; and the firing assembly is configured to be pushed by the main shaft 1 toward the head end 90A to close the clamp 11, so that the clip in the clamp 11 is fired.

For example, the firing sleeve 5 is used as the tube body 90, and the clamp 11 penetrates out of a head end of the firing sleeve 5. When the firing sleeve 5 moves along the +Z direction, the firing sleeve 5 enables two clamp arms of the clamp 11 to move proximal to each other, so that the clamp 11 is in a closed state, and in this situation, the clip is fired. When the firing sleeve 5 moves along the −Z direction, the two clamp arms of the clamp 11 move away from each other, so that the clamp 11 in an open state, waiting for subsequent clip convey.

As shown in FIG. 3B and FIG. 3C, the main-shaft connecting member 2 is sleeved on the main shaft 1 and connected with the main shaft 1; the main-shaft connecting member 2 is configured to move in a same direction as the main shaft 1 in the axial direction Z. For example, the main-shaft connecting member 2 is sleeved on the second end portion 1B of the main shaft 1 and connected with the second end portion 1B; and when the main shaft 1 moves along the +Z or −Z direction, the main-shaft connecting member 2 also moves along the +Z or −Z direction with the main shaft 1.

As shown in FIG. 3B and FIG. 3C, for example, the clip applying mechanism 91 further includes an axial engagement mechanism 22, which is arranged between the main shaft 1 and the main-shaft connecting member 2. In one example, the axial engagement mechanism 22 includes a slot 221 arranged on the main shaft 1 as well as pins 222a, 222b arranged on the main-shaft connecting member 2; and the pins 222a, 222b are configured to move in the slot 221 along the circumferential direction of the main shaft 1.

In this way, the main shaft 1 and the main-shaft connecting member 2 are engaged and connected with each other in the axial direction of the main shaft 1 by using the axial engagement mechanism 22, so that the main shaft 1 and the main-shaft connecting member 2 moves simultaneously in a same direction of the axial direction Z on one hand, and on the other hand, one of the main shaft 1 and the main-shaft connecting member 2 moves relative to the other in the circumferential direction of the main shaft 1, for example, the main shaft 1 and the main-shaft connecting member 2 rotates relative to each other.

For example, the slot 221 is an annular slot extending along the circumferential direction of the main shaft 1, so that the pins 222a and 222b rotate in the slot 221 by 360 degrees. In one example, when the main shaft 1 rotates within the main-shaft connecting member 2, rotation of the clamp 11 may be controlled, thereby increasing flexibility of a rotation angle of the clamp 11.

The embodiments of the present disclosure are described by taking the two pins 222a and 222b as an example; and it may be understood that the number of pins may be one or more than two, for example, three, etc., which will not be limited in the embodiments of the present disclosure.

When the number of pins is plural, the plurality of pins are arranged at equal interval in the circumferential direction of the main shaft 1, rendering a uniform force on the main shaft 1 or the main-shaft connecting member 2, thereby avoiding damage to the main shaft 1 or the main-shaft connecting member 2 caused by the clip applying mechanism during operation.

For example, as shown in FIG. 3C, the two pins 222a and 222b are arranged symmetrically in a radial direction of the main shaft 1, which reduces the number of pins as much as possible, save fabrication costs, and reduce manufacturing difficulty, under the condition of ensuring a uniform force on the main shaft 1 or the main-shaft connecting member 2.

Figure 3D:
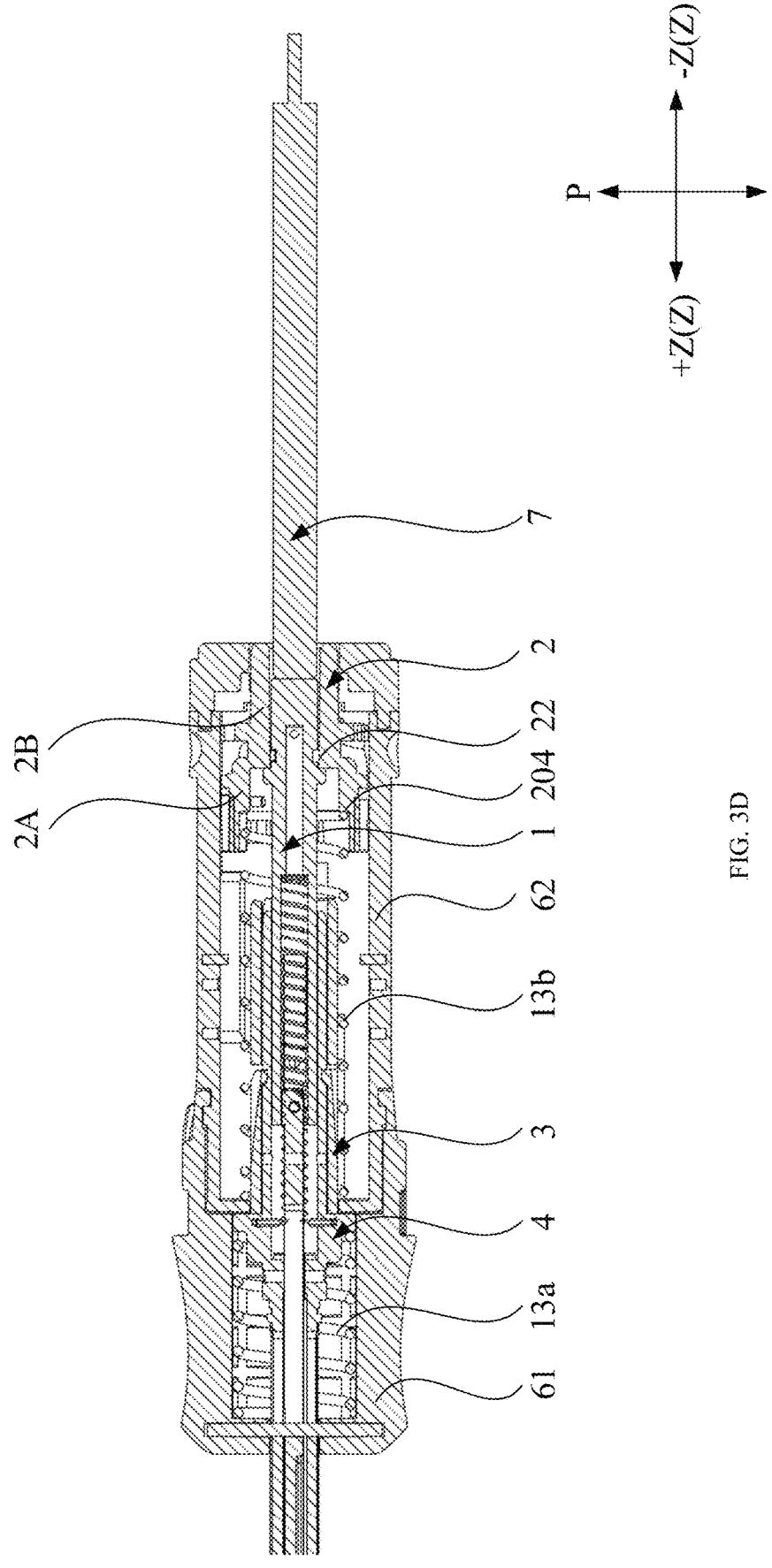
FIG. 3D is a cross-sectional schematic diagram of the clip applying mechanism in the initial state A according to the embodiment of the present disclosure.

According to the embodiment of the present disclosure, the main shaft 1 and the tube body 90 are arranged parallel to each other, so the axial direction Z of the tube body 90 may be referred to for the axial direction of the main shaft 1, the circumferential direction R of the tube body 90 may be referred to for the circumferential direction of the main shaft 1, and a radial direction P of the tube body 90 shown in FIG. 3D may be referred to for the radial direction of the main shaft 1.

FIG. 3D is a cross-sectional schematic diagram of the clip applying mechanism in the initial state according to the embodiment of the present disclosure. Referring to FIG. 2, FIG. 3 and FIG. 3D, the housing 6 is arranged at the tail end 90B of the tube body 90, and is configured to accommodate the main shaft 1 and the main-shaft connecting member 2. That is, the main shaft 1 and the main-shaft connecting member 2 are arranged in the housing 6. The main shaft 1 and the main-shaft connecting member 2 may move in the axial direction Z or rotate in the circumferential direction R within the housing 6.

As shown in FIG. 2, the main-shaft connecting member 2 is located between the main shaft 1 and the housing 6 in the radial direction P of the main shaft 1. For example, the housing 6 includes a first housing portion 61 and a second housing portion 62 connected with the first housing portion 61 in the axial direction Z; the first housing portion 61 is proximal to the head end 90A; and the second housing portion 62 is distal to the head end 90A. The first housing portion 61 is configured to be capable of rotating in the circumferential direction R relative to the second housing portion 62. For example, the first housing portion 61 is fixedly connected with the clip-pushing assembly and the firing assembly, and the operator may adjust a rotation angle of the clip feeding assembly and the firing assembly by rotating the first housing portion 61. The second housing portion 62 keeps fixed relative to the main-shaft connecting member 2, which is favorable for implementing locking between the second housing portion 62 and the main-shaft connecting member 2.

In at least some embodiments, locking mechanisms 21a, 21b are arranged between the main-shaft connecting member 2 and the housing 6. For example, as shown in FIG. 3A and FIG. 3B, the locking mechanisms 21a, 21b are arranged between the main-shaft connecting member 2 and the second housing portion 62. When the clip is conveyed into the clamp 11, the main-shaft connecting member 2 and the second housing portion 62 are locked with each other through the locking mechanisms 21a, 21b. That is, in the axial direction Z and the circumferential direction R, the main-shaft connecting member 2 and the second housing portion 62 keep fixed to each other, so that the main shaft 1 and the main-shaft connecting member 2 cannot move in the Z direction.

In at least some embodiments, the locking mechanisms 21a, 21b include first locking members 211a, 211b arranged on the main-shaft connecting member 2 and second locking members 212a, 212b arranged on the housing 6. For example, as shown in FIG. 3A and FIG. 3B, the locking mechanism 21a includes a first locking member 211a arranged on the main-shaft connecting member 2 and a second locking member 212a arranged on the second housing portion 62; the locking mechanism 21b includes a first locking member 211b arranged on the main-shaft connecting member 2 and a second locking member 212b arranged on the second housing portion 62. The first locking member 211a and the second locking member 212a are configured such that: when the main shaft 1 and the main-shaft connecting member 2 move along the +Z direction to push the clip-pushing assembly to convey the clip into the clamp 11, the first locking member 211a and the second locking member 212a are locked with each other, and the first locking member 211b and the second locking member 212b are locked with each other.

During use of the clip applying apparatus, different types of clips may be required. For example, when the operator finds that the size of the clip in the clamp 11 is not suitable, he/she needs to remove the clip applying mechanism 91 from the handle assembly 92 and mount another clip applying mechanism with a clip of a suitable size. When the clip applying mechanism 91 is mounted onto the handle assembly 92 again, since the handle assembly 92 cannot recognize that there is already a clip in the clamp 11, it will convey the clip in the clip cartridge 9 into the clamp 11 again, causing damage to the clamp 11 and affecting secondary use of the clip applying mechanism.

According to the embodiment of the present disclosure, by using the locking mechanisms 21a, 21b arranged between the main-shaft connecting member 2 and the housing 6, the main shaft 1 and the main-shaft connecting member 2 keep fixed in the axial direction Z of the tube body 90 relative to the housing 6 when the clip is conveyed into the clamp 11, which, on one hand, prevents the main shaft 1 from driving the clip-pushing assembly to continue to convey the clip to the clamp 11, on the other hand, avoids accidental situations such as error firing due to movement of the main shaft 1 or the main-shaft connecting member during the removing process, thereby increasing safety of operation.

As shown in FIG. 2, the main shaft 1 includes the first end portion 1A and the second end portion 1B opposite to each other; in the axial direction Z of the tube body 90, the first end portion 1A is proximal to the head end 90A, and the second end portion 1B is distal to the head end 90A.

Figure 4B:
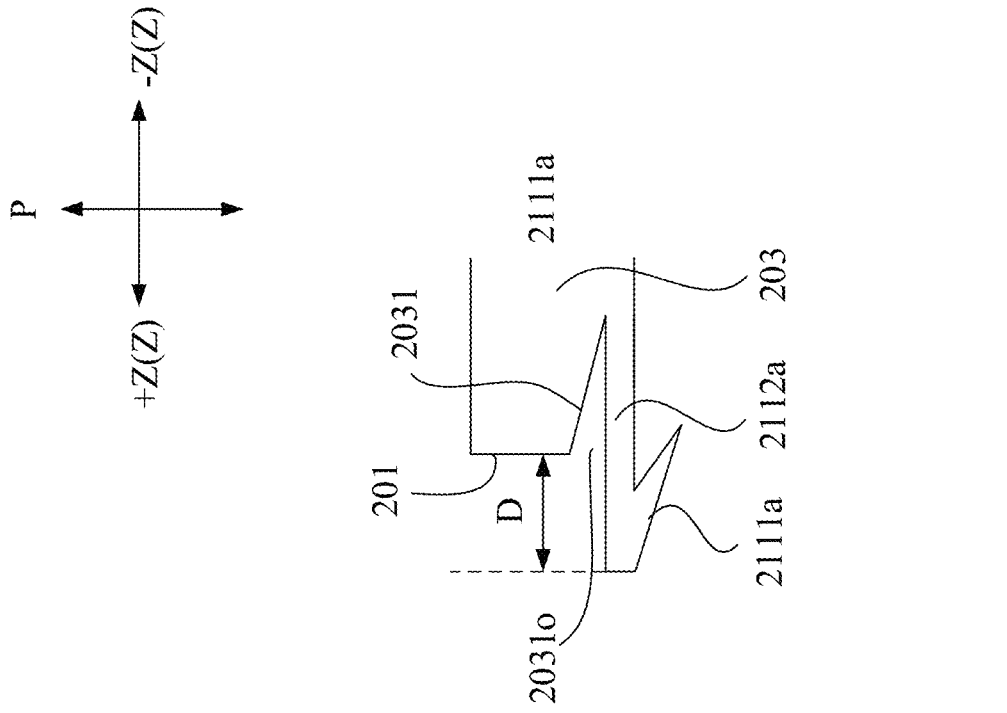
FIG. 4B is a partial structural schematic diagram of the main-shaft connecting member according to the embodiment of the present disclosure.
Figure 4A:
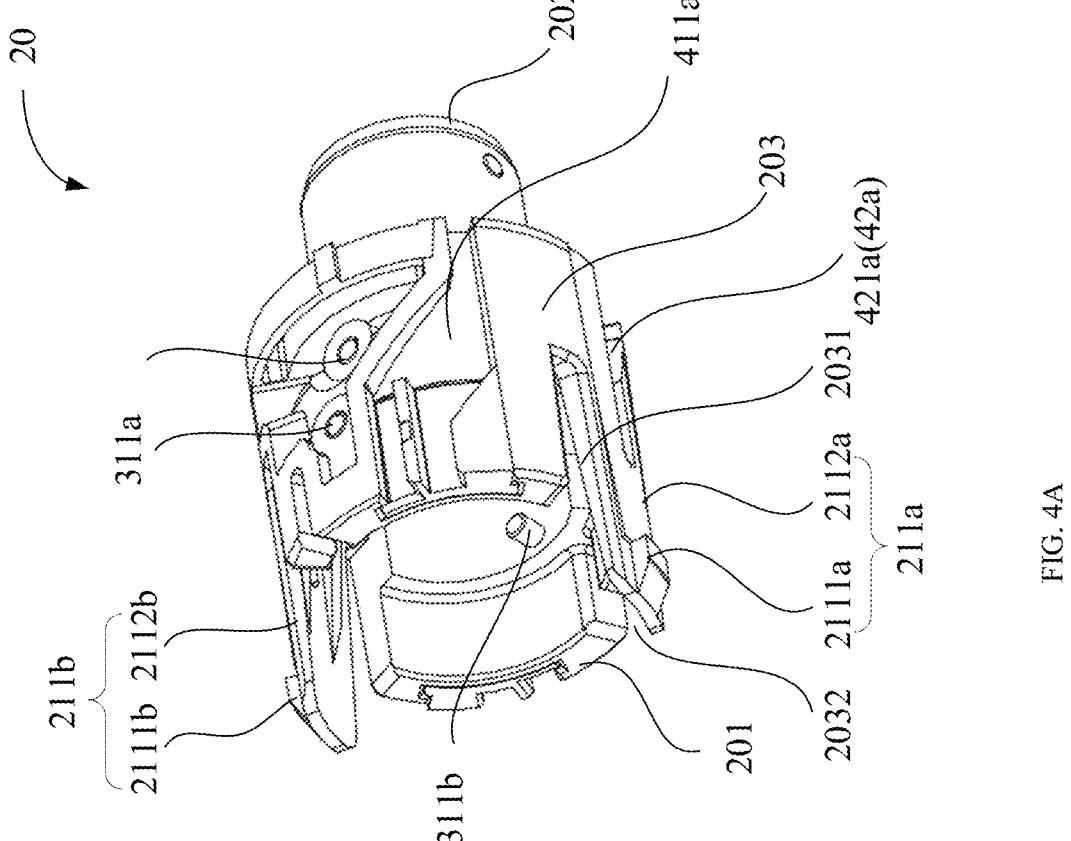
FIG. 4A is a first structural schematic diagram of a main-shaft connecting member according to the embodiment of the present disclosure.
Figures 4C, 4D:
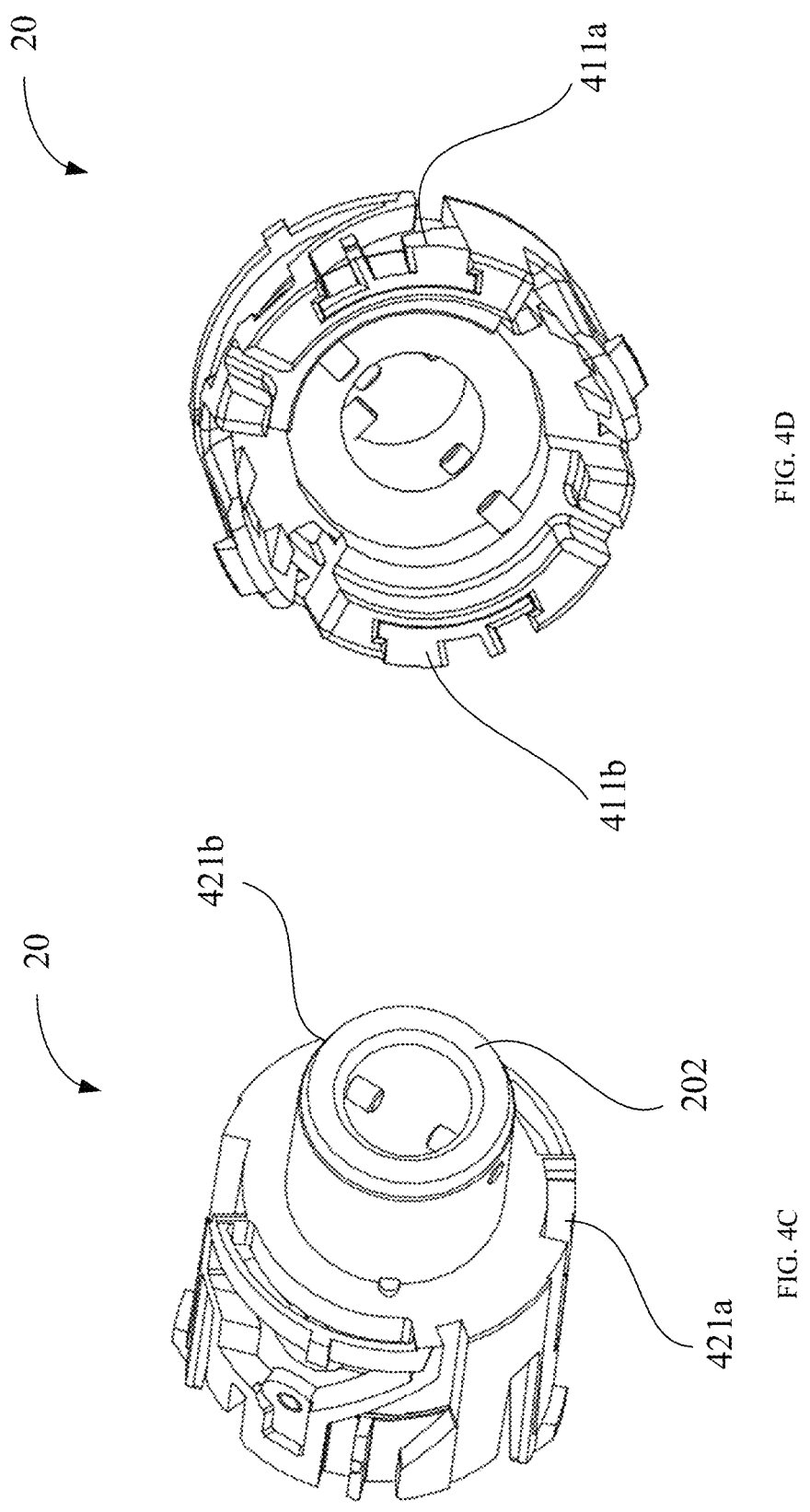
FIG. 4C is a second structural schematic diagram of the main-shaft connecting member according to the embodiment of the present disclosure.
FIG. 4D is a third structural schematic diagram of the main-shaft connecting member according to the embodiment of the present disclosure.

FIG. 4A is a first structural schematic diagram of the main-shaft connecting member according to the embodiment of the present disclosure; FIG. 4B shows a partial structural schematic diagram of the main-shaft connecting member according to the embodiment of the present disclosure; FIG. 4C is a second structural schematic diagram of the main-shaft connecting member according to the embodiment of the present disclosure; and FIG. 4D is a third structural schematic diagram of the main-shaft connecting member according to the embodiment of the present disclosure.

As shown in FIG. 2, the main-shaft connecting member 2 is a tubular member 20, and at least portion of the tubular member 20 is sleeved on the second end portion 1B of the main shaft 1. As shown in FIG. 3D, the tubular member 20 has a cavity, the main shaft 1 is arranged in the cavity, and the axial engagement mechanism 22 is arranged in the tubular member 20, so that the main shaft 1 and the main-shaft connecting member 2 are engaged with each other in the Z direction.

According to the embodiment of the present disclosure, the tubular member 20 (i.e., the main-shaft connecting member 2) is arranged parallel to the tube body 90, so the axial direction Z of the tube body 90 may be referred to for the extension direction or the axial direction of the tubular member 20; the circumferential direction R of the tube body 90 may be referred to for the circumferential direction of the tubular member 20; and the radial direction P of the tube body 90 may be referred to for the radial direction of the tubular member 20.

As shown in FIG. 4A, for example, the tubular member 20 includes a tube wall 203; and the tube wall 203 defines a cavity of the tubular member 20. The tube wall 203 includes a first end face 201 and a second end face 202 opposite to each other in the extension direction of the tubular member 20; the first end face 201 is proximal to the head end 90A, and the second end face 202 is distal to the head end 90A.

For example, the first locking member 211a includes a protruding portion 2112a extending from the first end face 201 of the tube wall 203 toward the head end 90A and a first hook 2111a arranged on the protruding portion 2112a; the first locking member 211b includes a protruding portion 2112b extending from the first end face 201 of the tube wall 203 toward the head end 90A and a first hook 2111b arranged on the protruding portion 2112b.

In at least some embodiments, the housing 6 includes an inner wall facing toward the main-shaft connecting member 2; the second locking member includes a second hook arranged on the inner wall; and the first hook and the second hook are configured to be engaged with each other.

Figure 5:
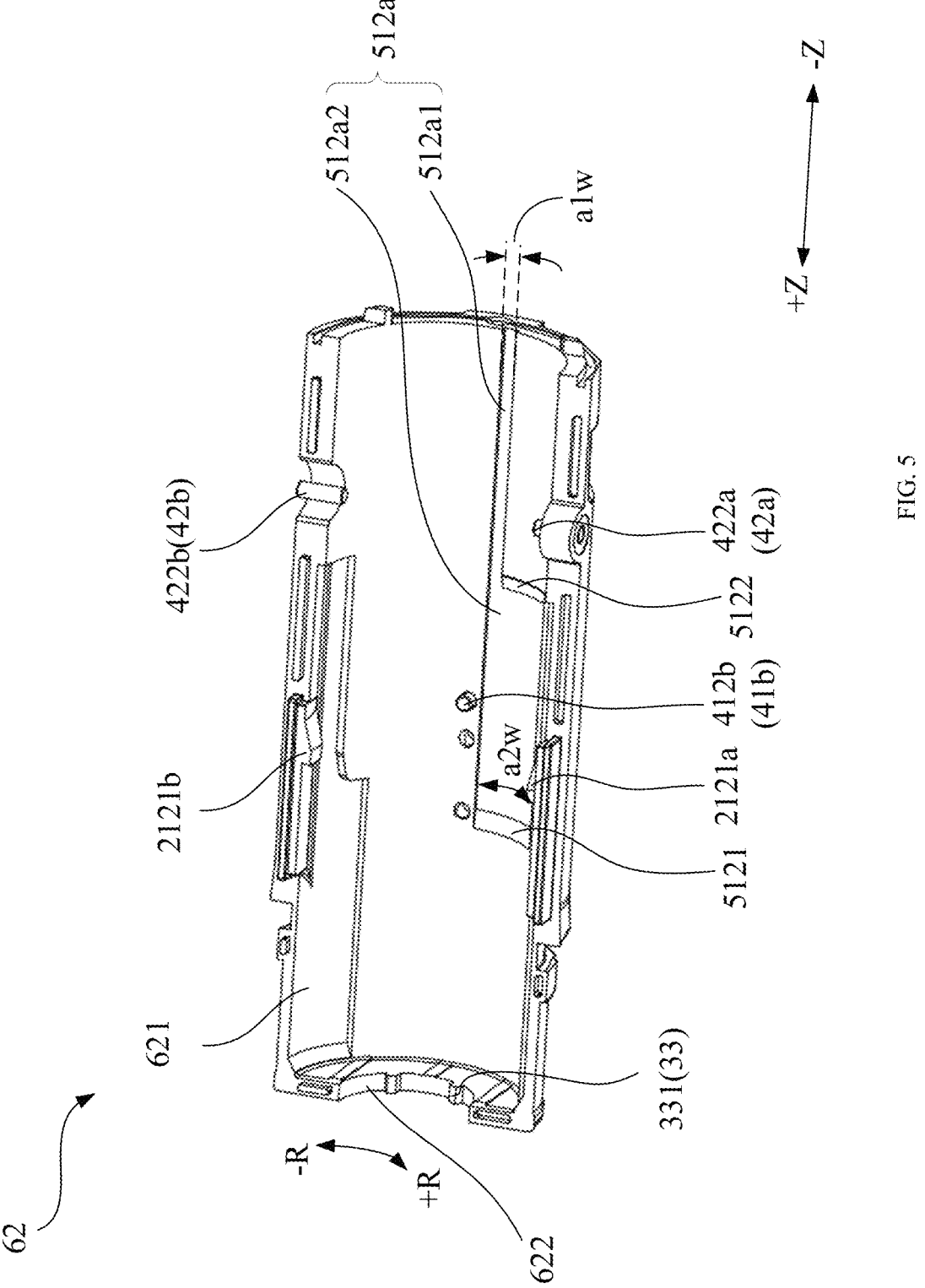
FIG. 5 is a partial structural schematic diagram of a second housing portion according to the embodiment of the present disclosure.

FIG. 5 is a partial structural schematic diagram of the second housing portion according to the embodiment of the present disclosure. As shown in FIG. 3B and FIG. 5, for example, the second housing portion 62 is substantially cylindrical and includes an inner wall 621 facing toward the main-shaft connecting member 2. For example, the second locking member 212a includes a second hook 2121a arranged on the inner wall 621; and the second locking member 212b includes a second hook 2121b arranged on the inner wall 621. The first hook 2111a and the second hook 2121a are configured to be engaged with each other; and the first hook 2111b and the second hook 2121b are configured to be engaged with each other.

In this way, mutual locking between the first locking member 211a and the second locking member 212a is implemented by mutual engagement between the first hook 2111a and the second hook 2121a, and mutual locking between the first locking member 211b and the second locking member 212b is implemented by mutual engagement between the first hook 2111b and the second hook 2121b.

According to the embodiment of the present disclosure, the first hooks 2111a, 2111b are arranged on the protruding portions 2112a, 2112b extending from the first end face 201, which is more favorable during the rebound of the protruding portions 2112a, 2112b in the radial direction of the tubular member 20, so that the first hooks 2111a, 2111b are more easily engaged with the second hooks 2121a, 2121b.

As shown in FIG. 4A, the first hook 2111a is taken as an example. If the first hook 2111a is directly arranged on the first end face 201 (rather than being arranged on the protruding portion 2112a), in a case where the first hook 2111a and the second hook 2121a in FIG. 3B are to be engaged with each other, a great force is required to push the main-shaft connecting member 2 so that the first hook 2111a and the second hook 2121a are engaged with each other, because the first hook 2111a has no rebound space. However, according to the embodiment of the present disclosure, because the protruding portion 2112a is extend from the first end face of the tube wall 203, the protruding portion 2112a is no longer limited by the tube wall 203 and has certain rebound space, thereby reducing resistance force when the first hook 2111a and the second hook 2121a are engaged with each other.

FIG. 4B shows positional relationships among the first end face 201, the first hook 2111a and the protruding portion 2112a of the tube wall 203. As shown in FIG. 4B, a distance between a terminal end of the protruding portion 2112a and the first end face 201 in the Z direction is defined as D, and a total length of the tubular member 20 in the Z direction thereof is defined as L (not shown), where L is 4 to 12 times of D. With the above-described parameter settings, space occupied by the main-shaft connecting member 2 in the housing is be reduced as much as possible to make the clip applying mechanism more compact, under the condition of ensuring that the first hook and the second hook are more easily engaged with each other. For example, L is 25 mm to 35 mm, D is 3 mm to 6 mm; and preferably, L is approximately 30 mm and D is 4 to 6 mm.

For example, as shown in FIG. 4A, the tubular member 20 further includes two through slots 2031, 2032 arranged in the tube wall 203. The two through slots 2031, 2032 extend substantially along the Z direction, so an extension direction of the two through slots 2031, 2032 is parallel to the Z direction.

According to the embodiment of the present disclosure, the two through slots 2031, 2032 may have a same shape or different shapes. In the case that the two have the same shape, the fabrication process may be simplified, which, thus, is preferred. The embodiments of the present disclosure are illustrated by taking that the two have the same shape as an example.

For example, taking the through slot 2031 in FIG. 4B as an example, the through slot 2031 includes a notch 2031o provided on the first end face 201. The notch 2031o is connected with the protruding portion 2112a, that is, in the circumferential direction of the tubular member 20, the notch 2031o and the protruding portion 2112a are adjacent to each other.

In conjunction with FIG. 3B and FIG. 4A, in a case where the first hook 2111a approaches the second hook 2121a to be engaged with the second hook 2121a, the protruding portion 2112a moves in the radial direction P of the tubular member 20 (i.e., rebound occurs). According to the embodiment of the present disclosure, by arranging the notch 2031o and the protruding portion 2112a adjacent to each other, a movement range or rebound space of the protruding portion 2112a is increased, thereby further reducing resistance force when the first hook 2111a and the second hook 2121a are engaged with each other.

As shown in FIG. 4A, in the circumferential direction of the tubular member 20, the two through slots 2031, 2032 are respectively arranged on two opposite sides of the protruding portion 2112a, so that the two notches of the two through slots 2031, 2032 are respectively arranged on two opposite sides of the protruding portion 2112a and are adjacent to the protruding portion 2112a. Similarly, the protruding portion 2112b is also provided with two through slots on two opposite sides of the protruding portion 2112b in the circumferential direction of the tubular member 20, and no details will be repeated here.

In at least some examples, the clip applying mechanism 91 further includes a reset member for resetting the clip applying mechanism 91, for example, the reset member is arranged in the housing. Referring to FIG. 3 and FIG. 3D, for example, the clip applying mechanism 91 includes a first spring 13a (i.e., a first reset member) arranged in the first housing portion 61 and a second spring 13b (i.e., a second reset member) arranged in the second housing portion 62.

As shown in FIG. 3D, for example, the first spring 13a is sleeved on the firing rod 4, abuts between the first housing portion 61 and the firing rod 4, and is used for resetting the firing assembly.

As shown in FIG. 3D, for example, the second spring 13b is sleeved on the firing connecting member 3, abuts between the second housing portion 62 and the main-shaft connecting member 2, and is used for resetting the clip-pushing assembly, the main shaft 1 and the main-shaft connecting member 2. For example, the main-shaft connecting member 2 is provided therein with a step portion 204, and the second spring 13b abuts between an inner surface of the second housing portion 62 and the step portion 204 of the main-shaft connecting member 2.

In a case where the clip applying mechanism 91 executes respective actions, the clip applying mechanism has a plurality of different operation states. To facilitate understanding, the clip applying mechanism 91 according to the embodiment of the present disclosure is set to have states below:

1) Initial state A: applying no external force to the main shaft 1 and the main-shaft connecting member 2;
2) Clip feeding completion state B: applying an external force, so that the main shaft 1 and the main-shaft connecting member 2 move along the +Z direction; herein, the main shaft 1 pushes the clip-pushing assembly so that the clip is conveyed into the clamp 11;
3) Adjustment state C: continuing to apply an external force, so that the main shaft 1 and the main-shaft connecting member 2 continue to move along the +Z direction, herein, the main shaft 1 pushes the firing assembly to adjust an open-close angle of the clamp 11;
4) Firing completion state D: continuing to apply an external force, so that the main shaft 1 and the main-shaft connecting member 2 continue to move along the +Z direction, so as to fire the clip in the clamp 11; herein, the main-shaft connecting member 2 simultaneously rotates along the first rotation direction R during the movement of the main-shaft connecting member 2;
5) Retreat state E: applying an external force, so that the main shaft 1 and the main-shaft connecting member 2 move along the −Z direction; herein, the main-shaft connecting member 2 drives the firing assembly to move in the −Z direction during the movement of the main-shaft connecting member 2;
6) Gyration state F: under an action of the first reset member, the main shaft 1 and the main-shaft connecting member 2 moving along the −Z direction; herein, the main-shaft connecting member 2 simultaneously gyrates along the second rotation direction −R during the movement of the main-shaft connecting member 2, and the firing assembly is reset;
7) Returning to the initial state G: under an action of the second reset member, the main shaft 1 and the main-shaft connecting member 2 continuing to move along the −Z direction; herein, the main-shaft connecting member 2 simultaneously gyrates along the second rotation direction −R during the movement of the main-shaft connecting member 2, so that the clip-pushing assembly, the main shaft 1 and the main-shaft connecting member 2 are all reset.

According to the embodiment of the present disclosure, the term "external force" refers to a force not generated by a component per se, which may refer to a force from outside the clip applying mechanism (e.g., a driving force provided by the handle assembly or a force directly applied to the clip applying mechanism by the operator), or may also refer to a force generated by other component in the clip applying mechanism. For example, in a case where the main-shaft connecting member 2 is applied with an external force, the force may be a pushing force from the pushing rod 7, or may also be a driving force generated due to movement of the main shaft 1, or may also be a reset force generated by the reset member.

According to the embodiment of the present disclosure, the adjustment state C is an optional state. That is, the clip applying mechanism 91 may or may not have the adjustment state C. In some cases, whether the clip applying mechanism 91 has an adjustment state may be determined according to a rebound performance of the clip.

In some embodiments, in a case where the rebound performance of the clip is good, the clip applying mechanism 91 may have the above-described adjustment state C. For example, a width of the clip in the clamp 11 is larger than a diameter of a puncture device (the puncture device is, for example, a circular tube having a diameter), the open-close angle of the clamp 11 is reduced through the adjustment state C, thereby reducing the width of the clip and making it easier for the clip applying mechanism 91 to pass through the puncture device. In one example, the clip in the clamp 11 is a plastic clip with a width of about 17.5 mm, and the diameter of the puncture device is approximately 10 mm. Through the above-described adjustment state C, the width of the clip is reduced from 17.5 mm to about 10 mm, so that the clamp 11 of the clip applying mechanism 91 smoothly passes through the puncture device.

In other embodiments, in a case where the rebound performance of the clip is poor, the clip applying mechanism 91 may not have the above-described adjustment state C. For example, the clip is a metal clip with low elasticity; if the open-close angle of the clamp 11 is reduced, the metal clip cannot rebound, resulting in that the metal clip cannot be used normally. In one example, a width of the metal clip is approximately 5.6 mm, with this width, the clip is ensured to pass through the puncture device smoothly, there is no need to adjust the open-close angle of the clamp 11.

In order to describe each state of the clip applying mechanism in detail, the embodiment of the present disclosure is illustrated by taking that the clip applying mechanism 91 has the adjustment state C as an example.

As described above, the clip applying mechanism 91 in FIG. 3 to FIG. 3D is in the initial state A.

Figure 6:
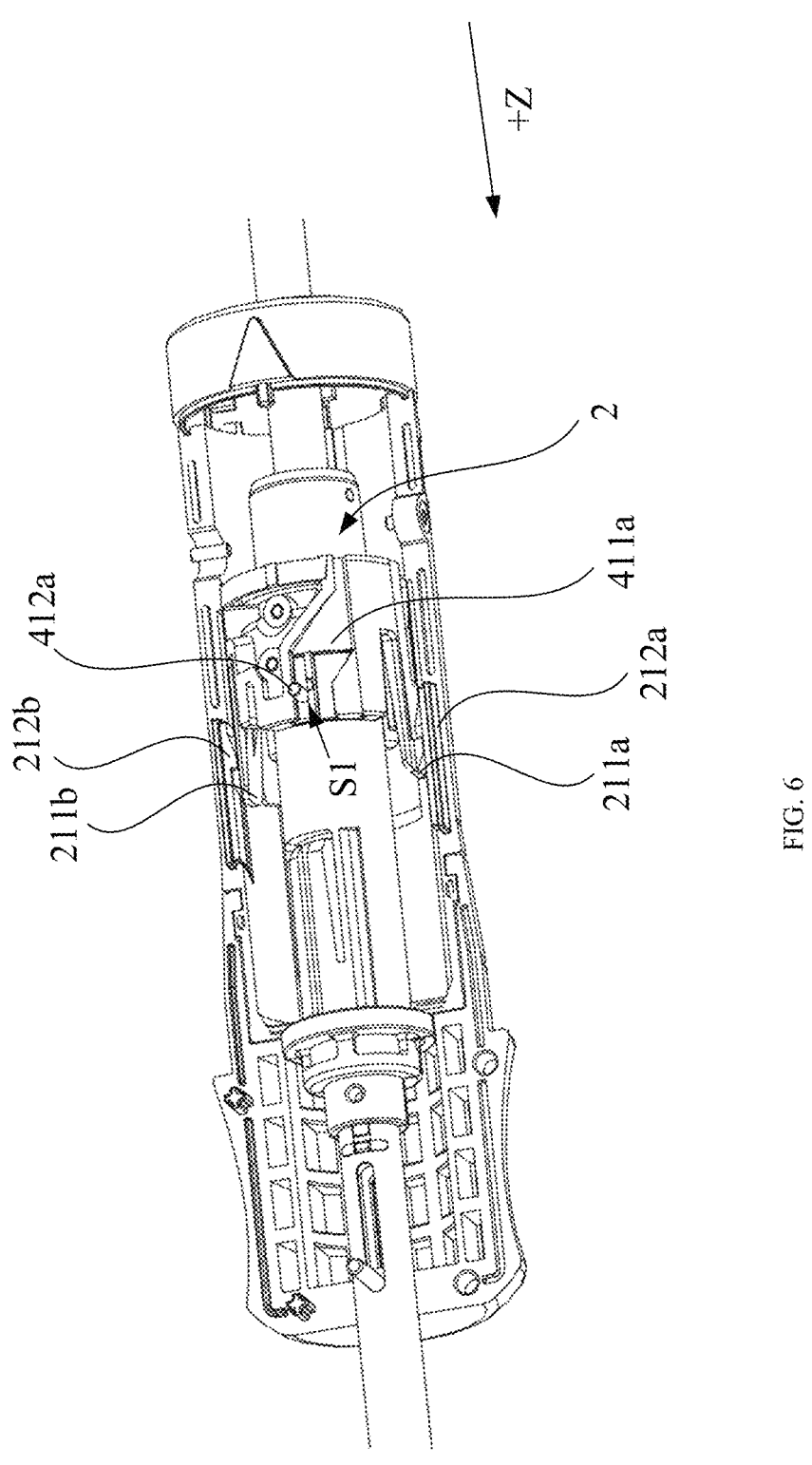
FIG. 6 is a partial structural schematic diagram of the clip applying mechanism in a clip feeding completion state B according to the embodiment of the present disclosure.
Figure 7A:
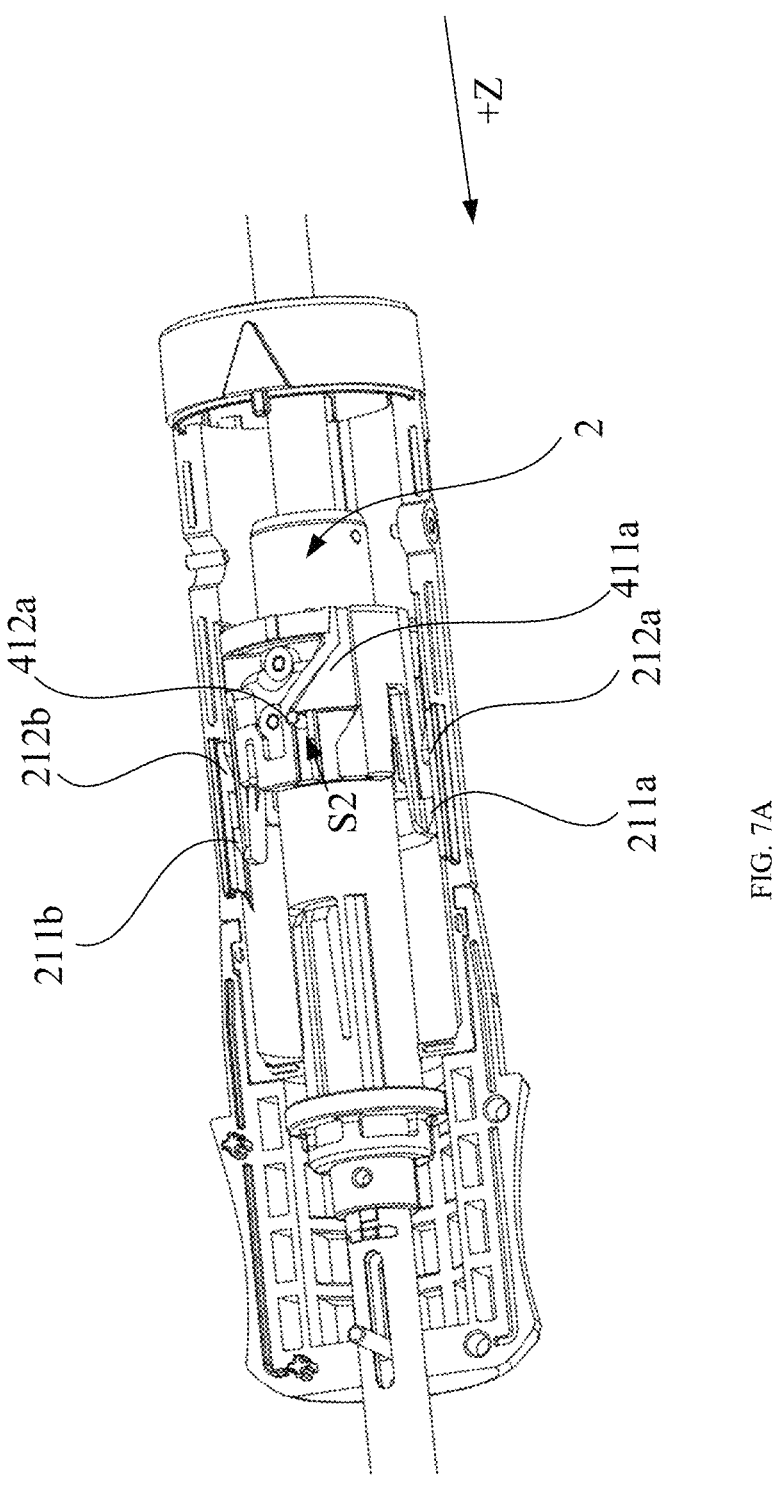
FIG. 7A is a first partial structural schematic diagram of the clip applying mechanism in an adjustment state C according to the embodiment of the present disclosure.
Figure 7B:
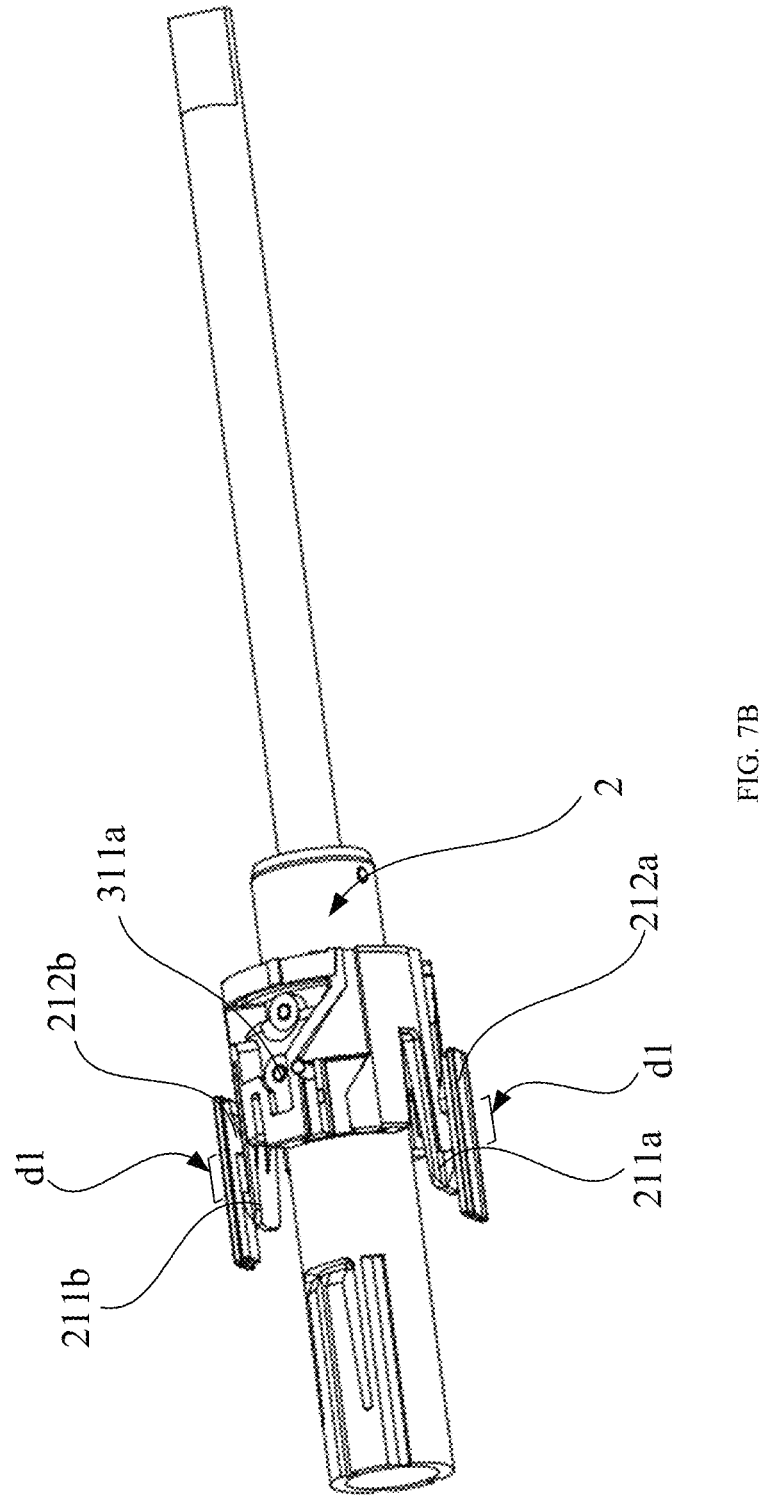
FIG. 7B is a second partial structural schematic diagram of the clip applying mechanism in the adjustment state C according to the embodiment of the present disclosure.
Figure 7C:
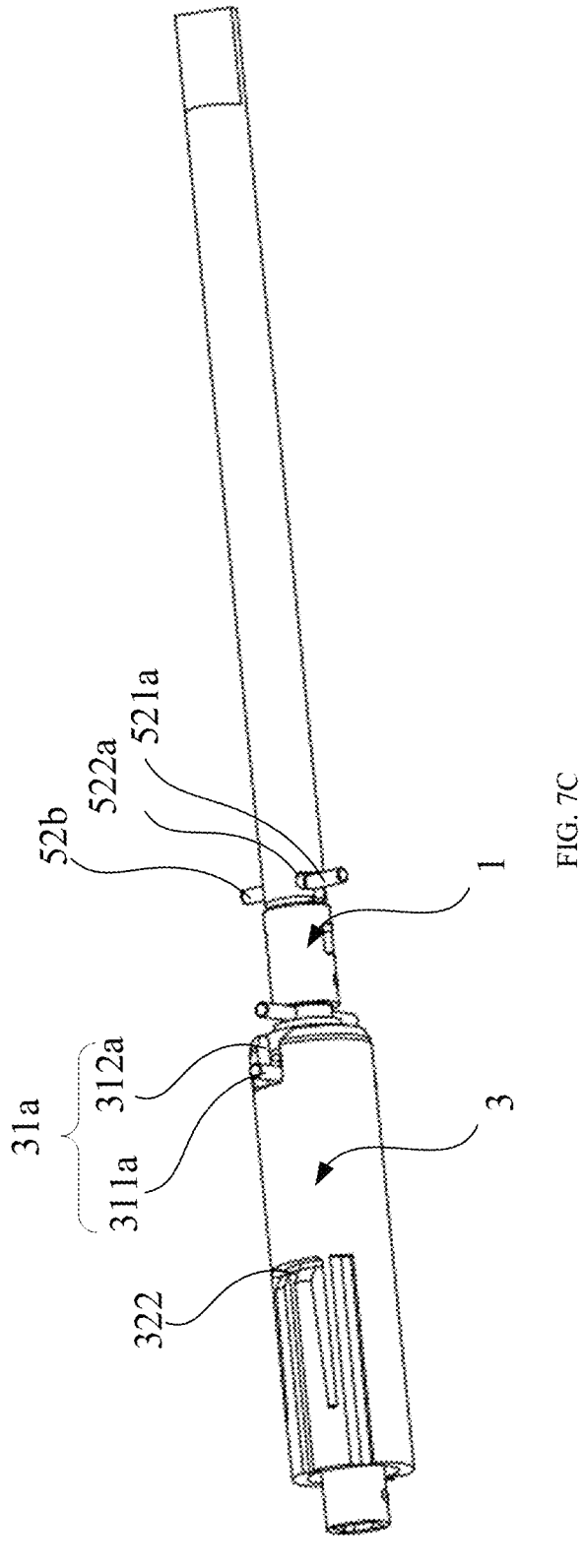
FIG. 7C is a third partial structural schematic diagram of the clip applying mechanism in the adjustment state C according to the embodiment of the present disclosure.

FIG. 6 is a partial structural schematic diagram of the clip applying mechanism in the clip feeding completion state B according to the embodiment of the present disclosure. FIG. 7A is a first partial structural schematic diagram of the clip applying mechanism in the adjustment state C according to the embodiment of the present disclosure. FIG. 7B is a second partial structural schematic diagram of the clip applying mechanism in the adjustment state C according to the embodiment of the present disclosure. FIG. 7C is a third partial structural schematic diagram of the clip applying mechanism in the adjustment state C according to the embodiment of the present disclosure.

Figure 8A:
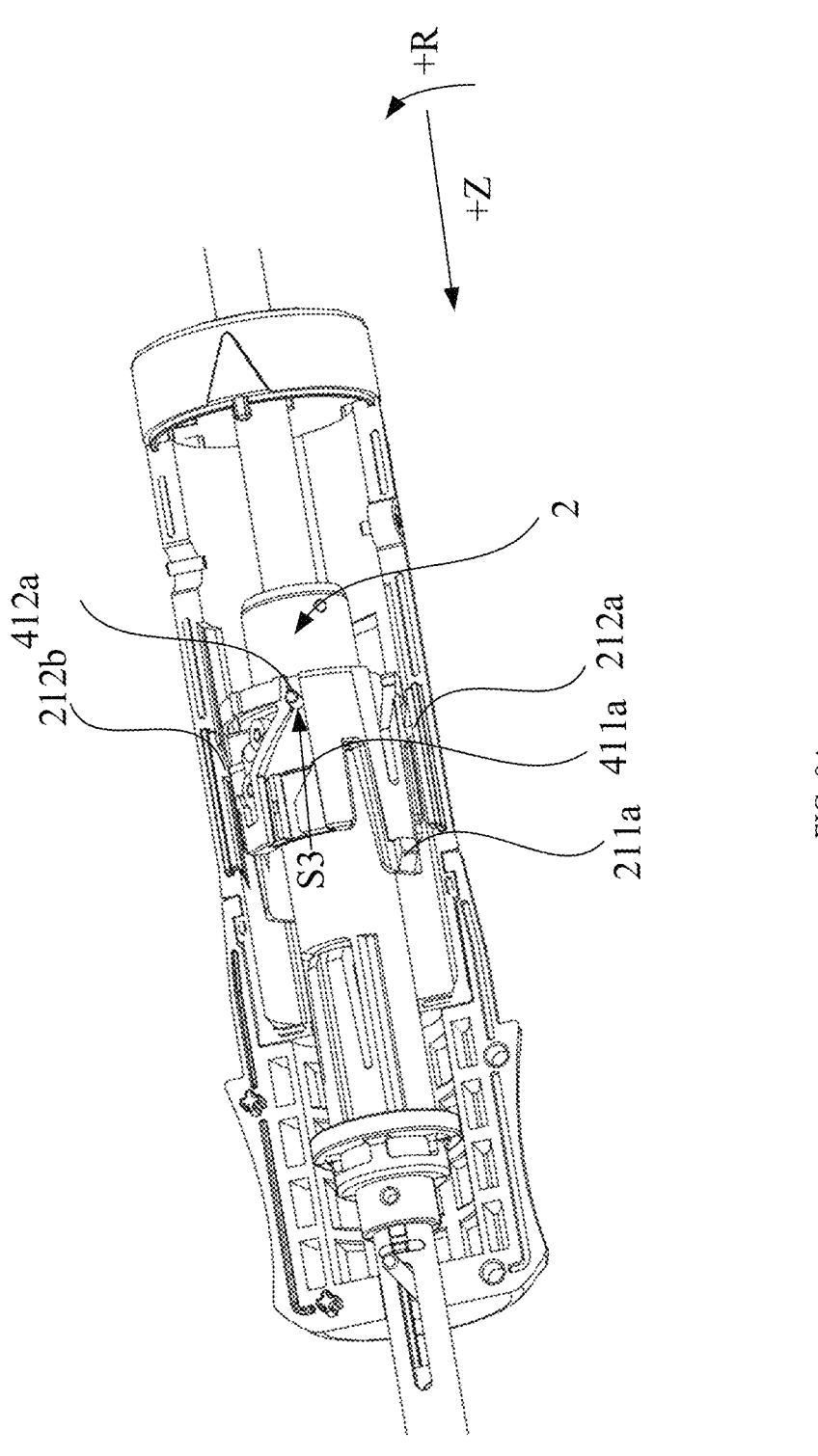
FIG. 8A is a first structural schematic diagram of the clip applying mechanism in a firing completion state D according to the embodiment of the present disclosure.
Figure 8B:
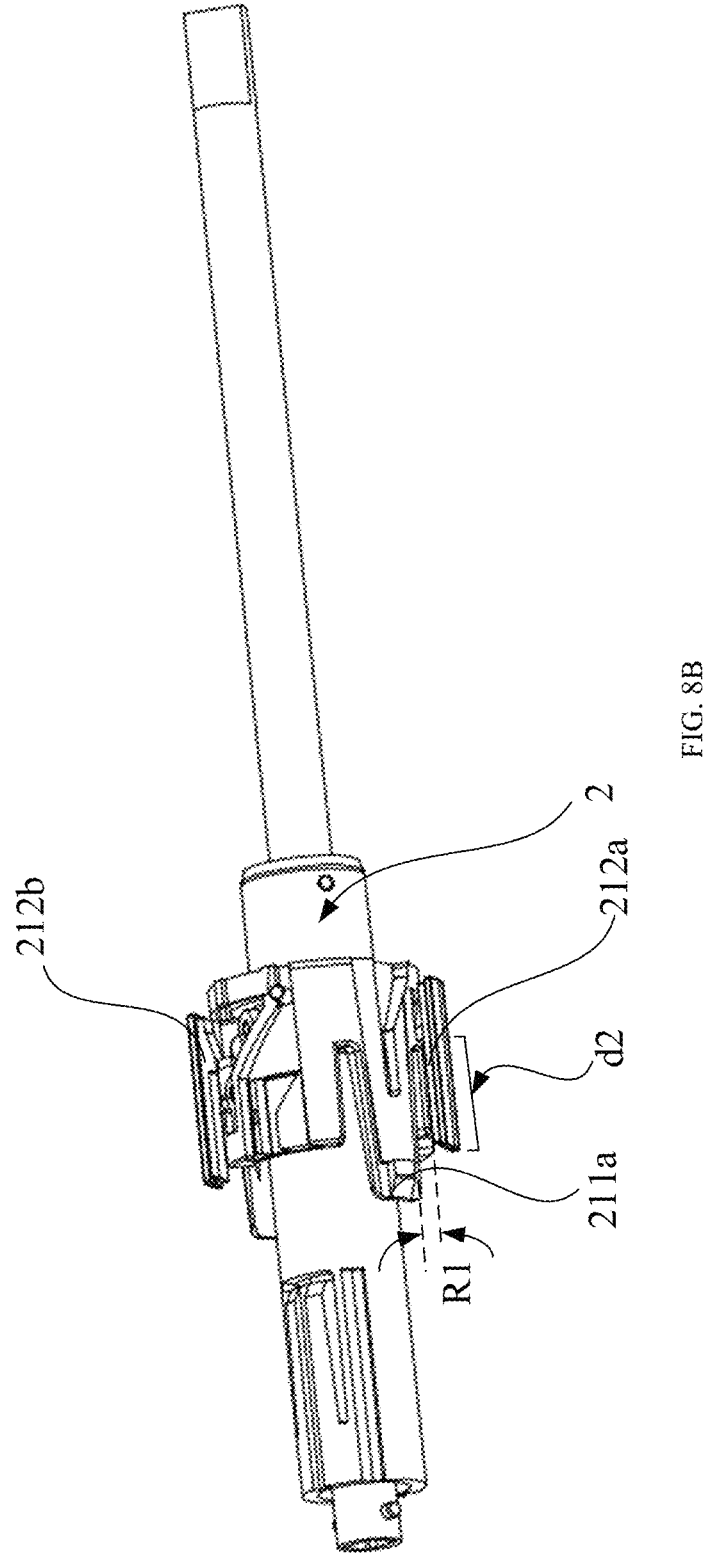
FIG. 8B is a second structural schematic diagram of the clip applying mechanism in the firing completion state D according to the embodiment of the present disclosure.
Figure 8C:
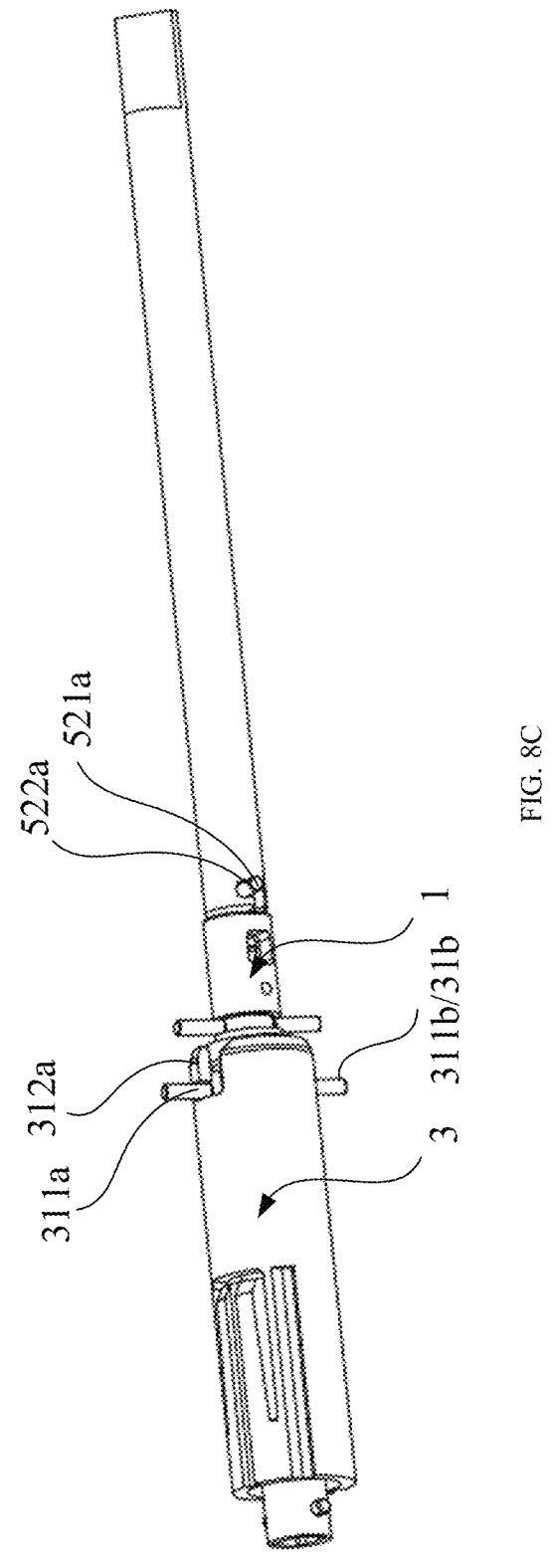
FIG. 8C is a third structural schematic diagram of the clip applying mechanism in the firing completion state D according to the embodiment of the present disclosure.

FIG. 8A is a first structural schematic diagram of the clip applying mechanism in the firing completion state D according to the embodiment of the present disclosure. FIG. 8B is a second structural schematic diagram of the clip applying mechanism in the firing completion state D according to the embodiment of the present disclosure. FIG. 8C is a third structural schematic diagram of the clip applying mechanism in the firing completion state D according to the embodiment of the present disclosure.

Figure 9A:
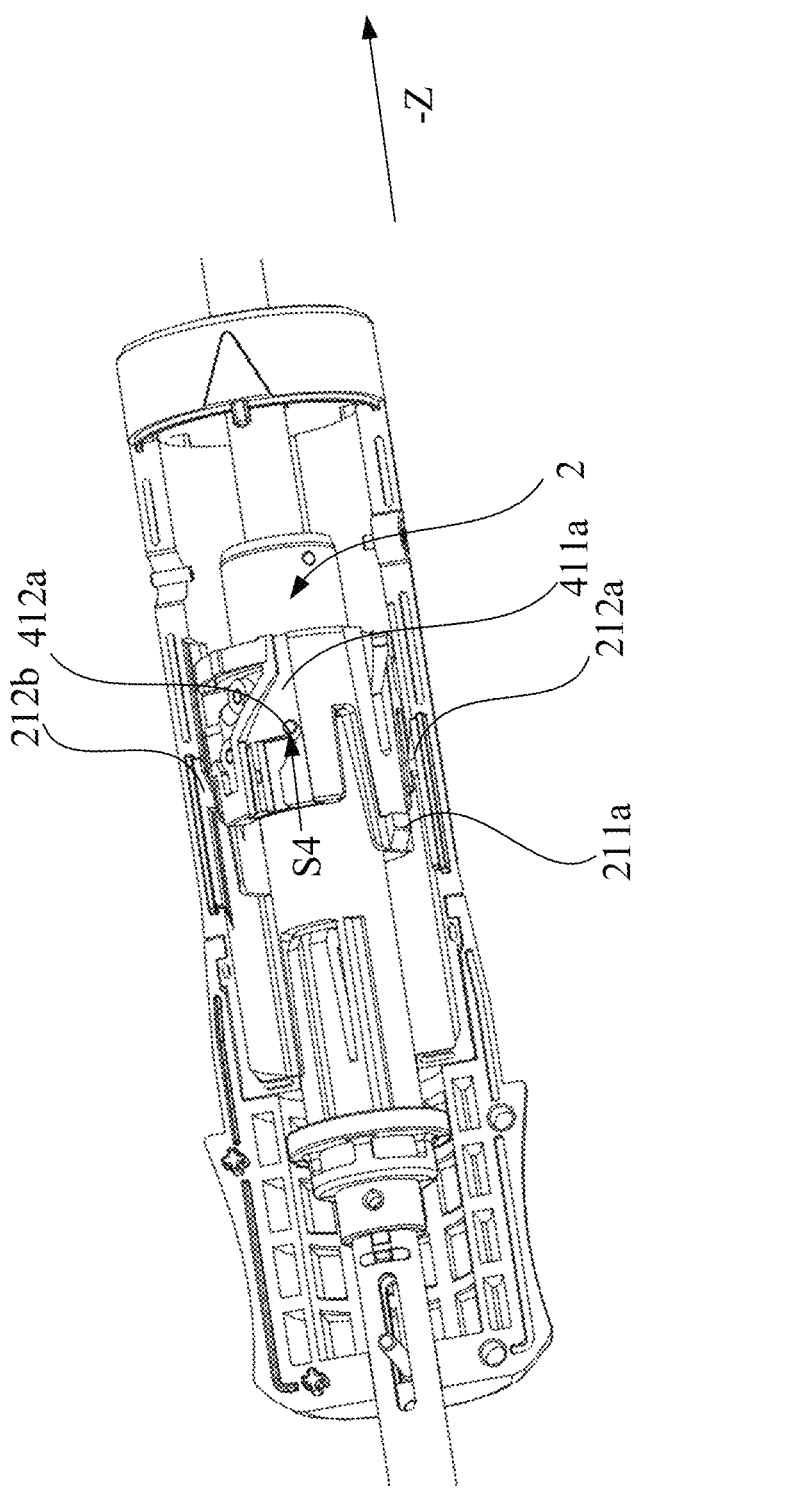
FIG. 9A is a first structural schematic diagram of the clip applying mechanism in a retreat state E according to the embodiment of the present disclosure.
Figure 9B:
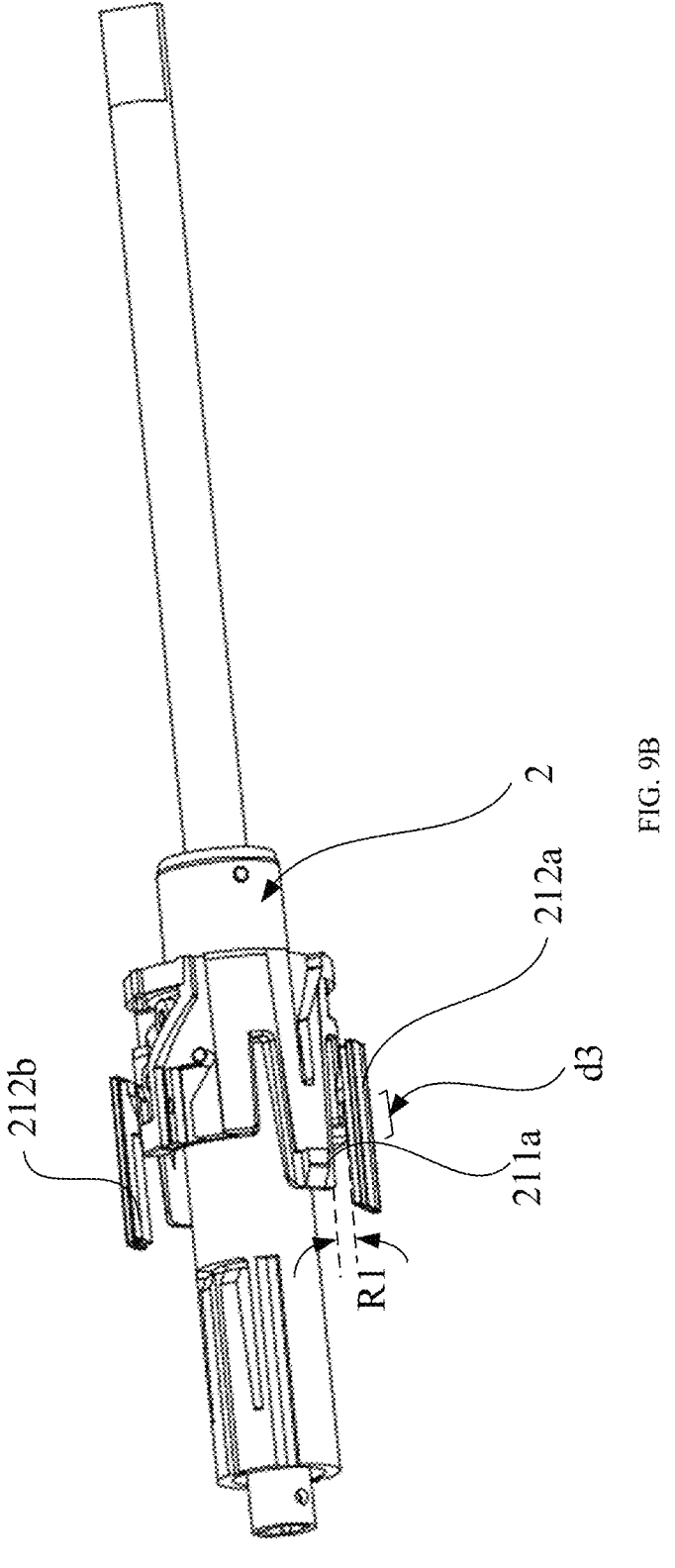
FIG. 9B is a second structural schematic diagram of the clip applying mechanism in the retreat state E according to the embodiment of the present disclosure.
Figure 9C:
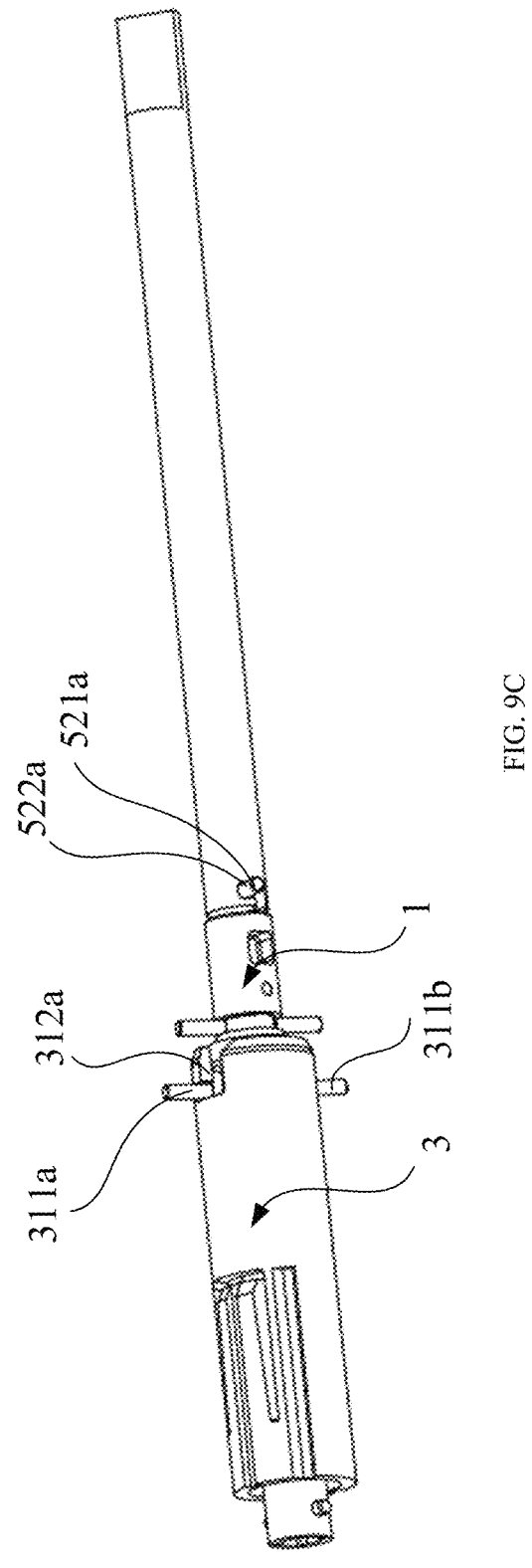
FIG. 9C is a third structural schematic diagram of the clip applying mechanism in the retreat state E according to the embodiment of the present disclosure.

FIG. 9A is a first structural schematic diagram of the clip applying mechanism in the retreat state E according to the embodiment of the present disclosure. FIG. 9B is a second structural schematic diagram of the clip applying mechanism in the retreat state E according to the embodiment of the present disclosure. FIG. 9C is a third structural schematic diagram of the clip applying mechanism in the retreat state E according to the embodiment of the present disclosure.

FIG. 10A is a first structural schematic diagram of the clip applying mechanism in the gyration state F according to the embodiment of the present disclosure. FIG. 10B is a second structural schematic diagram of the clip applying mechanism in the gyration state E according to the embodiment of the present disclosure. FIG. 10C is a third structural schematic diagram of the clip applying mechanism in the gyration state E according to the embodiment of the present disclosure.

It should be noted that when the clip applying mechanism 91 switches between different states, positions of parts or components in the clip applying mechanism 91 (including but not limited to the main-shaft connecting member 2 and the locking mechanisms 21*a*, 21*b*) also change accordingly. To facilitate understanding, the main-shaft connecting member 2 is also set to have the initial state A, the clip feeding completion state B, the adjustment state C, the firing completion state D, the retreat state E, the gyration state F, and the returning to the initial state G below, to indicate that it is synchronized with the above-described seven states of the clip applying mechanism.

Hereinafter, the locking mechanism, the first locking member, the second locking member, the main shaft, the main-shaft connecting member and the like when the clip applying mechanism is in different states will be described in conjunction with the accompanying drawings.

As shown in FIG. 3A and FIG. 3B, in a case where the clip applying mechanism is in the initial state A, the main shaft

1 and the main-shaft connecting member 2 are not applied with an external force, the main-shaft connecting member 2 is in the initial state A, and the locking mechanisms 21*a*, 21*b* are in initial positions. In this situation, the first locking member 211*a* and the second locking member 212*a* are separated from each other in the Z direction, and the first locking member 211*a* is further away from the head end 90A than the second locking member 212*a*; the first locking member 211*b* and the second locking member 212*b* are separated from each other in the Z direction and the first locking member 211*b* is further away from the head end 90A than the second locking member 212*b*.

As shown in FIG. 6, in a case where the clip applying mechanism 91 switches from the initial state A to the clip feeding completion state B, the main-shaft connecting member 2 switches from the initial state A to the clip feeding completion state B, and the locking mechanisms 21*a*, 21*b* change from the initial positions to lock positions. At the lock positions, the first locking member 211*a* and the second locking member 212*a* are locked with each other, and the first locking member 211*b* and the second locking member 212*b* are locked with each other.

For example, the above-described switching process from the initial state A to the clip feeding completion state B is implemented in a mode below:

As shown in FIG. 3A and FIG. 6, applying an external force, so that the main shaft 1 and the main-shaft connecting member 2 move along the +Z direction. During the moving process, the main shaft 1 pushes the clip-pushing assembly so that the clip is conveyed into the clamp 11; and the main-shaft connecting member 2 drives the first locking members 211*a*, 211*b* to move together along the +Z direction to respectively be locked with the second locking members 212*a*, 212*b*.

It should be noted that, in all states of the clip applying mechanism, the second housing portion 62 and the second locking members 212*a*, 212*b* all remain fixed in place.

According to the embodiment of the present disclosure, a circumferential distance along the R direction between the first locking member 211*a* and the second locking member 212*a* in the lock state is defined as zero, and an included angle along the R direction between the first locking member 211*a* and the second locking member 212*a* in the lock state is defined as zero. A definition mode of the first locking member 211*b* and the second locking member 212*b* is the same as the above mode, and no details will be repeated here.

As shown in FIG. 7A and FIG. 7B, in a case that the clip applying mechanism 91 switches from the clip feeding completion state B to the adjustment state C, the main-shaft connecting member 2 switches from the clip feeding completion state B to the adjustment state C, and the locking mechanisms 21*a*, 21*b* change from the lock positions to first unlock positions. In the first unlock positions, the first locking member 211*a* and the second locking member 212*a* are separated from each other by a first distance d1 in the Z direction; the first locking member 211*b* and the second locking member 212*b* are separated from each other by a first distance d1 in the Z direction.

For example, the above-described switching process from the clip feeding completion state B to the adjustment state C is implemented in a mode below:

Continuing to apply an external force, so that the main shaft 1 and the main-shaft connecting member 2 continue to move in the +Z direction. During the moving process, the main shaft 1 transfers the external force to the firing sleeve 5, so that the firing sleeve 5 moves along the +Z direction;

movement of the firing sleeve 5 enables the two clamp arms of the clamp 11 to move proximal to each other, to reduce an included angle between the two clamp arms, so as to achieve the purpose of adjusting the open-close angle of the clamp 11. The main-shaft connecting member 2 drives the first locking members 211*a*, 211*b* to continue to move along the +Z direction, so as to increase the distance between the first locking members 211*a*, 211*b* and the second locking members 212*a*, 212*b* in the Z direction up to the first distance d1, as shown in FIG. 7A.

According to the embodiment of the present disclosure, the above-described adjustment of the clamp 11 is particularly applicable to a case where the clip applying mechanism 91 penetrates through a narrower puncture device, which can protect the clamp 11 from being damaged by bumping when penetrating through the puncture device.

As shown in FIG. 8A and FIG. 8B, in a case where the clip applying mechanism 91 switches from the adjustment state C to the firing completion state D, the main-shaft connecting member 2 switches from the adjustment state C to the firing completion state D, and the locking mechanisms 21*a*, 21*b* change from the first unlock positions to second unlock positions. In the second unlock positions, the first locking member 211*a* and the second locking member 212*a* are separated from each other by a second distance d2 in the Z direction and the two are separated from each other by a first circumferential distance R1 in the circumferential direction R; the first locking member 211*b* and the second locking member 212*b* are separated from each other by a second distance d2 in the Z direction and the two are separated from each other by a first circumferential distance R1 in the circumferential direction R. For example, the second distance d2 is greater than the first distance d1, and the first circumferential distance R1 is greater than zero.

For example, the above-described switching process from the adjustment state C to the firing completion state D is implemented in a mode below:

Continuing to apply an external force, so that the main shaft 1 and the main-shaft connecting member 2 continue to move along the +Z direction, and the main-shaft connecting member 2 rotates along the first rotation direction +R.

During the moving process, the main shaft 1 pushes the firing sleeve 5 to continue to move along the +Z direction, so that the clamp 11 is closed, thereby firing the clip.

During the moving process, the main-shaft connecting member 2 drives the first locking members 211*a*, 211*b* to continue to move along the +Z direction to increase the first distance d1 up to the second distance d2, as shown in FIG. 8A. At the same time, the main-shaft connecting member 2 also drives the first locking members 211*a*, 211*b* to rotate a certain angle along the first rotation direction +R (for example, the angle a1 is approximately 32°) to increase the distance between the first locking member 211*a* and the second locking member 212*a* in the circumferential direction R up to the first circumferential distance R1, and to increase the distance between the first locking member 211*b* and the second locking member 212*b* in the circumferential direction R up to the first circumferential distance R1. That is to say, in the circumferential direction R, the first locking member 211*a* and the second locking member 212*a* are staggered by a rotation angle, and the first locking member 211*b* and the second locking member 212*b* are also staggered by the same rotation angle. According to the embodiment of the present disclosure, the circumferential distance between the first locking member and the second locking member when they are locked with each other is set to zero, so the first circumferential distance R1 is greater than zero.

According to the embodiment of the present disclosure, by enabling the main-shaft connecting member 2 to rotate at the same time while it is moving, the first locking member is driven to rotate relative to the second locking member and the two are staggered from each other in the circumferential direction, in this way, in a case that the firing assembly retreats in the −Z direction to reset, the first locking member and the second locking member are effectively prevented from colliding with each other, so as to prevent the reset process of the firing assembly from being obstructed.

In a case that the clip applying mechanism is in the firing completion state D, the main-shaft connecting member 2 and the main shaft 1 are at a farthest distance from the handle assembly 91. The distance between the first locking member 211*a* and the second locking member 212*a* in the Z direction and the distance between the first locking member 211*b* and the second locking member 212*b* in the Z direction reach maximum values.

As shown in FIG. 9A and FIG. 9B, in a case where the clip applying mechanism 91 switches from the firing completion state D to the retreat state E, the main-shaft connecting member 2 switches from the firing completion state D to the retreat state E, and the locking mechanisms 21*a*, 21*b* change from the second unlock positions to third unlock positions. In the third unlock position, the first locking member 211*a* and the second locking member 212*a* are separated from each other by a third distance d3 in the Z direction, and the two keep spaced from each other by the first circumferential distance R1 in the R direction; the first locking member 211*b* and the second locking member 212*b* are separated from each other by the third distance d3 in the Z direction, and the two keep separated from each other by the first circumferential distance R1 in the R direction. The third distance d3 is less than the second distance d2 and greater than zero.

For example, the above-described switching process from the firing completion state D to the retreat state E is implemented in a mode below:

Applying an external force, so that the main shaft 1 and the main-shaft connecting member 2 move along the −Z direction.

During the moving process, the main-shaft connecting member 2 drives the firing connecting member 3 to move along the −Z direction, the firing connecting member 3 drives the firing rod 4 to move along the −Z direction, and the firing rod 4 drives the firing sleeve 5 to move along the −Z direction, that is, the firing sleeve 5 retreats a certain distance. While the firing sleeve 5 retreats, the two clamp arms of the clamp 11 move away from each other, and the included angle between the two clamp arms gradually increases. At the same time, the main-shaft connecting member 2 also drives the first locking members 211*a*, 211*b* to move along the −Z direction, so that the distance between the first locking member 211*a* and the second locking member 212*a* in the Z direction decreases from the second distance d2 to the third distance d3, and the distance between the first locking member 211*b* and the second locking member 212*b* in the Z direction decreases from the second distance d2 to the third distance d3.

In the clip applying apparatus, after the clip is fired, the firing sleeve 5 is possibly stuck at the clamp 11, and it is difficult to make the firing sleeve 5 retreat (i.e. move along the −Z direction) only by virtue of the reset force of the first spring 13*a*.

According to the embodiment of the present disclosure, by setting the above-described retreat state, the external force applied to the main-shaft connecting member 2 is finally transferred to the firing sleeve 5, so that the firing sleeve 5 is forced to retreat a certain distance (because the main-shaft connecting member 2 drives the firing connecting member 3 to move, the firing connecting member 3 drives the firing rod 4 to move, and the firing rod 4 drives the firing sleeve 5 to move), thereby avoiding the problem that the firing sleeve 5 cannot be reset because it is stuck.

According to the embodiment of the present disclosure, the third distance d3 and the first distance d1 may be the same or different from each other; and specific values may be determined according to actual needs, which will not be limited in the embodiment of the present disclosure.

As shown in FIG. 10A and FIG. 10B, in a case where the clip applying mechanism 91 switches from the retreat state E to the gyration state F, the main-shaft connecting member 2 switches from the retreat state E to the gyration state F, and the locking mechanisms 21a, 21b change from the third unlock positions to fourth unlock positions. In the fourth unlock positions, the first locking member 211a and the second locking member 212a are separated from each other by a fourth distance d4 in the Z direction and the two are separated from each other by a second circumferential distance R2 in the R direction; the first locking member 211b and the second locking member 212b are separated from each other by the fourth distance d4 in the Z direction and the two are separated from each other by the second circumferential distance R2 in the R direction. The fourth distance d4 is less than the third distance d3, the second circumferential distance R2 is less than the first circumferential distance R1 and greater than zero. For example, the fourth distance d4 is equal to zero.

For example, the above-described switching process from the retreat state E to the gyration state F is in a mode below:

Under an action of the reset force of the first spring 13a, the main shaft 1 and the main-shaft connecting member 2 move along the −Z direction, and simultaneously the main-shaft connecting member 2 gyrates along the second rotation direction −R.

During the moving process, the main-shaft connecting member 2 drives the first locking members 211a, 211b to move along the −Z direction, so that the distance between the first locking member 211a and the second locking member 212a in the Z direction decreases from the third distance d3 to the fourth distance d4, and the distance between the first locking member 211b and the second locking member 212b in the Z direction decreases from the third distance d3 to the fourth distance d4, as shown in FIG. 10B. At the same time, the main-shaft connecting member 2 also drives the first locking members 211a, 211b to gyrate by an angle a2 along the second rotation direction −R, so as to reduce the first circumferential distance R1 to the second circumferential distance R2. The second rotation direction −R is opposite to the first rotation direction +R. For example, the second circumferential distance R2 is less than the first circumferential distance R1.

According to the embodiment of the present disclosure, the angle a2 is less than the angle a1 and greater than zero, so that the first locking member and the second locking member still remain staggered from each other in the circumferential direction in the gyration state, so as to prevent the first locking member and the second locking member from colliding with each other in a case where the locking mechanism returns to the initial position.

For example, the angle a2 is ½ to ⅓ of the angle a1. In one example, the angle a1 is approximately 32° and the angle a2 is approximately 16°.

According to the embodiment of the present disclosure, a distance between the first hook of the first locking member and the second hook of the second locking member in the Z direction is defined as the distance between the first locking member and the second locking member in the Z direction; for example, in a case where the locking mechanism is in a lock state, if a distance between the first hook 2111a and the second hook 2121a in FIG. 3B in the Z direction is zero, then the distance between the first locking member 211a and the second locking member 212a in FIG. 6 in the Z direction is also zero. As shown in FIG. 7B, FIG. 8B, FIG. 9B and FIG. 10B, in a case where the distance between the first hook 2111a and the second hook 2121a in the Z direction is respectively d1, d2, d3 or d4, the distance between the first locking member 211a and the second locking member 212a in the Z direction is also d1, d2, d3 or d4. It may be seen from FIG. 7B, FIG. 8B, FIG. 9B and FIG. 10B that in the Z direction, the first hook 2111a is more proximal to the head end 90A than the second hook 2121a. In one example, the fourth distance d4 is equal to zero.

In a case where the clip applying mechanism 91 recovers from the gyration state F in FIG. 10A to the initial state A in FIG. 3A, the main-shaft connecting member 2 recovers from the gyration state F to the initial state A, and the locking mechanisms 21a, 21b change from the fourth unlock positions to the initial positions.

For example, the above-described switching process from the gyration state F to the initial state A is in a mode below:

Under an action of the reset force of the second spring 13b, the main shaft 1 and the main-shaft connecting member 2 continue to move along the −Z direction, and at the same time, the main-shaft connecting member 2 continues to rotate along the second rotation direction −R until the main-shaft connecting member 2 returns to the initial position.

During the moving process, the main-shaft connecting member 2 drives the first locking members 211a, 211b to continue moving along the −Z direction, so that the first locking members 211a, 211b move to a side of the second locking members 212a, 212b that is distal to the head end 90A, so as to enable the locking mechanisms 21a, 21b to return to the initial positions. As compared with the situation that the first hook 2111a is more proximal to the head end 90A than the second hook 2121a in FIG. 7B, FIG. 8B, FIG. 9B and FIG. 10B, because the first hook 2111a in FIG. 3B retreats to the initial position, the first locking members 211a, 211b are located on the side of the second locking members 212a, 212b that is distal to the head end 90A.

At the same time, the main-shaft connecting member 2 also drives the first locking members 211a, 211b to continue to rotate by an angle a3 along the second rotation direction −R to reduce the second circumferential distance R2 to zero.

According to the embodiment of the present disclosure, the angle a3 is equal to the angle a1 minus the angle a2, that is, a3=a1−a2. In this way, the first locking member and the second locking member both gyrate to the initial positions. For example, the angle a3 is approximately 16°.

The embodiments of the present disclosure are described by taking the two locking mechanisms 21a, 21b as an example, it may be understood that the total number of locking mechanisms may be one or more than two, for example, three, etc., which will not be limited in the embodiments of the present disclosure.

In a case where the total number of locking mechanisms is plural, the plurality of locking mechanisms are arranged between the main-shaft connecting member 2 and the housing 6 along the circumferential direction of the main-shaft connecting member 2 at equal interval, so that the force endured by the main-shaft connecting member 2 or the housing 6 is uniform and an effect of locking in place is increased.

For example, the main-shaft connecting member 2 is a tubular member 20, and the two locking mechanisms 21*a*, 21*b* are symmetrically arranged in the radial direction of the tubular member 20; in this way, the total number of locking mechanisms is reduced as much as possible, the fabrication costs is saved, and the manufacturing difficulty is reduced, under the condition of ensuring a uniform force endured by the main-shaft connecting member 2 or the housing 6.

In the clip applying apparatus, in a case where the clip is fired, the firing sleeve is possibly stuck at the clamp. Because the firing sleeve is stuck, it is difficult to make the firing sleeve retreat and reset only by virtue of the reset force of the reset member, thereby affecting actions of conveying and firing the next clip.

To this end, another embodiment of the present disclosure provides a clip applying mechanism of a clip applying apparatus, which at least aims to be capable of forcibly pulling the firing sleeve back a certain distance after the clip is fired, so as to assist in reset of the firing sleeve.

For example, the clip applying mechanism of the clip applying apparatus provided by another embodiment of the present disclosure includes: a tube body, a main shaft, a clip-cartridge assembly, a clip-pushing assembly and a firing assembly. The tube body includes a head end and a tail end opposite to each other; the main shaft is arranged proximal to the tail end and at least portion of the main shaft is arranged in the tube body; the clip-cartridge assembly penetrates through the tube body and includes: a clip cartridge arranged in the tube body and an end effector configured to penetrate out of the head end, the clip cartridge is configured to be filled with a clip; at least portion of the clip-pushing assembly is arranged in the tube body, the clip-pushing assembly is configured to be pushed by the main shaft toward the head end to convey the clip in the clip cartridge into the end effector; at least portion of the firing assembly is located in the tube body, and the firing assembly is configured to be pushed by the main shaft toward the head end to close the end effector, so that the clip within the end effector is fired. Further, the clip applying mechanism further includes: a main-shaft connecting member, a firing connecting member and an engagement mechanism. The main-shaft connecting member is connected with the main shaft; the firing connecting member is connected with the firing assembly; the engagement mechanism is arranged between the main-shaft connecting member and the firing connecting member. The engagement mechanism, the firing connecting member, the main-shaft connecting member and the firing assembly are configured such that: in a case where the clip is fired, the main-shaft connecting member drives the firing connecting member to move away from the head end through the engagement mechanism, and the firing connecting member drives the firing assembly to move in a same direction, so that the end effector is partially opened.

In the above-described clip applying mechanism provided by the embodiment of the present disclosure, by providing the main-shaft connecting member connected with the main shaft and the firing connecting member respectively connected with the main-shaft connecting member and the firing assembly, after the clip is fired, the firing assembly is pulled back in a direction facing away from the head end by using the main-shaft connecting member, the engagement mechanism and the firing connecting member, thereby facilitating reset of the firing sleeve and avoiding impact on subsequent actions.

The above-described clip applying mechanism and clip applying apparatus will be described below with reference to FIG. 1A to FIG. 10C. In order to maintain clarity and conciseness of the present disclosure, components mentioned in the following embodiments that are the same as those in the foregoing embodiments will not be described repeatedly, and the descriptions in the foregoing embodiments may be referred to for related structures and setting modes thereof.

As shown in FIG. 1A, FIG. 1B and FIG. 2, a clip applying apparatus 900 provided by still another embodiment of the present disclosure includes a clip applying mechanism 91 and a handle assembly 92.

For example, the clip applying mechanism 91 is detachably connected with the handle assembly 92. The clip applying mechanism 91 includes a tube body 90, a main shaft 1, a main-shaft connecting member 2, a firing connecting member 3, a clip-cartridge assembly, a clip-pushing assembly, a firing assembly, a housing 6, a pushing rod 7, and an end cap 12. The firing assembly includes, for example, a firing rod 4 and a firing sleeve 5. The clip-cartridge assembly includes, for example, a clip cartridge 9 and a clamp 11 (also referred to as an end effector). The clip-pushing assembly includes, for example, a pushing block 8 and a clip pushing piece 10.

For example, the tube body 90 includes a head end 90A and a tail end 90B opposite to each other. The main shaft 1 is arranged proximal to the tail end 90B and at least portion of the main shaft 1 is located in the tube body 90. The clip-cartridge assembly penetrates through the tube body 90, and the clip-cartridge assembly includes a clip cartridge arranged in the tube body 90 and a clamp 11 penetrating out of the head end 90A. The clip cartridge is configured to be filled with a clip. At least portion of the clip-pushing assembly is arranged in the tube body 90, and the clip-pushing assembly is configured to be pushed by the main shaft 1 toward the head end 90A to convey the clip in the clip cartridge into the clamp 11. At least portion of the firing assembly is located in the tube body 90, and the firing assembly is configured to be pushed by the main shaft 1 toward the head end 90A to close the clamp 11, so that the clip in the clamp 11 is fired.

As shown in FIG. 3B, FIG. 3C, FIG. 4A, FIG. 7C, FIG. 8C, FIG. 9C and FIG. 10C, for example, the clip applying mechanism 91 further includes engagement mechanisms 31*a*, 31*b* arranged between the main-shaft connecting member 2 and the firing connecting member 3. In a case where the clip is fired, the main-shaft connecting member 2 drives the firing connecting member 3 to move along the −Z direction through the engagement mechanisms 31*a*, 31*b*, and the firing connecting member 3 drives the firing assembly to move in a same direction, so that the clamp 11 is partially opened.

As shown in FIG. 3C, for example, the main-shaft connecting member 2 is connected with the main shaft 1 through an axial engagement mechanism 22.

As shown in FIG. 2, FIG. 3 and FIG. 3A, for example, the firing assembly includes a firing sleeve 5 and a firing rod 4 at least partially located in the firing sleeve 5.

For example, the firing sleeve 5 is used as the tube body 90 and connected with the firing rod 4, so that in a case where the firing rod 4 moves in the Z direction, the firing sleeve 5 also moves in the Z direction. For example, in a case where the firing rod 4 moves along the −Z direction, it drives the firing sleeve 5 to retreat along the −Z direction, so that the clamp 11 is partially opened.

For example, the firing rod 4 is connected with the firing connecting member 3, so that in a case where the firing connecting member 3 moves in the Z direction, the firing rod 4 also moves in the Z direction. For example, in a case where the firing connecting member 3 moves along the –Z direction, it drives the firing rod 4 to retreat along the –Z direction.

For example, the firing rod 4 includes a first rod-shaped portion 4A and a second rod-shaped portion 4B in an extension direction of the firing rod 4; the first rod-shaped portion 4A is proximal to the head end 90A, and the second rod-shaped portion 4B is distal to the head end 90A. The firing sleeve 5 is sleeved on and connected with the first rod-shaped portion 4A, and the firing connecting member 3 is sleeved on and connected with the second rod-shaped portion 4B.

According to the embodiment of the present disclosure, the term "rod" or "rod-shaped portion" represents an elongated shape, which does not mean that the rod or the rod-shaped portion is a solid structure. For example, as shown in FIG. 3D, the firing rod 4 is hollow to form a cavity that is capable of accommodating the main shaft 1.

As shown in FIG. 3B, FIG. 3C, FIG. 3C, FIG. 4A, FIG. 7C, FIG. 8C, FIG. 9C and FIG. 10C, the engagement mechanism 31*a* includes a pin 311*a* (i.e., a first engagement member) arranged on the main-shaft connecting member 2 and a slot 312*a* (i.e., a second engagement member) arranged on the firing connecting member 3; the engagement mechanism 31*b* includes a pin 311*b* (i.e., a first engagement member) arranged on the main-shaft connecting member 2 and a slot 312*b* (i.e., a second engagement member) arranged on the firing connecting member 3.

For example, the engagement mechanisms 31*a*, 31*b* have a separate state, a release state, and a lock state.

In the separate state, the pin 311*a* and the slot 312*a* are separated from each other, and the pin 311*a* is located outside the slot 312*a*; the pin 311*b* and the slot 312*b* are separated from each other, and the pin 311*b* is located outside the slot 312*b*. As shown in FIG. 3 to FIG. 3C, for example, in a case where the clip applying mechanism 91 is in the initial state A, the engagement mechanisms 31*a*, 31*b* are in the separate state.

In the release state, the pins 311*a*, 311*b* are respectively located in the slots 312*a*, 312*b* and are capable of moving out of the slots 312*a*, 312*b*. As shown in FIG. 6, FIG. 7C and FIG. 10C, in a case where the clip applying mechanism 91 is in the clip feeding completion state B, the adjustment state C or the gyration state F, the engagement mechanisms 31*a*, 31*b* are in the release state.

In the lock state, the pins 311*a*, 311*b* are respectively locked with the slots 312*a*, 312*b*. In the lock state, relative positions of the main-shaft connecting member 2 and the firing connecting member 3 both remain fixed in the Z direction or the R direction, so the main-shaft connecting member 2 can drive the firing connecting member 3 to move in the Z direction. As shown in FIG. 8C and FIG. 9C, in a case where the clip applying mechanism 91 is in the firing completion state D or the retreat state E, the engagement mechanisms 31*a*, 31*b* are in the lock state.

After the clip is fired (i.e., in the firing completion state D or the retreat state E), the engagement mechanisms 31*a*, 31*b* are in the lock state, and the firing connecting member 3 and the main-shaft connecting member 2 are locked with each other. Then, an external force is applied to the main-shaft connecting member 2 to enable the main-shaft connecting member 2 to move in the –Z direction, so that the firing connecting member 3 retreats in the –Z direction under the drive of the main-shaft connecting member 2; and finally, the firing sleeve 5 also retreats. By arranging the engagement mechanisms 31*a*, 31*b* in the firing completion state D and the retreat state E to be in the lock state, it is ensured that the firing connecting member 3 and the main-shaft connecting member 2 cannot be separated from each other at least in the firing process and the retreating process, so as to avoid accidents occurring in the above-described two processes.

According to the embodiment of the present disclosure, the engagement mechanisms 31*a*, 31*b* may have the same structure or different structures; in a case where the two have a same structure, a fabrication process is simplified, which, thus, is preferred. The embodiments of the present disclosure are illustrated by taking that the engagement mechanisms 31*a*, 31*b* have the same structure as an example.

FIG. 10D is a partial enlarged structural schematic diagram of the engagement mechanism in FIG. 10C. Hereinafter, it is illustrated by taking the engagement mechanism 31*a* as an example. As shown in FIG. 10D, the slot 312*a* includes a release position 312*p*1 and a lock position 312*p*2, and the pin 311*a* is capable of moving between the release position 312*p*1 and the lock position 312*p*2.

For example, in a case where the engagement mechanism 31*a* is in a lock state, the pin 311*a* is in the lock position 312*p*2. In a case where the engagement mechanism 31*a* is in a release state, the pin 311*a* is in the release position 312*p*1 and is capable of moving out of the slot 312*a*. In a case where the engagement mechanism 31*a* is in a separate state, the pin 311*a* is located outside the slot 312*a*, so it is neither located in the release position 312*p*1 nor located in the lock position 312*p*2.

Hereinafter, the engagement mechanism, the firing connecting member, the main-shaft connecting member and the like when the clip applying mechanism is in different states will be described in conjunction with the accompanying drawings.

As shown in FIG. 3A to FIG. 3C, in a case where the clip applying mechanism 91 is in the initial state A, the main-shaft connecting member 2 is in the initial state A, the engagement mechanism 31*a* is in the separate state, and the pin 311*a* is located outside the slot 312*a*. For example, the pin 311*a* is located on a side of the slot 312*a* that is distal to the head end 90A.

As shown in FIG. 6, in a case where the clip applying mechanism 91 switches from the initial state A to the clip feeding completion state B, the main-shaft connecting member 2 moves along the +Z direction and drives the pin 311*a* to move along the +Z direction, which enables the pin 311*a* to move to the release position 312*p*1 of the slot 312*a*, so that the engagement mechanism 31*a* is in the release state. By enabling the pin 311*a* to move to the release position 312*p*1 of the slot 312*a*, it is favorable for pushing the firing connecting member 3 along the +Z direction while pushing the main-shaft connecting member 2 along the +Z direction subsequently.

As shown in FIG. 7A to FIG. 7C, in a case where the clip applying mechanism 91 switches from the clip feeding completion state B to the adjustment state C, the main-shaft connecting member 2 drives the pin 311*a* to continue to move along the +Z direction.

As shown in FIG. 8A to FIG. 8C, in a case where the clip applying mechanism 91 switches from the adjustment state C to the firing completion state D, the main-shaft connecting member 2 continues to move along the +Z direction and simultaneously rotates along the first rotation direction +R. Under the drive of the main-shaft connecting member 2, the pin 311*a* also continues to move along the +Z direction, and simultaneously rotates along the first rotation direction +R from the release position 312p1 to the lock position 312p2. In this situation, the engagement mechanism 31a is in the lock state, and relative positions of the main-shaft connecting member 2 and the firing connecting member 3 are locked to prepare for subsequent retreat of the firing assembly.

As shown in FIG. 9A to FIG. 9C, in a case where the clip applying mechanism 91 switches from the firing completion state D to the retreat state E, the main-shaft connecting member 2 drives the firing connecting member 3 to move along the −Z direction, the firing connecting member 3 drives the firing rod 4 to move along the −Z direction, the firing rod 4 drives the firing sleeve 5 to move along the −Z direction, and finally, the firing sleeve 5 retreats a certain distance. Through the above-described operations, the firing sleeve 5 is forced to retreat by virtue of an external force, thereby solving the problem that the firing sleeve 5 is stuck at the clamp 11. In this situation, the engagement mechanism 31a is still in the lock state.

As shown in FIG. 10A to FIG. 10C, in a case where the clip applying mechanism 91 switches from the retreat state E to the gyration state F, the main-shaft connecting member 2 moves along the −Z direction and simultaneously gyrates along the second rotation direction −R. Under the drive of the main-shaft connecting member 2, the pin 311a also moves along the −Z direction, and simultaneously gyrates along the second rotation direction −R from the lock position 312p2 to the release position 312p1. In this situation, the engagement mechanism 31a is in the release state.

Next, in a case where the clip applying mechanism 91 recovers from the gyration state F in FIG. 10A to the initial state A in FIG. 3A, the main-shaft connecting member 2 continues to move along the −Z direction, and simultaneously, the main-shaft connecting member 2 continues to gyrate along the second rotation direction −R. Under the drive of the main-shaft connecting member 2, the pin 311a also continues to move along the −Z direction, and simultaneously leaves from the slot 312a. In this situation, the engagement mechanism 31a recovers to the initial separate state.

It can be seen from the above processes in the embodiment of the present disclosure, by using the main-shaft connecting member 2, the firing connecting member 3 and the engagement mechanism 31, the firing sleeve 5 is forced to retreat a certain distance after the firing is completed, which effectively avoids the problem of difficult reset caused by the firing sleeve 5 being stuck in the clamp 11, and ensures the firing sleeve 5 to be reset more smoothly.

As shown in FIG. 8C, for example, the firing connecting member 3 is a tubular member, the slots 312a, 312b are through slots arranged on the tubular member, notches of the slots 312a, 312b are open toward the −Z direction, and the release position 312p1 is located at the bottom of the slots 312a, 312b. By opening the notches of the slots 312a, 312b toward the −Z direction, it is favorable for the pins 311a, 311b to quickly arrive the release positions of the slots when moving along the +Z direction. In one example, the slots 312a, 312b are L-shaped slots.

The embodiments of the present disclosure are described by taking the two engagement mechanisms 31a, 31b as an example, it may be understood that the total number of engagement mechanisms may be one or more than two, for example, three, etc., which will not be limited in the embodiments of the present disclosure.

In a case where the total number of engagement mechanisms is plural, the plurality of engagement mechanisms are arranged between the main-shaft connecting member 2 and the firing connecting member 3 along the circumferential direction of the main-shaft connecting member 2 at equal interval, so that the force endured by the main-shaft connecting member 2 or the firing connecting member 3 is uniform and the engagement effect is increased.

For example, the main-shaft connecting member 2 is a tubular member 20, and the two engagement mechanisms 31a, 31b are symmetrically arranged in the radial direction of the tubular member 20; in this way, the total number of engagement mechanisms may be reduced as much as possible, the fabrication costs is saved, and the manufacturing difficulty is reduced, under the condition of ensuring a uniform force endured by the main-shaft connecting member 2 or the firing connecting member 3.

As shown in FIG. 2 and FIG. 3C, the clip applying mechanism 91 further includes an axial engagement mechanism 32 arranged between the firing connecting member 3 and the firing rod 4. Herein, the firing connecting member 3 and the firing rod 4 are configured to be engaged with each other through the axial engagement mechanism 32 in the axial direction of the firing connecting member 3, but the two are configured to be capable of achieving relative movement in the circumferential direction of the firing connecting member 3.

According to the embodiment of the present disclosure, the firing connecting member 3 is arranged parallel to the tube body 90, so the axial direction Z of the tube body 90 may be referred to for the axial direction of the firing connecting member 3; the circumferential direction R of the tube body 90 may be referred to for the circumferential direction of the firing connecting member 3; and the radial direction P of the tube body 90 shown in FIG. 3D may be referred to for the radial direction of the firing connecting member 3.

FIG. 11 is a structural schematic diagram of a firing connecting member according to the embodiment of the present disclosure. As shown in FIG. 2 and FIG. 11, for example, the axial engagement mechanism 32 includes a slot 321 arranged on the firing rod 4 and tabs 322a, 322b arranged on the firing connecting member 3. The tabs 322a, 322b are configured to move in the slot 321 along the circumferential direction of the firing connecting member 3.

According to the embodiment of the present disclosure, by providing the axial engagement mechanism 32 between the firing connecting member 3 and the firing rod 4, on one hand, the firing connecting member 3 and the firing rod 4 keep relative positions unchanged in the Z direction, which is favorable for the firing connecting member 3 to drive the firing rod 4 to move in the Z direction; on the other hand, the firing rod 4 is capable of rotating in the R direction relative to the firing connecting member 3, which, thus, is favorable for rotation of the firing assembly or the clip-pushing assembly, so that a rotation angle of the clamp 11 or the firing sleeve 5 can be controlled.

For example, the firing connecting member 3 is connected with the first housing portion 61 through other engagement mechanism; in a case where the first housing portion 61 rotates, it drives the firing connecting member 3 to rotate, and further control the rotation angle of the clamp 11 or the firing sleeve 5.

For example, the slot 321 is an annular slot extending along a circumferential direction of the firing connecting member 3. In this way, the tabs 322a, 322b rotate in the slot 321 by 360 degrees to increase flexibility of the rotation angle.

The embodiments of the present disclosure are described by taking two pin tabs 322a, 322b as an example, it may be understood that the total number of tabs may be one or more than two, for example, three, etc., which will not be limited in the embodiments of the present disclosure.

In a case where the total number of tabs is plural, the plurality of tabs are arranged along the circumferential direction of the firing connecting member 3 at equal interval, so that the force endured by the firing connecting member 3 or the firing rod 4 is uniform, thereby avoiding damage by the clip applying mechanism to the firing connecting member 3 or the firing rod 4 during operation.

As shown in FIG. 3C, for example, the firing connecting member 3 is a tubular member, and the two tabs 322a, 322b are symmetrically arranged in the radial direction of the tubular member; in this way, the total number of tabs may be reduced as much as possible, the fabrication costs is saved, and the manufacturing difficulty is reduced, under the condition of ensuring a uniform force endured by the firing connecting member 3 or the firing rod 4.

As shown in FIG. 2, for example, the housing 6 is used for accommodating at least portion of the main shaft 1, the main-shaft connecting member 2 and the firing connecting member 3, that is, the main shaft 1, the main-shaft connecting member 2 and the firing connecting member 3 are all located in the housing 6.

In at least some embodiments, the clip applying mechanism 91 further includes a circumferential engagement mechanism 33 arranged between the firing connecting member 3 and the housing 6. The firing connecting member 3 and the housing 6 are engaged with each other in the R direction through the circumferential engagement mechanism 33, but the firing connecting member 3 and the housing 6 are capable of achieving relative movement in the Z direction. For example, the firing connecting member 3 moves in the +Z direction or the −Z direction relative to the housing 6.

As shown in FIG. 3C and FIG. 5, for example, the circumferential engagement mechanism 33 is arranged between the firing connecting member 3 and the second housing portion 62. The circumferential engagement mechanism 33 includes a plurality of protrusions 331 (i.e., tabs, as shown in FIG. 5) arranged on the second housing portion 62 and a plurality of slots 332 (i.e. slots, as shown in FIG. 11) arranged on the firing connecting member 3; the plurality of protrusions 331 and the plurality of slots 332 are arranged in one-to-one correspondence and are configured to be engaged with each other.

For example, the second housing portion 62 includes an opening 622 located on a side proximal to the head end 90A in the axial direction, and the plurality of protrusions 331 are distributed along a circumference of the opening 622 at equal interval. The plurality of slots 332 are located on an outer surface of the firing connecting member 3 and are distributed along the circumferential direction of the firing connecting member 3 at equal interval, so that the firing connecting member 3 and the second housing portion 62 can endure more uniform force in a case where they are connected with each other.

According to the embodiment of the present disclosure, by arranging the plurality of protrusions 331 and the plurality of slots 332, the firing connecting member 3 and the second housing portion 62 keep relatively fixed in the R direction, so as to ensure that the firing connecting member 3 will not rotate in a case where the firing sleeve 5 advances in the +Z direction or retreats in the −Z direction, thereby increasing operation safety.

The embodiments of the present disclosure are described by taking a plurality of protrusions and a plurality of slots as an example; and it may be understood that the total number of protrusions or slots may be set according to actual needs, which will not be limited in the present disclosure. In addition, the embodiments of the present disclosure are described by taking the protrusions and the slots as an example, it may be understood that in other embodiments, a mode of slots and pins may also be used, which will not be limited in the embodiments of the present disclosure.

In the clip applying apparatus, the handle assembly is used for driving the clip applying mechanism to execute respective actions, for example, conveying the clip, firing the clip, resetting the firing assembly, resetting the clip-pushing assembly, and so on. While the clip applying mechanism executes the above-described actions, the main shaft moves in the axial direction relative to the housing, and the main-shaft connecting member reaches different positions under the drive of the main shaft. In order to ensure stability and safety of the clip applying apparatus in terms of operation, it is necessary to ensure that the main shaft and the main-shaft connecting member both quickly and accurately arrives in place while the clip applying mechanism executes the respective actions.

To this end, yet another embodiment of the present disclosure provides a clip applying mechanism of a clip applying apparatus, which at least aims to be capable of guiding the main shaft and the main-shaft connecting member during the moving process, so that the main shaft and the main-shaft connecting member both quickly and accurately arrives in place, thereby ensuring stability and safety of the clip applying mechanism in terms of operation.

For example, the clip applying mechanism of the clip applying apparatus provided by yet another embodiment of the present disclosure includes: a tube body, a main shaft, a clip-cartridge assembly, a clip-pushing assembly and a firing assembly. The tube body includes a head end and a tail end opposite to each other; the main shaft is arranged proximal to the tail end and at least portion of the main shaft is arranged in the tube body; the clip-cartridge assembly is configured to penetrate through the tube body and includes: a clip cartridge arranged in the tube body and an end effector configured to penetrate out of the head end; the clip cartridge is configured to be filled with a clip; at least portion of the clip-pushing assembly is arranged in the tube body, and the clip-pushing assembly is configured to be pushed by the main shaft toward the head end to convey the clip in the clip cartridge into the end effector; at least portion of the firing assembly is located in the tube body, and the firing assembly is configured to be pushed by the main shaft toward the head end to close the end effector, so that the clip in the end effector is fired. Furthermore, the clip applying mechanism further includes: a main-shaft connecting member, a housing and a first guiding mechanism. The main-shaft connecting member is sleeved on the main shaft and connected with the main shaft; the housing is configured to accommodate the main shaft and the main-shaft connecting member, and the main-shaft connecting member is configured to be capable of moving relative to the housing in both an axial direction of the tube body and a circumferential direction of the tube body; the first guiding mechanism is arranged between the main-shaft connecting member and the housing, and is configured to guide the main-shaft connecting member to move relative to the housing.

In the above-described clip applying mechanism provided by the embodiment of the present disclosure, the first guiding mechanism is arranged between the main-shaft connecting member and the housing, so that the main-shaft connecting member is guided by the first guiding mechanism in the process of moving or rotating; because the main-shaft connecting member is also connected with the main shaft, it is ensured that both the main shaft and the main-shaft connecting member quickly and accurately arrive in place while the clip applying mechanism executes respective actions.

Hereinafter, the above-described clip applying mechanism and clip applying apparatus will be described with reference to FIG. 1A to FIG. 11. In order to maintain clarity and conciseness of the present disclosure, components mentioned in the following embodiments that are the same as those in the foregoing embodiments will not be described repeatedly, and the description in the foregoing embodiments may be referred to for related structures and setting modes thereof.

As shown in FIG. 1A, FIG. 1B and FIG. 2, the clip applying apparatus 900 provided by yet another embodiment of the present disclosure includes a clip applying mechanism 91 and a handle assembly 92.

For example, the clip applying mechanism 91 is detachably connected with the handle assembly 92. The clip applying mechanism 91 includes a tube body 90, a main shaft 1, a main-shaft connecting member 2, a firing connecting member 3, a clip-cartridge assembly, a clip-pushing assembly, a firing assembly, a housing 6, a pushing rod 7, and an end cap 12. The firing assembly includes, for example, a firing rod 4 and a firing sleeve 5. The clip-cartridge assembly includes, for example, a clip cartridge 9 and a clamp 11 (also referred to as an end effector). The clip-pushing assembly includes, for example, a pushing block 8 and a clip pushing piece 10.

For example, the tube body 90 includes a head end 90A and a tail end 90B opposite to each other. The main shaft 1 is arranged proximal to the tail end 90B and at least portion of the main shaft 1 is arranged in the tube body 90. The clip-cartridge assembly penetrates through the tube body 90, and the clip-cartridge assembly includes a clip cartridge arranged in the tube body 90 and a clamp 11 penetrates out of the head end 90A. The clip cartridge is configured to be filled with a clip. At least portion of the clip-pushing assembly is arranged in the tube body 90, and the clip-pushing assembly is configured to be pushed by the main shaft 1 toward the head end 90A to convey the clip in the clip cartridge into the clamp 11. At least portion of the firing assembly is located in the tube body 90; and the firing assembly is configured to be pushed by the main shaft 1 toward the head end 90A to close the clamp 11, so that the clip in the clamp 11 is fired.

For example, the main-shaft connecting member 2 is sleeved on the main shaft 1 and connected with the main shaft 1. The housing 6 is configured to accommodate at least portion of the main shaft 1 and at least portion of the main-shaft connecting member 2. The main-shaft connecting member 2 is configured to be capable of moving relative to the housing 6 in the axial direction of the tube body 90 (e.g., the Z direction shown in the diagram) and the circumferential direction of the tube body 90 (e.g., the R direction shown in the diagram).

As shown in FIG. 3A, FIG. 3B and FIG. 5, for example, the clip applying mechanism 91 further includes first guiding mechanisms 41a, 41b arranged between the main-shaft connecting member 2 and the housing 6; and the first guiding mechanisms 41a, 41b are configured to guide the main-shaft connecting member 2 to move relative to the housing 6, for example, the main-shaft connecting member 2 is guided to move relative to the housing 6 in the R direction and the Z direction.

As shown in FIG. 3A, FIG. 3B, FIG. 4A to FIG. 4D and FIG. 5, the first guiding mechanism 41a includes a first guiding member 412a arranged on the housing 6 and a first guiding slot 411a arranged on the main-shaft connecting member 2. The first guiding mechanism 41b includes a first guiding member 412b arranged on the housing 6 and a first guiding slot 411b arranged on the main-shaft connecting member 2. The first guiding slot 411a and the first guiding member 412a are engaged with each other, and the first guiding slot 411b and the first guiding member 412b are engaged with each other.

For example, the first guiding members 412a, 412b are both arranged on the second housing portion 62 of the housing 6. In a case where the clip applying mechanism 91 executes respective actions, the second housing portion 62 remains fixed in place, but the main-shaft connecting member 2 moves or rotates relative to the second housing portion 62. By arranging the first guiding slots 411a, 411b on the main-shaft connecting member 2 and arranging the first guiding member 412a on the second housing portion 62, the mutual engagement relationships between the first guiding members 412a, 412b and the first guiding slots 411a, 411b are used to guide a movement path of the main-shaft connecting member 2 in the Z direction or the R direction, so that the main shaft 1 and the main-shaft connecting member 2 can quickly and accurately arrives in place.

According to the embodiment of the present disclosure, the two first guiding mechanisms 41a, 41b may have the same structure or different structures. In a case where the two have a same structure, a fabrication process is simplified, which, thus, is preferred. The embodiments of the present disclosure are illustrated by taking that the two have the same structure as an example. It is described below by taking the first guiding mechanism 41a as an example.

For example, the main-shaft connecting member 2 has an initial state A and a plurality of non-initial states, the plurality of non-initial states include, for example, a clip feeding completion state B, an adjustment state C, a firing completion state D, a retreat state E, and a gyration state F.

According to the embodiment of the present disclosure, the initial state A, the clip feeding completion state B, the adjustment state C, firing completion state D, the retreat state E and the gyration state F of the main-shaft connecting member 2 correspond to the initial state A, the clip feeding completion state B, the adjustment state C, the firing completion state D, the retreat state E and the gyration state F of the clip applying mechanism 91 as described in the foregoing embodiment, and no details will be repeated here.

As shown in FIG. 3A, in a case where the main-shaft connecting member 2 is in the initial state A, the main-shaft connecting member 2 is not applied with any external force, and the first guiding member 412a is located outside the first guiding slot 411a.

In a case where the main-shaft connecting member 2 is respectively in the clip feeding completion state B, the adjustment state C, the firing completion state D, the retreat state E or the gyration state F, the main-shaft connecting member 2 is applied with an external force, so the first guiding member 412a is located in the first guiding slot 411a and moves between different positions in the first guiding slot 411a.

In at least some embodiments, the first guiding slot 411a includes a plurality of different positions, and the plurality of different positions are in one-to-one correspondence with the plurality of different states. In a case where the main-shaft connecting member 2 is in one state of the plurality of different states, the first guiding member 412*a* is located on a position corresponding to the one state of the first guiding slot 411*a*.

As shown in FIG. 6, FIG. 7A, FIG. 8A, FIG. 9A and FIG. 10A, for example, the first guiding slot 411*a* has five different positions: a first position S1, a second position S2, a third position S3, a fourth position S4 and a fifth position S5, which respectively correspond to the clip feeding completion state B, the adjustment state C, the firing completion state D, the retreat state E and the gyration state F.

In a case where the first guiding member 412*a* is located at one position among the first position S1, the second position S2, the third position S3, the fourth position S4 and the fifth position S5, the main-shaft connecting member 2 is in one state corresponding to the above-described position among the clip feeding completion state B, the adjustment state C, firing completion state D, the retreat state E and the gyration state F.

For example, the first guiding slot 411*a* has a plurality of walls which are connected with one another, and a certain angle is formed between two adjacent walls to form the second position S2, the third position S3, the fourth position S4, and the fifth position S5 as described above.

FIG. 12 is a partial structural schematic diagram of the clip applying mechanism according to the embodiment of the present disclosure. As shown in FIG. 12, for example, the first guiding slot 411*a* includes: a first wall W1, a second wall W2, a third wall W3, a fourth wall W4 and a fifth wall W5; two adjacent walls among the first wall W1, the second wall W2, the third wall W3, the fourth wall W4 and the fifth wall W5 form a certain angle to define the second position S2, the third position S3, the fourth position S4 and the fifth position S5. In this way, in a case where the first guiding member 412*a* enters the first guiding slot 411*a*, it is guided by the first wall W1, the second wall W2, the third wall W3, the fourth wall W4 and the fifth wall W5, so that the first guiding member 412*a* sequentially reaches the first position S1, the second position S2, the third position S3, the fourth position S4 and the fifth position S5.

As shown in FIG. 12, for example, the first guiding slot 411*a* further includes a first notch 411*a*1 and a second notch 411*a*2, which are respectively used as an inlet and an outlet of the first guiding slot 411*a*. That is, the first guiding member 412*a* enters the first guiding slot 411*a* from the first notch 411*a*1, and leaves the first guiding slot 411*a* from the second notch 411*a*2.

As described above, in a case where the main-shaft connecting member 2 switches from the adjustment state C to the firing completion state D, the main-shaft connecting member 2 rotates along the first rotation direction +R by the angle a1; in a case where the main-shaft connecting member 2 switches from the retreat state E to the gyration state F, the main-shaft connecting member 2 gyrates along the second rotation direction –R by the angle a2. If the first guiding slot 411*a* has only one notch (for example, has only the first notch 411*a*1) and the notch serves as both an inlet and an outlet, it means that the main-shaft connecting member 2 needs to gyrate by the angle a2 which is equal to the angle a1 of rotation, so as to leave from the first notch 411*a*1. However, such a setting mode is easy to cause the first locking members 211*a*, 211*b* to be locked again with the second locking members 212*a*, 212*b* while the main-shaft connecting member 2 has not returned to the initial position.

Therefore, according to the embodiment of the present disclosure, by arranging the first guiding slot to have two notches which are respectively used as the inlet and the outlet, it avoids being wrongly locked by the locking mechanism during a process of resetting the main-shaft connecting member 2.

As shown in FIG. 12, the first notch 411*a*1 and the second notch 411*a*2 are both located on a same side of the first guiding slot 411*a* that is proximal to the head end 90A. In this way, it is more favorable for reset of the main-shaft connecting member 2.

As shown in FIG. 3A, FIG. 6 and FIG. 12, in a case where the clip applying mechanism 91 switches from the initial state A to the clip feeding completion state B, the main-shaft connecting member 2 is applied with an external force to move along the +Z direction. During the moving process of the main-shaft connecting member 2, the first guiding member 412*a* enters the first guiding slot 411*a* from the first notch 411*a*1; the first wall W1 guides the first guiding member 412*a* to the first position S1 shown in FIG. 6, so that the main-shaft connecting member 2 switches from the initial state A to the clip feeding completion state B.

As shown in FIG. 7A, FIG. 7B and FIG. 12, in a case where the clip applying mechanism 91 switches from the clip feeding completion state B to the adjustment state C, the main-shaft connecting member 2 is applied with an external force to continue to move along the +Z direction. The first wall W1 guides the first guiding member 412*a* from the first position S1 to the second position S2, so that the main-shaft connecting member 2 switches from the clip feeding completion state B to the adjustment state C.

For example, an extension direction of the second wall W2 is different from an extension direction of the first wall W1; the second position S2 is located at a junction of the first wall W1 and the second wall W2, so that the first guiding member 412*a* is limited to the second position S2 through the second wall W2.

As shown in FIG. 8A, FIG. 8B and FIG. 12, in a case where the clip applying mechanism 91 switches from the adjustment state C to the firing completion state D, the main-shaft connecting member 2 is applied with an external force to continue to move along the +Z direction. The second wall W2 guides the first guiding member 412*a* from the second position S2 to the third position S3. Because an extension direction of the third wall W3 is different from an extension direction of the second wall W2, a movement direction of the first guiding member 412*a* in the first guiding slot 411*a* is changed, and thus the main-shaft connecting member 2 rotates along the first rotation direction +R by the angle a1 at the same time of moving along the +Z direction. Finally, the main-shaft connecting member 2 switches from the adjustment state C to the firing completion state D.

For example, the extension direction of the third wall W3 is different from the extension direction of the second wall W2, and the third position S3 is located between the second wall W2 and the third wall W3, so that the first guiding member 412*a* is limited to the third position S3 through the third wall W3.

For example, in FIG. 12, a gap is provided between the second wall W2 and the third wall W3. It may be understood that in other embodiments, the second wall W2 and the third wall W3 may be connected with each other to better define the third position.

As shown in FIG. 9A, FIG. 9B and FIG. 12, in a case where the clip applying mechanism 91 switches from the firing completion state D to the retreat state E, the main-shaft connecting member 2 is applied with an external force to move along the –Z direction. The third wall W3 guides the first guiding member 412*a* from the third position S3 to the fourth position S4, so that the main-shaft connecting member 2 switches from the firing completion state D to the retreat state E.

For example, an extension direction of the fourth wall W4 is different from the extension direction of the third wall W3, and the fourth position S4 is located at a junction of the third wall W3 and the fourth wall W4, so that the first guiding member 412a is limited to the fourth position S4 through the fourth wall W4.

As shown in FIG. 10A, FIG. 10B and FIG. 12, in a case where the clip applying mechanism 91 switches from the retreat state E to the gyration state F, under a reset force of the first spring 13a, the main-shaft connecting member 2 moves along the −Z direction, and the fourth wall W4 guides the first guiding member 412a from the fourth position S4 to the fifth position S5. Because an extension direction of the fifth wall W5 is different from the extension direction of the fourth wall W4, a movement direction of the first guiding member 412a in the first guiding slot 411a is changed, and thus the main-shaft connecting member 2 rotates along the second rotation direction −R by the angle a2 at the same time of moving along the −Z direction. For example, the angle a2 is less than the angle a1. Finally, the main-shaft connecting member 2 switches from the retreat state E to the gyration state F.

As shown in FIG. 3A and FIG. 12, in a case where the clip applying mechanism 91 switches from the gyration state F to the initial state A, the main-shaft connecting member 2 continues to move along the −Z direction under an action of the reset force of the second spring 13b; in this situation, the fifth wall W5 guides the first guiding member 412a from the fifth position S5 to the outside of the first guiding slot 411a, so that the first guiding member 412a leaves the first guiding slot 411a from the second notch 411a2. Because the first guiding member 412a leaves the first guiding slot 411a, the main-shaft connecting member 2 continues to rotate by the angle a3 along the second rotation direction −R, and finally recovers from the gyration state F to the initial state A.

According to the embodiment of the present disclosure, by arranging the fifth wall W5, the first guiding member 412a moves a certain distance in the Z direction, which effectively prevent the first locking member and the second locking member from being locked with each other in the reset process of the clip applying mechanism. It may be understood that in other embodiments, the first guiding slot 411a may not include the fifth wall W5, that is, the second notch 411a2 is located at the fifth position S5, in this case, the fourth wall W4 is capable of directly guiding the first guiding member 412a from the fourth position S4 to the outside of the first guiding slot 411a, which can also achieve the purpose of the present disclosure.

As shown in FIG. 12, for example, an extension direction of each of the first wall W1, the third wall W3 and the fifth wall W5 is substantially parallel to the Z direction, which is favorable for guiding movement of the main-shaft connecting member 2 in the Z direction.

According to the embodiment of the present disclosure, the term "substantially parallel" refers to being generally parallel or being basically parallel, allowing process errors or measurement errors. According to the embodiment of the present disclosure, the term "approximately" is understood as not strictly requiring the numerical limit, allowing a value within a range of process errors or measurement errors.

As shown in FIG. 12, for example, an extension direction of each of the second wall W2 and the fourth wall W4 is tilted relative to the Z direction, which is favorable for guiding movement of the main-shaft connecting member 2 in the Z direction and rotation in the R direction.

As shown in FIG. 12, for example, there is a first tilt angle b1 between the second wall W2 and the Z direction, and there is a second tilt angle b2 between the fourth wall W4 and the Z direction, for example, the first tilt angle b1 is greater than the second tilt angle b2. By arranging the first tilt angle b1 greater than the second tilt angle b2, the main-shaft connecting member 2 is prevented from being locked by the locking mechanism during the reset process.

According to the embodiment of the present disclosure, values of the first tilt angle b1 and the second tilt angle b2 are related to friction coefficients of the first guiding member 412a with respect to the second wall W2 and the fourth wall W4, which is determined by those skilled in the art according to actual needs.

For example, the first tilt angle b1 is 10° to 70°, and the second tilt angle b2 is 10° to 70°. If the first tilt angle b1 and the second tilt angle b2 are less than 10°, although it is easier to guide the main-shaft connecting member 2 by using the first guiding members 412a, 412b, a total length of the main-shaft connecting member 2 will become longer, and the entire device will also become longer. If the first tilt angle b1 and the second tilt angle b2 are greater than 70°, the first guiding members 412a, 412b may be stuck and self-locked, thereby being incapable of guiding the main-shaft connecting member 2.

According to the embodiment of the present disclosure, in order to increase the smoothness of sliding of the first guiding member 412a in the first guiding slot 411a, the second wall W2 and the fourth wall W4 are set as helical surfaces spiral along the tubular member 20 of the main-shaft connecting member 2, the above-described first tilt angle b1 is a helix angle of the second wall W2, and the above-described second tilt angle b2 is a helix angle of the fourth wall W4.

According to the embodiment of the present disclosure, the clip may be made of various materials, and the clip may also be designed to have different sizes according to specific materials. A length of the first guiding slots 411a, 411b is determined according to the material and the size of the clip. For example, the clip is made of an absorbable material or a non-absorbable material, and the non-absorbable material includes but is not limited to plastic or metal. In a case where the clip is a plastic clip, if a length of the plastic clip is relatively long, a firing distance of the plastic clip is relatively long (approximately 10 mm); so, the length of the first guiding slots 411a, 411b should be set to be relatively long. In a case where the clip is a metal clip (for example, a titanium clip), if a length of the titanium clip is relatively short, a firing distance of the titanium clip is relatively short (approximately 6 mm), and the length of the first guiding slots 411a, 411b should be set to be relatively short.

As shown in FIG. 12, for example, the first guiding mechanism 41a further includes a spacing wall W0 arranged in the first guiding slot 411a; and the spacing wall W0 extends along the Z direction to define the first notch 411a1 and the second notch 411a2. By arranging the spacing wall W0 in the first guiding slot 411a, it is more favorable for forming the first notch 411a1 and the second notch 411a2.

The embodiments of the present disclosure are described by taking two first guiding mechanisms 41a, 41b as an example; and it may be understood that the total number of first guiding mechanisms may be one or more than two, for example, three, etc., which will not be limited in the embodiments of the present disclosure.

In a case where the total number of first guiding mechanisms is plural, the plurality of guiding mechanisms are arranged between the main-shaft connecting member 2 and the housing 6 along the circumferential direction of the main-shaft connecting member 2 at equal interval, so that the force endured by the main-shaft connecting member 2 or the housing 6 is uniform, and thereby increasing an effect of locking in place.

For example, the main-shaft connecting member 2 is a tubular member 20, and the two first guiding mechanisms 41a, 41b are symmetrically arranged in the radial direction of the tubular member 20; in this way, the total number of first guiding mechanisms may be reduced as much as possible, the fabrication costs is saved, and the manufacturing difficulty is reduced, under the condition of ensuring a uniform force endured by the main-shaft connecting member 2 or the housing 6.

As shown in FIG. 4A, FIG. 4C and FIG. 5, the clip applying mechanism 91 further includes second guiding mechanisms 42a, 42b arranged between the main-shaft connecting member 2 and the housing 6; and the second guiding mechanisms 42a, 42b are different from the first guiding mechanisms 41a, 41b.

According to the embodiment of the present disclosure, the second guiding mechanisms 42a, 42b are different from the first guiding mechanisms 41a, 41b in both structure and position.

For example, the second guiding mechanism 42a includes a second guiding member 422a arranged on the housing 6 and a second guiding slot 421a arranged on the main-shaft connecting member 2; the second guiding mechanism 42b includes a second guiding member 422b arranged on the housing 6 and a second guiding slot 421b arranged on the main-shaft connecting member 2.

For example, on the main-shaft connecting member 2, positions of the second guiding slots 421b a, 421b are different from the positions of the first guiding slots 411a, 411b. The positions of the second guiding members 422a, 422b on the housing 6 are also different from the positions of the first guiding members 412a, 412b on the housing 6.

According to the embodiment of the present disclosure, the two second guiding mechanisms 42a, 42b may have the same structure or different structures. In a case where the two have the same structure, a fabrication process is simplified, which, thus, is preferred. The embodiments of the present disclosure are described by taking that the two have the same structure as an example.

As shown in FIG. 4A, an opening direction of the notch of the first guiding slot 411a is the +Z direction, while an opening direction of the notch of the second guiding slot 421a is the −Z direction, so the opening direction of the notch of the second guiding slot 421a is opposite to the opening direction of the notch of the first guiding slot 411a. By arranging the second guiding mechanism and arranging the opening directions of the first guiding slot 411a and the second guiding slot 421a opposite to each other, it is favorable for guiding the main-shaft connecting member 2 to recover from the gyration state F to the initial state A.

For example, in a case where the main-shaft connecting member 2 recovers from the gyration state F to the initial state A, the first guiding member 412a leaves the first guiding slot 411a. If the second guiding mechanism is not arranged, the gyration angle of the main-shaft connecting member 2 loses control, thus the actual gyration angle may be greater than the angle a3.

According to the embodiment of the present disclosure, by arranging the second guiding mechanism, the second guiding member 422a enters the second guiding slot 421a during the process that the main-shaft connecting member 2 recovers from the gyration state F to the initial state A. Because the second guiding slot 421a is capable of defining a movement direction of the second guiding member 422a, the main-shaft connecting member 2 is guided to continue to rotate by the angle a3 along the second rotation direction −R while moving in the −Z direction, finally the main-shaft connecting member 2 recovers from the gyration state F to the initial state A.

The embodiments of the present disclosure are described by taking two first guiding mechanisms 42a, 42b as an example, it may be understood that the total number of first guiding mechanisms may be one or more than two, for example, three, etc., which will not be limited in the embodiments of the present disclosure.

In a case where the total number of first guiding mechanisms is plural, the plurality of guiding mechanisms are arranged between the main-shaft connecting member 2 and the housing 6 along the circumferential direction of the main-shaft connecting member 2 at equal interval, so that the force endured by the main-shaft connecting member 2 or the housing 6 is uniform, thereby enhancing the guiding effect.

For example, the main-shaft connecting member 2 is a tubular member 20, and the two first guiding mechanisms 42a, 42b are symmetrically arranged in the radial direction of the tubular member 20, in this way, the total number of first guiding mechanisms may be reduced as much as possible, the fabrication costs is saved, and the manufacturing difficulty is reduced, under the condition of ensuring a uniform force endured by the main-shaft connecting member 2 or the housing 6.

In the clip applying apparatus, the main-shaft connecting member moves to different positions under an action of the external force; during the moving process, a movement direction of the main-shaft connecting member is guided through the guiding mechanism. After a period of use, the guiding slot or the guiding member may possibly abrade, so as to affect switching of the main-shaft connecting member between different positions.

To this end, still another embodiment of the present disclosure provides a clip applying mechanism of a clip applying apparatus, which at least aims to assist the main-shaft connecting member to be capable of switching quickly between different positions, so as to further ensure stability and safety of the clip applying mechanism in operation.

For example, the clip applying mechanism of the clip applying apparatus provided by still another embodiment of the present disclosure includes: a tube body, a main shaft, a clip-cartridge assembly, a clip-pushing assembly and a firing assembly. The tube body includes a head end and a tail end opposite to each other; the main shaft is arranged proximal to the tail end and at least portion of the main shaft is arranged in the tube body; the clip-cartridge assembly is configured to penetrate through the tube body and includes: a clip cartridge arranged in the tube body and an end effector configured to penetrate out of the head end; the clip cartridge is configured to be filled with a clip; at least portion of the clip-pushing assembly is arranged in the tube body, and the clip-pushing assembly is configured to be pushed by the main shaft toward the head end to convey the clip in the clip cartridge into the end effector; at least portion of the firing assembly is located in the tube body, and the firing assembly is configured to be pushed by the main shaft toward the head end to close the end effector, so that the clip in the end effector is fired. Further, the clip applying mechanism further includes: a main-shaft connecting member, a housing and a limiting mechanism. The main-shaft connecting member is sleeved on the main shaft and connected with the main shaft; the housing is configured to accommodate the main shaft and the main-shaft connecting member, herein, the main-shaft connecting member is configured to be capable of moving relative to the housing in an axial direction of the tube body and an circumferential direction of the tube body; the limiting mechanism is arranged between the main-shaft connecting member and the housing, and the limiting mechanism is configured to limit a movement range of the main-shaft connecting member relative to the housing.

In the above-described clip applying mechanism provided by the embodiment of the present disclosure, by arranging the limiting mechanism between the main-shaft connecting member and the housing, the movement range of the main-shaft connecting member in the housing is limited, thereby assisting the main-shaft connecting member to switch between different positions, so as to further ensure stability and safety of the clip applying mechanism in operation.

Hereinafter, the above-described clip applying mechanism and clip applying apparatus will be described with reference to FIG. 1A to FIG. 12. In order to maintain clarity and conciseness of the present disclosure, components mentioned in the following embodiments that are the same as those in the foregoing embodiments will not be described repeatedly, and the description in the foregoing embodiments may be referred to for related structures and setting modes thereof.

As shown in FIG. 1A, FIG. 1B and FIG. 2, the clip applying apparatus 900 provided by still another embodiment of the present disclosure includes a clip applying mechanism 91 and a handle assembly 92.

For example, the clip applying mechanism 91 is detachably connected with the handle assembly 92. The clip applying mechanism 91 includes a tube body 90, a main shaft 1, a main-shaft connecting member 2, a firing connecting member 3, a clip-cartridge assembly, a clip-pushing assembly, a firing assembly, a housing 6, a pushing rod 7, and an end cap 12. The firing assembly includes, for example, a firing rod 4 and a firing sleeve 5. The clip-cartridge assembly includes, for example, a clip cartridge 9 and a clamp 11 (also referred to as an end effector). The clip-pushing assembly includes, for example, a pushing block 8 and a clip pushing piece 10.

For example, the tube body 90 includes a head end 90A and a tail end 90B opposite to each other. The main shaft 1 is arranged proximal to the tail end 90B and at least portion of the main shaft 1 is arranged in the tube body 90. The clip-cartridge assembly penetrates through the tube body 90 and includes: a clip cartridge arranged in the tube body 90 and a clamp 11 penetrating out of the head end 90A. The clip cartridge is configured to be filled with a clip. At least portion of the clip-pushing assembly is arranged in the tube body 90, and the clip-pushing assembly is configured to be pushed by the main shaft 1 toward the head end 90A to convey the clip in the clip cartridge into the clamp 11. At least portion of the firing assembly is located in the tube body 90, and the firing assembly is configured to be pushed by the main shaft 1 toward the head end 90A to close the clamp 11, so that the clip in the clamp 11 is fired.

For example, the main-shaft connecting member 2 is sleeved on the main shaft 1 and connected with the main shaft 1. The housing 6 is configured to accommodate at least portion of the main shaft 1 and at least portion of the main-shaft connecting member 2, The main-shaft connecting member 2 is configured to be capable of moving relative to the housing 6 in the axial direction of the tube body 90 (e.g., the Z direction shown in the diagram) and the circumferential direction of the tube body 90 (e.g., the R direction shown in the diagram).

For example, the clip applying mechanism 91 further includes limiting mechanisms 51a, 51b arranged between the main-shaft connecting member 2 and the housing 6; the limiting mechanisms 51a, 51b are configured to limit a movement range of the main-shaft connecting member 2 relative to the housing 6.

As shown in FIG. 5 and FIG. 12, the limiting mechanism 51a includes a limiting protrusion 511a arranged on the main-shaft connecting member 2 and a limiting slot 512a arranged on the housing 6. The limiting mechanism 51b (not shown) includes a limiting protrusion 511b arranged on the main-shaft connecting member 2 and a limiting slot 512b (not shown) arranged on the housing 6. The limiting protrusion 511a moves in the limiting slot 512a, and the limiting protrusion 511b moves in the limiting slot 512b.

For example, the limiting slots 512a, 512b are both arranged on the second housing portion 62 of the housing 6. In a case where the clip applying mechanism 91 executes respective actions, the second housing portion 62 remains fixed in place, and the main-shaft connecting member 2 moves or rotates relative to the second housing portion 62. By arranging the limiting slots 512a, 512b on the second housing portion 62 and arranging the limiting protrusions 511a, 511b on the main-shaft connecting member 2, the movement range of the main-shaft connecting member 2 within the housing 6 is limited by using the engagement relationship between the limiting protrusions 511a, 511b and the limiting slots 512a, 512b, thereby assisting the main-shaft connecting member 2 to switch between different positions, so as to further ensure stability and safety of the clip applying mechanism 91 in operation.

According to the embodiment of the present disclosure, the two limiting mechanisms 51a, 51b may have the same structure or different structures. In a case where the two have the same structure, a fabrication process is simplified, which, thus, is preferred. The embodiments of the present disclosure are described by taking that the two have the same structure as an example. Hereinafter, it is described by taking the limiting mechanism 51a as an example.

As shown in FIG. 5, for example, in the limiting mechanism 51a, the limiting slot 512a includes a first limiting sub-slot 512a1 and a second limiting sub-slot 512a2. The second limiting sub-slot 512a2 is connected with the first limiting sub-slot 512a1 and is arranged more proximal to the head end than the first limiting sub-slot 512a1. The first limiting sub-slot 512a1 is configured to limit movement of the limiting protrusion 511a in the Z direction, and the second limiting sub-slot 512a2 is configured to limit movement of the limiting protrusion 511a in the Z direction and/or the R direction.

As shown in FIG. 5, for example, an extension direction of the first limiting sub-slot 512a1 is parallel to the Z direction, that is, a length direction of the first limiting sub-slot 512a1 is parallel to the Z direction; an extension direction of the second limiting sub-slot 512a2 is parallel to the Z direction, that is, a length direction of the second limiting sub-slot 512a2 is parallel to the Z direction. For example, the first limiting sub-slot 512a1 has a first width $a1w$ in the R direction, and the second limiting sub-slot 512a2 has a second width $a2w$ in the R direction. The second width $a2w$ is greater than the first width $a1w$, so that the limiting protrusion 511a is capable of moving in the second limiting sub-slot 512a2 simultaneously along the Z direction and the R direction.

As shown in FIG. 3A, FIG. 5 and FIG. 6, in a case where the main-shaft connecting member 2 switches from the initial state A to the clip feeding completion state B, the limiting protrusion 511a moves in the first limiting sub-slot 512a1 along the +Z direction; and in this situation, the limiting protrusion 511a only moves along the +Z direction but does not rotate in the R direction.

For example, a width of the limiting protrusion 511a in the R direction is approximately equal to the first width a1w of the first limiting sub-slot 512a1, which prevents limiting protrusion 511a from sliding out of the first limiting sub-slot 512a1.

As shown in FIG. 5 and FIG. 7A, in a case where the main-shaft connecting member 2 switches from the clip feeding completion state B to the adjustment state C, the limiting protrusion 511a continues to move along the +Z direction and enters the second limiting sub-slot 512a2 from the first limiting sub-slot 512a1.

As shown in FIG. 5 and FIG. 8A, in a case where the main-shaft connecting member 2 switches from the adjustment state C to the firing completion state D, the limiting protrusion 511a moves in the second limiting sub-slot 512a2 in the +Z direction and simultaneously rotates along the first rotation direction +R by the angle a1. In the process, because the second width a2w of the second limiting sub-slot 512a2 is greater than the first width a1w of the first limiting sub-slot 512a1, the limiting protrusion 511a rotates along the +R direction while moving in the +Z direction.

As shown in FIG. 5 and FIG. 9A, in a case where the main-shaft connecting member 2 switches from the firing completion state D to the retreat state E, the limiting protrusion 511a moves in the second limiting sub-slot 512a2 along the −Z direction.

As shown in FIG. 5 and FIG. 10A, in a case where the main-shaft connecting member 2 switches from the retreat state E to the gyration state F, the limiting protrusion 511a continues to move along the −Z direction and simultaneously rotates along the second rotation direction −R by the angle a2, to move out of the second limiting sub-slot 512a2.

As shown in FIG. 3A and FIG. 5, in a case where the main-shaft connecting member 2 recovers from the gyration state F to the initial state A, the limiting protrusion 511a continues to move along the −Z direction and simultaneously continues to rotate along the second rotation direction −R by the angle a3, so as to moves back into the first limiting sub-slot 512a1. In this situation, the limiting protrusion 511a returns to the initial position.

As shown in FIG. 5, the second limiting sub-slot 512a2 includes a first side wall 5121 and a second side wall 5122 opposite to each other in the Z direction; the first side wall 5121 is proximal to the head end 90A, and the second side wall 5122 is distal to the head end 90A. At least one of the first side wall 5121 and the second side wall 5122 is arranged obliquely relative to a bottom surface of the second limiting sub-slot 512a2. For example, in FIG. 5, the second side wall 5122 is arranged obliquely relative to the bottom surface of the second limiting sub-slot 512a2 to form a slope surface, so that in a case where the limiting protrusion 511a moves out of the second limiting sub-slot 512a2, it prevents the limiting protrusion 511a from being stuck at the second side wall 5122.

As shown in FIG. 12, for example, the main-shaft connecting member 2 further includes elastic members 513a, 513b, the elastic members 513a, 513b are arranged on a side of the main-shaft connecting member 2 facing toward the housing 6 and are configured to be capable of producing elastic deformation in the radial direction of the main-shaft connecting member 2. For example, the limiting protrusions 511a, 511b are respectively arranged on the elastic members 513a, 513b. By arranging the elastic members 513a, 513b on the main-shaft connecting member 2, the limiting protrusions 511a, 511b have certain displacement space in the radial direction of the main-shaft connecting member 2, which is favorable for the limiting protrusions 511a, 511b to keep tightly engaged with the limiting slots 512a, 512b.

For example, in a case where depths of the first limiting sub-slot 512a1 and the second limiting sub-slot 512a2 are different from each other, the limiting protrusion 511a keep full contact respectively with the first limiting sub-slot 512a1 and the second limiting sub-slot 512a2 through the elastic member 513a, so as to implement tight engagement.

As shown in FIG. 12, the main-shaft connecting member 2 is a tubular member 20. The elastic member 513b protrudes from a side of the tubular member 20 facing toward the housing 6 and includes a hollow portion 514b. By arranging the hollow portion 514b in the elastic member 513b, elastic space of the elastic member 513b is further increased. It may be understood that FIG. 12 only shows the hollow portion 514b of the elastic member 513b, and the elastic member 513a also has the same hollow portion.

The embodiments of the present disclosure are described by taking two limiting mechanisms 51a, 51b as an example, it may be understood that the total number of limiting mechanisms may be one or more than two, for example, three, etc., which will not be limited in the embodiments of the present disclosure.

In a case where the total number of limiting mechanisms is plural, the plurality of limiting mechanisms are arranged between the main-shaft connecting member 2 and the housing 6 along the circumferential direction of the main-shaft connecting member 2 at equal internal, so that the force endured by the main-shaft connecting member 2 or the housing 6 is uniform, thereby enhancing the limiting effect.

For example, the main-shaft connecting member 2 is a tubular member 20, and the two limiting mechanisms 51a, 51b are symmetrically arranged in the radial direction of the tubular member 20, in this way, the total number of first guiding mechanisms may be reduced as much as possible, the fabrication costs is saved, and the manufacturing difficulty is reduced, under the condition of ensuring a uniform force endured by the main-shaft connecting member 2 or the housing 6.

For example, as shown in FIG. 1A and FIG. 3 to FIG. 3C, the pushing rod 7 is located in the handle assembly 92 and is configured to be detachably connected with the main-shaft connecting member 2; the pushing rod 7 is configured to drive the main shaft 1 and the main-shaft connecting member 2 to move in the Z direction, for example, move in the +Z direction or the −Z direction. By providing the detachable connection between the pushing rod 7 and the main-shaft connecting member 2, the clip applying mechanism 91 is quickly detached from the handle assembly 92, which is favorable for replacing the clip applying mechanism 91 with another clip applying mechanism that is filled with clips of different size.

As shown in FIG. 3C and FIG. 7C, for example, the clip applying mechanism 91 further includes engagement mechanisms 52a, 52b arranged between the main-shaft connecting member 2 and the pushing rod 7. The engagement mechanism 52a includes a pin 521a arranged on the main-shaft connecting member 2 and a slot 522a arranged on the pushing rod 7; and the pin 521*a* is configured to be engaged with the slot 522*a*, to implement connection between the pushing rod 7 and the main-shaft connecting member 2.

According to the embodiment of the present disclosure, the two engagement mechanisms 52*a*, 52*b* may have the same structure or different structures. In a case where the two have the same structure, a fabrication process is simplified, which, thus, is preferred. The embodiments of the present disclosure are described by taking that the two have the same structure as an example. Hereinafter, it is described by taking the engagement mechanism 52*a* as an example.

For example, the engagement mechanism 52*a* has a separate state, a release state, and a lock state. In the separate state, the pin 521*a* and the slot 522*a* are separated from each other, and the pin 521*a* is located outside the slot 522*a*. In the release state, the pin 521*a* is located in the slot 522*a* and is capable of moving out of the slot 522*a*. In the lock state, the pin 521*a* and the slot 522*a* are locked with each other.

FIG. 13 is a structural schematic diagram of the engagement mechanism according to the embodiment of the present disclosure. As shown in FIG. 13, for example, the slot 522*a* includes a release position 522*p*1 and a lock position 522*p*2, and the pin 521*a* is capable moving between the release position 522*p*1 and the lock position 522*p*2.

For example, in a case where the engagement mechanism is in the lock state, the pin 521*a* is in the lock position 522*p*2. In a case where the engagement mechanism is in the release state, the pin 521*a* is in the release position 522*p*1 and is capable of moving out of the slot 522*a*. In a case where the engagement mechanism is in the separate state, the pin 521*a* is located outside the slot 522*a*, that is, it is neither located in the release position 522*p*1, nor located in the lock position 522*p*2.

As shown in FIG. 3 to FIG. 3C, in a case where the clip applying mechanism 91 is in the initial state A, the engagement mechanism 52*a* is in the separate state. As shown in FIG. 6, FIG. 7C and FIG. 10C, in a case where the clip applying mechanism 91 is in the clip feeding completion state B, the adjustment state C or the gyration state F, the engagement mechanism 52*a* is in the release state. As shown in FIG. 8C and FIG. 9C, in a case where the clip applying mechanism 91 is in the firing completion state D or the retreat state E, the engagement mechanism 52*a* is in the lock state.

After the clip is fired (i.e., in the firing completion state D or the retreat state E), the engagement mechanism 52*a* is in the lock state, and the pushing rod 7 and the main-shaft connecting member 2 are locked with each other. Then, an external force is applied to the main-shaft connecting member 2 to enable the main-shaft connecting member 2 move in the –Z direction, and thus the pushing rod 7 retreats in the –Z direction under the drive of the main-shaft connecting member 2. By arranging the engagement mechanism 52*a* to be in the lock state in the firing completion state D and the retreat state E, it may be ensured that at least in the firing process and retreating process, the pushing rod 7 and the main-shaft connecting member 2 will not be separated from each other, so as to avoid accidents occurring in the above-described two processes.

The embodiments of the present disclosure are described by taking two engagement mechanisms 52*a*, 52*b* as an example, it may be understood that the total number of engagement mechanisms may be one or more than two, for example, three, etc., which will not be limited in the embodiments of the present disclosure.

In a case where the total number of engagement mechanisms is plural, the plurality of engagement mechanisms are arranged between the main-shaft connecting member 2 and the pushing rod 7 along the circumferential direction of the main-shaft connecting member 2 at equal interval, so that the force endured by the main-shaft connecting member 2 or the pushing rod 7 is uniform, thereby enhancing the engagement effect.

For example, the main-shaft connecting member 2 is a tubular member 20, and the two engagement mechanisms 52*a*, 52*b* are symmetrically arranged in the radial direction of the tubular member 20, in this way, the total number of engagement mechanisms may be reduced as much as possible, the fabrication costs is saved, and the manufacturing difficulty is reduced, under the condition of ensuring a uniform force on the main-shaft connecting member 2 or the pushing rod 7.

As shown in FIG. 3D, the tubular member 20 includes a first tubular portion 2A and the second tubular portion 2B in the Z direction. Inner diameters of the first tubular portion 2A and the second tubular portion 2B are different, so that the first tubular portion 2A and the second tubular portion 2B respectively accommodate different components.

For example, the first tubular portion 2A and the second tubular portion 2B are connected with each other, the first tubular portion 2A is proximal to the head end 90A, the second tubular portion 2B is distal to the head end 90A. An inner diameter of the first tubular portion 2A is greater than an inner diameter of the second tubular portion 2B, so that the first tubular portion 2A accommodates the main shaft 1, the firing connecting member 3 and the firing rod 4, but the second tubular portion 2B accommodates only the main shaft 1 and the pushing rod 7. By providing the first tubular portion 2A and the second tubular portion 2B with different inner diameters, the main-shaft connecting member 2 is connected with the pushing rod 7 without affecting positions and relative movement of other components.

In the above-described clip applying mechanism and clip applying apparatus provided by the embodiments of the present disclosure, at least one of the following advantageous effects is achieved:

1) By arranging the main-shaft connecting member connected with the main shaft and arranging the locking mechanism between the main-shaft connecting member and the housing, it is ensured that the main-shaft connecting member and the housing are locked with each other through the locking mechanism in a case where the clip is conveyed to the end effector, thereby avoiding damage to the end effector while the clip applying mechanism is used again.

2) By arranging the main-shaft connecting member connected with the main shaft and the firing connecting member respectively connected with the main-shaft connecting member and the firing assembly, the main-shaft connecting member, the engagement mechanism and the firing connecting member are used to pull the firing assembly back in the direction facing away from the head end after the clip is fired, which is favorable for reset of the firing sleeve so as to avoid impact on subsequent actions.

3) By arranging the first guiding mechanism between the main-shaft connecting member and the housing, the main-shaft connecting member is guided by the first guiding mechanism during the moving or rotating process; because the main-shaft connecting member is also connected with the main shaft, it is ensured that both the main shaft and the main-shaft connecting member quickly and accurately arrives in place in a case where the clip applying mechanism executes respective actions.

4) By arranging the limiting mechanism between the main-shaft connecting member and the housing, the movement range of the main-shaft connecting member in the housing is limited, thereby assisting the main-shaft connecting member to switch between different positions, so as to further ensure stability and safety of the clip applying mechanism in operation.

In the disclosure, the following should be noted:

(1) The accompanying drawings involve only the structure(s) in connection with the embodiment(s) of the present disclosure, and other structure(s) can be referred to common design(s).

(2) For the purpose of clarity only, in accompanying drawings for illustrating the embodiment(s) of the present disclosure, the thickness and a size of a layer or area may be enlarged or narrowed, that is, the drawings are not drawn in a real scale.

(3) In case of no conflict, features in one embodiment or in different embodiments can be combined as a new embodiment.

The above described are only specific embodiments of the present disclosure, and the scope of the present disclosure is not limited to this. For those skilled in the art, various changes and alternations may be readily contemplated without departing from the technical scope of the present disclosure, and all of these changes and alternations shall fall within the scope of the present disclosure. Therefore, the scope of the present disclosure shall be defined by the scope of the claims.

The invention claimed is:

1. A clip applying mechanism of a clip applying apparatus, comprising:

a tube body, comprising a head end and a tail end opposite to each other;

a main shaft, the main shaft being arranged proximal to the tail end and at least portion of the main shaft being arranged in the tube body;

a clip-cartridge assembly, the clip-cartridge assembly being configured to penetrate through the tube body and comprising: a clip cartridge arranged in the tube body and an end effector configured to penetrate out of the head end; the clip cartridge being configured to be filled with a clip;

a clip-pushing assembly, at least portion of the clip-pushing assembly being arranged in the tube body, and the clip-pushing assembly being configured to be pushed by the main shaft toward the head end to convey the clip in the clip cartridge into the end effector; and a firing assembly, at least portion of the firing assembly being located in the tube body, and the firing assembly being configured to be pushed by the main shaft toward the head end to close the end effector, so that the clip in the end effector is fired;

wherein the clip applying mechanism further comprises:

a main-shaft connecting member, connected with the main shaft;

a firing connecting member, connected with the firing assembly;

an engagement mechanism, arranged between the main-shaft connecting member and the firing connecting member;

wherein the engagement mechanism, the firing connecting member, the main-shaft connecting member and the firing assembly are configured such that: in a case where the clip is fired, the main-shaft connecting member drives the firing connecting member to move in a direction facing away from the head end through the engagement mechanism, and the firing connecting member drives the firing assembly to move in a same direction, so that the end effector is partially opened, wherein a first engagement member comprises a pin; a second engagement member comprises a slot, the slot comprises a release position and a lock position, the pin is configured to be capable of moving between the release position and the lock position; the slot and the pin are configured such that: in a case where the engagement mechanism is in a lock state, the pin is in the lock position; in a case where the engagement mechanism is in a release state, the pin is in the release position and is capable of moving out of the slot; in a case where the engagement mechanism is in a separate state, the pin is located outside the slot.

2. The clip applying mechanism of the clip applying apparatus according to claim 1, wherein the engagement mechanism comprises: the first engagement member, arranged on the main-shaft connecting member; the second engagement member, arranged on the firing connecting member; in the release state, the first engagement member is located in the second engagement member and is capable of moving out of the second engagement member; and in the lock state, the first engagement member and the second engagement member are locked with each other.

3. The clip applying mechanism of the clip applying apparatus according to claim 2, wherein:

the clip applying mechanism has a firing completion state and a retreat state; in the firing completion state, the clip in the end effector is fired; in the retreat state, there is no clip in the end effector, and the main-shaft connecting member is applied with an external force to retreat;

the engagement mechanism is configured such that: in a case where the clip applying mechanism is in the firing completion state or the retreat state, the engagement mechanism is in the lock state.

4. The clip applying mechanism of the clip applying apparatus according to claim 2, wherein:

the clip applying mechanism has a clip feeding completion state and a gyration state; in the clip feeding completion state, the clip has been conveyed into the end effector;

the engagement mechanism is configured such that: in a case where the clip applying mechanism is in the clip feeding completion state or the gyration state, the engagement mechanism is in the release state.

5. The clip applying mechanism of the clip applying apparatus according to claim 2, wherein the engagement mechanism further has a separate state; in the separate state, the first engagement member and the second engagement member are separated from each other, and the first engagement member is located outside the second engagement member.

6. The clip applying mechanism of the clip applying apparatus according to claim 5, wherein:

the clip applying mechanism further has an initial state; in the initial state, neither the main shaft nor the main-shaft connecting member is applied with an external force;

the engagement mechanism is configured such that: in a case where the clip applying mechanism is in the initial state, the clip applying mechanism is in the separate state.

7. The clip applying mechanism of the clip applying apparatus according to claim 1, wherein the firing connecting member is a tubular member, the slot is a through slot arranged on the tubular member; a notch of the slot is open toward the direction facing away from the head end, and the release position is located at a bottom of the slot.

8. The clip applying mechanism of the clip applying apparatus according to claim 1, wherein;

the firing assembly comprises: a firing sleeve and a firing rod at least partially located in the firing sleeve;

the firing rod is connected with the firing connecting member and is configured to be driven by the firing connecting member to move in the direction facing away from the head end;

the firing sleeve is the tube body, the firing sleeve is configured to be driven by the firing rod to move in the direction facing away from the head end, so that the end effector is partially opened.

9. The clip applying mechanism of the clip applying apparatus according to claim 8, wherein the clip applying mechanism further comprises:

an axial engagement mechanism, arranged between the firing connecting member and the firing rod, the firing connecting member and the firing rod being configured to be engaged with each other in an axial direction of the firing connecting member through the axial engagement mechanism, and the firing connecting member and the firing rod are capable of achieving relative movement in a circumferential direction of the firing connecting member.

10. The clip applying mechanism of the clip applying apparatus according to claim 9, wherein the axial engagement mechanism comprises:

a slot, arranged on the firing rod; and a tab, arranged on the firing connecting member, the tab being configured to move in the slot along the circumferential direction of the firing connecting member.

11. The clip applying mechanism of the clip applying apparatus according to claim 10, wherein the slot is an annular slot extending in the circumferential direction of the firing connecting member.

12. The clip applying mechanism of the clip applying apparatus according to claim 1, wherein the clip applying mechanism further comprises:

a housing, the firing connecting member being located in the housing;

a circumferential engagement mechanism, arranged between the firing connecting member and the housing, the firing connecting member and the housing being configured to be engaged with each other in a circumferential direction of the main shaft through the circumferential engagement mechanism, and the firing connecting member and the housing being capable of achieving relative movement in an axial direction of the main shaft.

13. The clip applying mechanism of the clip applying apparatus according to claim 12, wherein:

the housing comprises: a first housing portion and a second housing portion arranged in an axial direction of the tube body, wherein the first housing portion is proximal to the head end, the second housing portion is distal to the head end and is connected with the first housing portion; the first housing portion is configured to be capable of rotating in a circumferential direction of the main shaft relative to the second housing portion;

the circumferential engagement mechanism comprises: a tab arranged on the second housing portion and a slot arranged on the firing connecting member; the tab and the slot are configured to be engaged with each other.

14. The clip applying mechanism of the clip applying apparatus according to claim 13, wherein the circumferential engagement mechanism comprises a plurality of tabs and a plurality of slots, the plurality of tabs and the plurality of slots are configured to be in one-to-one correspondence and be engaged with each other.

15. The clip applying mechanism of the clip applying apparatus according to claim 1, comprising a plurality of engagement mechanisms, the plurality of engagement mechanisms are arranged between the main-shaft connecting member and the firing connecting member along the circumferential direction of the main-shaft connecting member at equal interval.

16. The clip applying mechanism of the clip applying apparatus according to claim 15, wherein the main-shaft connecting member is a tubular member, the plurality of engagement mechanisms comprises two engagement mechanisms, and the two engagement mechanisms are symmetrically arranged in a radial direction of the tubular member.

17. A clip apply apparatus, comprising a clip applying mechanism and a handle assembly, wherein the clip applying mechanism comprising:

a tube body, comprising a head end and a tail end opposite to each other;

a main shaft, the main shaft being arranged proximal to the tail end and at least portion of the main shaft being arranged in the tube body;

a clip-cartridge assembly, the clip-cartridge assembly being configured to penetrate through the tube body and comprising: a clip cartridge arranged in the tube body and an end effector configured to penetrate out of the head end; the clip cartridge being configured to be filled with a clip;

a clip-pushing assembly, at least portion of the clip-pushing assembly being arranged in the tube body, and the clip-pushing assembly being configured to be pushed by the main shaft toward the head end to convey the clip in the clip cartridge into the end effector; and a firing assembly, at least portion of the firing assembly being located in the tube body, and the firing assembly being configured to be pushed by the main shaft toward the head end to close the end effector, so that the clip in the end effector is fired;

wherein the clip applying mechanism further comprises:

a main-shaft connecting member, connected with the main shaft;

a firing connecting member, connected with the firing assembly;

an engagement mechanism, arranged between the main-shaft connecting member and the firing connecting member;

wherein the engagement mechanism, the firing connecting member, the main-shaft connecting member and the firing assembly are configured such that: in a case where the clip is fired, the main-shaft connecting member drives the firing connecting member to move in a direction facing away from the head end through the engagement mechanism, and the firing connecting member drives the firing assembly to move in a same direction, so that the end effector is partially opened, wherein a first engagement member comprises a pin; a second engagement member comprises a slot, the slot comprises a release position and a lock position, the pin is configured to be capable of moving between the release position and the lock position; the slot and the pin are configured such that: in a case where the engagement mechanism is in a lock state, the pin is in the lock position; in a case where the engagement mechanism is in a release state, the pin is in the release position and is capable of moving out of the slot; in a case where the engagement mechanism is in a separate state, the pin is located outside the slot.

18. A clip applying mechanism of a clip applying apparatus, comprising:

a tube body, comprising a head end and a tail end opposite to each other;

a main shaft, the main shaft being arranged proximal to the tail end and at least portion of the main shaft being arranged in the tube body;

a clip-cartridge assembly, the clip-cartridge assembly being configured to penetrate through the tube body and comprising: a clip cartridge arranged in the tube body and an end effector configured to penetrate out of the head end; the clip cartridge being configured to be filled with a clip;

a clip-pushing assembly, at least portion of the clip-pushing assembly being arranged in the tube body, and the clip-pushing assembly being configured to be pushed by the main shaft toward the head end to convey the clip in the clip cartridge into the end effector; and a firing assembly, at least portion of the firing assembly being located in the tube body, and the firing assembly being configured to be pushed by the main shaft toward the head end to close the end effector, so that the clip in the end effector is fired;

wherein the clip applying mechanism further comprises:

a main-shaft connecting member, connected with the main shaft;

a firing connecting member, connected with the firing assembly;

an engagement mechanism, arranged between the main-shaft connecting member and the firing connecting member;

wherein the engagement mechanism, the firing connecting member, the main-shaft connecting member and the firing assembly are configured such that: in a case where the clip is fired, the main-shaft connecting member drives the firing connecting member to move in a direction facing away from the head end through the engagement mechanism, and the firing connecting member drives the firing assembly to move in a same direction, so that the end effector is partially opened, wherein the clip applying mechanism further comprises:

a housing, the firing connecting member being located in the housing;

a circumferential engagement mechanism, arranged between the firing connecting member and the housing, the firing connecting member and the housing being configured to be engaged with each other in a circumferential direction of the main shaft through the circumferential engagement mechanism, and the firing connecting member and the housing being capable of achieving relative movement in an axial direction of the main shaft, wherein the housing comprises: a first housing portion and a second housing portion arranged in an axial direction of the tube body, wherein the first housing portion is proximal to the head end, the second housing portion is distal to the head end and is connected with the first housing portion; the first housing portion is configured to be capable of rotating in a circumferential direction of the main shaft relative to the second housing portion;

the circumferential engagement mechanism comprises: a tab arranged on the second housing portion and a slot arranged on the firing connecting member; the tab and the slot are configured to be engaged with each other.

* * * * *